United States Patent
Scicinski et al.

(10) Patent No.: US 9,884,056 B2
(45) Date of Patent: *Feb. 6, 2018

(54) ORAL PHARMACEUTICAL DOSAGE FORMS

(71) Applicant: Durect Corporation, Cupertino, CA (US)

(72) Inventors: Jan J. Scicinski, Sunnyvale, CA (US); William W. van Osdol, Mountain View, CA (US); Huey-Ching Su, San Jose, CA (US); Michael H. Arenberg, Campbell, CA (US); Jaymin Shah, Sunnyvale, CA (US)

(73) Assignee: Durect Corporation, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,142

(22) Filed: Feb. 16, 2017

(65) Prior Publication Data

US 2017/0252330 A1    Sep. 7, 2017

Related U.S. Application Data

(63) Continuation of application No. 14/791,073, filed on Jul. 2, 2015, now Pat. No. 9,616,055, which is a
(Continued)

(51) Int. Cl.
*A61K 31/4458* (2006.01)
*A61K 9/50* (2006.01)
(Continued)

(52) U.S. Cl.
CPC ........ *A61K 31/4458* (2013.01); *A61K 9/0053* (2013.01); *A61K 9/1617* (2013.01);
(Continued)

(58) Field of Classification Search
None
See application file for complete search history.

(56) References Cited

U.S. PATENT DOCUMENTS

| 2,799,241 A | 7/1957 | Wurster |
| 2,931,802 A | 4/1960 | Toney et al. |

(Continued)

FOREIGN PATENT DOCUMENTS

| AU | 8374575 | 8/1975 |
| CA | 2222567 | 1/2002 |

(Continued)

OTHER PUBLICATIONS

Ash Michael and Ash Irene; "Handbook of Pharmaceutical Additives: An International Guide to More Than 6000 Products by Trade Name, Chemical, Function, and Manufacturer"; *Gower* (1995); 3 pages.

(Continued)

*Primary Examiner* — Aradhana Sasan
(74) *Attorney, Agent, or Firm* — Michael B. Rubin; Bozicevic, Field & Francis LLP

(57) ABSTRACT

Controlled release oral dosage forms suitable for administration of methylphenidate are provided. Abuse-resistant controlled release oral dosage forms suitable for administration of methylphenidate are also provided. Methods of treating ADD and ADHD using the oral dosage forms are also provided.

16 Claims, 16 Drawing Sheets

Related U.S. Application Data continuation of application No. 13/924,232, filed on Jun. 21, 2013, now abandoned, which is a continuation of application No. 12/590,195, filed on Nov. 3, 2009, now abandoned.

(60) Provisional application No. 61/201,015, filed on Dec. 5, 2008, provisional application No. 61/198,244, filed on Nov. 3, 2008.

(51) Int. Cl.
- A61K 9/48 (2006.01)
- A61K 9/16 (2006.01)
- A61K 9/00 (2006.01)

(52) U.S. Cl.
CPC .......... *A61K 9/1623* (2013.01); *A61K 9/4808* (2013.01); *A61K 9/4858* (2013.01); *A61K 9/5084* (2013.01)

(56) References Cited

U.S. PATENT DOCUMENTS

| | | |
|---|---|---|
| 3,339,546 A | 9/1967 | Chen |
| 3,743,398 A | 7/1973 | Johnson et al. |
| 3,845,770 A | 11/1974 | Theeuwes et al. |
| 3,853,837 A | 12/1974 | Fujino et al. |
| 3,916,889 A | 11/1975 | Russell |
| 3,916,899 A | 11/1975 | Theeuwes et al. |
| 3,952,741 A | 4/1976 | Baker |
| 3,992,365 A | 11/1976 | Beddell et al. |
| 3,995,631 A | 12/1976 | Higuchi et al. |
| 4,008,719 A | 2/1977 | Theeuwes et al. |
| 4,014,334 A | 3/1977 | Theeuwes et al. |
| 4,016,880 A | 4/1977 | Theeuwes et al. |
| 4,024,248 A | 5/1977 | Konig et al. |
| 4,063,064 A | 12/1977 | Saunders et al. |
| 4,088,864 A | 5/1978 | Theeuwes et al. |
| 4,100,274 A | 7/1978 | Dutta et al. |
| 4,111,202 A | 9/1978 | Theeuwes |
| 4,160,020 A | 7/1979 | Ayer et al. |
| 4,327,725 A | 5/1982 | Cortese et al. |
| 4,360,019 A | 11/1982 | Portner et al. |
| 4,395,405 A | 7/1983 | Noda et al. |
| 4,395,495 A | 7/1983 | Cummings |
| 4,411,890 A | 10/1983 | Momany |
| 4,487,603 A | 12/1984 | Harris |
| 4,530,840 A | 7/1985 | Tice et al. |
| 4,578,075 A | 3/1986 | Urquhart et al. |
| 4,622,219 A | 11/1986 | Haynes |
| 4,681,583 A | 7/1987 | Urquhart et al. |
| 4,681,765 A | 7/1987 | Guley |
| 4,692,147 A | 9/1987 | Duggan |
| 4,725,442 A | 2/1988 | Haynes et al. |
| 4,725,852 A | 2/1988 | Gamblin et al. |
| 4,767,628 A | 8/1988 | Hutchinson |
| 4,769,372 A | 9/1988 | Kreek |
| 4,795,641 A | 1/1989 | Kashdan |
| 4,834,984 A | 5/1989 | Goldie et al. |
| 4,844,909 A | 8/1989 | Goldie et al. |
| 4,861,598 A | 8/1989 | Oshlack |
| 4,891,225 A | 1/1990 | Langer et al. |
| 4,906,474 A | 3/1990 | Langer et al. |
| 4,931,285 A | 6/1990 | Edgren et al. |
| 4,938,763 A | 7/1990 | Dunn et al. |
| 4,957,681 A | 9/1990 | Klimesch et al. |
| 4,957,744 A | 9/1990 | Delle Valle et al. |
| 4,961,932 A | 10/1990 | Theeuwes |
| 4,970,075 A | 11/1990 | Oshlack |
| 4,990,341 A | 2/1991 | Goldie et al. |
| 5,006,346 A | 4/1991 | Edgren et al. |
| 5,019,397 A | 5/1991 | Wong et al. |
| 5,024,842 A | 6/1991 | Edgren et al. |
| 5,149,543 A | 9/1992 | Cohen et al. |
| 5,156,850 A | 10/1992 | Wong et al. |
| 5,160,743 A | 11/1992 | Edgren et al. |
| 5,188,837 A | 2/1993 | Domb |
| 5,190,765 A | 3/1993 | Jao et al. |
| 5,252,338 A | 10/1993 | Jao et al. |
| 5,266,331 A | 11/1993 | Oshlack et al. |
| 5,273,760 A | 12/1993 | Oshlack et al. |
| 5,278,201 A | 1/1994 | Dunn et al. |
| 5,278,202 A | 1/1994 | Dunn et al. |
| 5,286,493 A | 2/1994 | Oshlack et al. |
| 5,286,496 A | 2/1994 | Stapler et al. |
| 5,324,351 A | 6/1994 | Oshlack et al. |
| 5,324,519 A | 6/1994 | Dunn et al. |
| 5,324,520 A | 6/1994 | Dunn et al. |
| 5,330,835 A | 7/1994 | Kikuchi et al. |
| 5,340,572 A | 8/1994 | Patel et al. |
| 5,340,849 A | 8/1994 | Dunn et al. |
| 5,350,741 A | 9/1994 | Takada |
| 5,352,662 A | 10/1994 | Brooks et al. |
| 5,356,467 A | 10/1994 | Oshlack et al. |
| 5,356,635 A | 10/1994 | Raman et al. |
| 5,366,738 A | 11/1994 | Rork et al. |
| 5,382,424 A | 1/1995 | Stapler et al. |
| 5,391,381 A | 2/1995 | Wong et al. |
| 5,399,363 A | 3/1995 | Liversidge et al. |
| 5,472,712 A | 12/1995 | Oshlack et al. |
| 5,478,577 A | 12/1995 | Sackler et al. |
| 5,487,898 A | 1/1996 | Lu et al. |
| 5,508,042 A | 4/1996 | Oshlack et al. |
| 5,540,912 A | 7/1996 | Roorda et al. |
| 5,545,408 A | 8/1996 | Trigg et al. |
| 5,549,912 A | 8/1996 | Oshlack et al. |
| 5,569,450 A | 10/1996 | Duan et al. |
| 5,580,578 A | 12/1996 | Oshlack et al. |
| 5,599,552 A | 2/1997 | Dunn et al. |
| 5,620,705 A | 4/1997 | Dong et al. |
| 5,633,000 A | 5/1997 | Grossman et al. |
| 5,633,011 A | 5/1997 | Dong et al. |
| 5,639,476 A | 6/1997 | Oshlack et al. |
| 5,656,295 A | 8/1997 | Oshlack et al. |
| 5,672,360 A | 9/1997 | Sackler et al. |
| 5,681,585 A | 10/1997 | Oshlack et al. |
| 5,702,716 A | 12/1997 | Dunn et al. |
| 5,725,841 A | 3/1998 | Duan et al. |
| 5,728,396 A | 3/1998 | Peery et al. |
| 5,733,950 A | 3/1998 | Dunn et al. |
| 5,736,152 A | 4/1998 | Dunn |
| 5,739,176 A | 4/1998 | Dunn et al. |
| 5,744,280 A | 4/1998 | Mooney, III et al. |
| 5,747,051 A | 5/1998 | Granger et al. |
| 5,747,058 A | 5/1998 | Tipton et al. |
| 5,750,100 A | 5/1998 | Yamagata et al. |
| 5,759,563 A | 6/1998 | Yewey et al. |
| 5,777,124 A | 7/1998 | Zavareh et al. |
| 5,780,044 A | 7/1998 | Yewey et al. |
| 5,786,484 A | 7/1998 | Dyer et al. |
| 5,837,284 A | 11/1998 | Mehta et al. |
| 5,840,329 A | 11/1998 | Bai |
| 5,840,731 A | 11/1998 | Mayer et al. |
| 5,879,705 A | 3/1999 | Haefield et al. |
| 5,908,850 A | 6/1999 | Zeitlin et al. |
| 5,919,473 A | 7/1999 | Elkhoury et al. |
| 5,932,597 A | 8/1999 | Brown et al. |
| 5,942,241 A | 8/1999 | Chasin et al. |
| 5,958,446 A | 9/1999 | Miranda et al. |
| 5,958,452 A | 9/1999 | Oshlack et al. |
| 5,965,161 A | 10/1999 | Oshlack et al. |
| 5,968,542 A | 10/1999 | Tipton |
| 5,985,305 A | 11/1999 | Peery et al. |
| 5,994,548 A | 11/1999 | Langston et al. |
| 6,008,355 A | 12/1999 | Huang et al. |
| 6,042,811 A | 3/2000 | Duan et al. |
| 6,051,558 A | 4/2000 | Burns et al. |
| 6,093,419 A | 7/2000 | Rolf |
| 6,126,919 A | 10/2000 | Stefely et al. |
| 6,143,322 A | 11/2000 | Sackler et al. |
| 6,190,680 B1 | 2/2001 | Sakurada et al. |
| 6,203,813 B1 | 3/2001 | Gooberman et al. |
| 6,210,705 B1 | 4/2001 | Mantelle et al. |
| 6,228,398 B1 | 5/2001 | Devane et al. |

(56) References Cited

U.S. PATENT DOCUMENTS

| | | |
|---|---|---|
| 6,245,351 B1 | 6/2001 | Nara et al. |
| 6,291,013 B1 | 9/2001 | Gibson et al. |
| 6,294,195 B1 | 9/2001 | Osillack et al. |
| 6,312,717 B1 | 11/2001 | Molinoff et al. |
| 6,344,215 B1 | 2/2002 | Bettman et al. |
| 6,348,211 B1 | 2/2002 | Mantelle et al. |
| 6,355,656 B1 | 3/2002 | Zeitlin et al. |
| 6,375,957 B1 | 4/2002 | Kaiko et al. |
| 6,384,227 B2 | 5/2002 | Dyer et al. |
| 6,403,609 B1 | 6/2002 | Asgharian et al. |
| 6,413,356 B1 | 7/2002 | Chokshi et al. |
| 6,413,536 B1 | 7/2002 | Gibson et al. |
| 6,419,960 B1 | 7/2002 | Krishnamurthy |
| 6,426,339 B1 | 7/2002 | Berde et al. |
| 6,440,493 B1 | 8/2002 | Gibson et al. |
| 6,479,074 B2 | 11/2002 | Murdock et al. |
| 6,486,138 B1 | 11/2002 | Asgharian et al. |
| 6,498,153 B1 | 12/2002 | Cady et al. |
| 6,512,009 B1 | 1/2003 | Daoust et al. |
| 6,514,516 B1 | 2/2003 | Chasin et al. |
| 6,521,259 B1 | 2/2003 | Chasin et al. |
| 6,524,607 B1 | 2/2003 | Goldenheim et al. |
| 6,528,530 B2 | 3/2003 | Zeitlin et al. |
| 6,552,031 B1 | 4/2003 | Burch et al. |
| 6,635,284 B2 | 10/2003 | Mehta et al. |
| 6,699,908 B2 | 3/2004 | Sackler et al. |
| 6,730,325 B2 | 5/2004 | Devane et al. |
| 6,733,783 B2 | 5/2004 | Oshlack et al. |
| 6,919,373 B1 | 7/2005 | Lam et al. |
| 6,921,541 B2 | 7/2005 | Chasin et al. |
| 6,930,129 B2 | 8/2005 | Lam et al. |
| 6,992,065 B2 | 1/2006 | Okumu et al. |
| 7,053,209 B1 | 5/2006 | Gibson et al. |
| 7,431,944 B2 | 10/2008 | Mehta et al. |
| 7,691,880 B2 | 4/2010 | Herman |
| 7,833,543 B2 | 11/2010 | Gibson et al. |
| 7,838,522 B2 | 11/2010 | Esposito et al. |
| 8,124,123 B2 | 2/2012 | Pillai et al. |
| 8,133,507 B2 | 3/2012 | Yum et al. |
| 8,147,870 B2 | 4/2012 | Yum et al. |
| 8,153,152 B2 | 4/2012 | Yum et al. |
| 8,163,798 B2 | 4/2012 | Gupta et al. |
| 8,168,217 B2 | 5/2012 | Yum et al. |
| 8,354,124 B2 | 1/2013 | Yum et al. |
| 8,415,401 B2 | 4/2013 | Yum et al. |
| 8,420,120 B2 | 4/2013 | Yum et al. |
| 8,945,614 B2 | 2/2015 | Yum et al. |
| 8,951,556 B2 | 2/2015 | Yum et al. |
| 8,974,821 B2 | 3/2015 | Yum et al. |
| 9,233,160 B2 | 1/2016 | Yum et al. |
| 9,517,271 B2 | 12/2016 | Yum et al. |
| 9,572,885 B2 | 2/2017 | Yum et al. |
| 9,592,204 B2 | 3/2017 | Yum et al. |
| 9,616,055 B2 * | 4/2017 | Scicinski ............ A61K 31/4458 |
| 9,655,861 B2 | 5/2017 | Yum et al. |
| 2001/0000522 A1 | 4/2001 | Dyer et al. |
| 2001/0029257 A1 | 10/2001 | Murdock et al. |
| 2001/0047005 A1 | 11/2001 | Farrar et al. |
| 2001/0055613 A1 | 12/2001 | Burnside et al. |
| 2002/0086878 A1 | 7/2002 | Dobrozsi et al. |
| 2002/0114835 A1 | 8/2002 | Sackler et al. |
| 2002/0143065 A1 | 10/2002 | Liu et al. |
| 2003/0004177 A1 | 1/2003 | Kao et al. |
| 2003/0045454 A1 | 3/2003 | Okumu et al. |
| 2003/0152637 A1 | 8/2003 | Chasin et al. |
| 2003/0157168 A1 | 8/2003 | Breder et al. |
| 2003/0165562 A1 | 9/2003 | Gutierrez-Rocca et al. |
| 2003/0185873 A1 | 10/2003 | Chasin et al. |
| 2003/0191147 A1 | 10/2003 | Sherman et al. |
| 2004/0001889 A1 | 1/2004 | Chen et al. |
| 2004/0024021 A1 | 2/2004 | Sudo et al. |
| 2004/0052336 A1 | 3/2004 | Langlet et al. |
| 2004/0101557 A1 | 5/2004 | Gibson et al. |
| 2004/0109893 A1 | 6/2004 | Chen et al. |
| 2004/0138237 A1 | 7/2004 | Shah |
| 2004/0146562 A1 | 7/2004 | Shah |
| 2004/0161382 A1 | 8/2004 | Yum et al. |
| 2004/0224020 A1 | 11/2004 | Schoenhard |
| 2004/0224903 A1 | 11/2004 | Berry et al. |
| 2005/0042194 A1 | 2/2005 | Ng et al. |
| 2005/0106304 A1 | 5/2005 | Cook et al. |
| 2005/0158382 A1 | 7/2005 | Cruz et al. |
| 2005/0171052 A1 | 8/2005 | Cook et al. |
| 2005/0208132 A1 | 9/2005 | Sathyan et al. |
| 2005/0232876 A1 | 10/2005 | Minga et al. |
| 2005/0244489 A1 | 11/2005 | Paris |
| 2005/0260264 A1 | 11/2005 | Edgren et al. |
| 2005/0266087 A1 | 12/2005 | Junnarkar et al. |
| 2006/0034926 A1 | 2/2006 | Fraatz et al. |
| 2006/0058401 A1 | 3/2006 | Ishikawa et al. |
| 2006/0104909 A1 | 5/2006 | Vaghefi et al. |
| 2006/0115527 A1 | 6/2006 | Hassan et al. |
| 2006/0165800 A1 | 7/2006 | Chen et al. |
| 2006/0210599 A1 | 9/2006 | Gibson et al. |
| 2007/0027105 A1 | 2/2007 | Junnarkar et al. |
| 2007/0031502 A1 | 2/2007 | Pettersson et al. |
| 2007/0104763 A1 | 5/2007 | Jobdevairakkam et al. |
| 2007/0259033 A1 | 11/2007 | Cruz |
| 2008/0023261 A1 | 1/2008 | Kaneko et al. |
| 2008/0026052 A1 | 1/2008 | Schoenhard |
| 2008/0145419 A1 | 6/2008 | Gibson et al. |
| 2008/0152708 A1 | 6/2008 | Gibson et al. |
| 2008/0206321 A1 | 8/2008 | Yum et al. |
| 2009/0023689 A1 | 1/2009 | Yum et al. |
| 2009/0023690 A1 | 1/2009 | Yum et al. |
| 2009/0164240 A1 | 6/2009 | Friedmann et al. |
| 2009/0165578 A1 | 7/2009 | Zamloot et al. |
| 2009/0169631 A1 | 7/2009 | Zamloot et al. |
| 2009/0215808 A1 | 8/2009 | Yum et al. |
| 2009/0298862 A1 | 12/2009 | Yum et al. |
| 2010/0260844 A1 | 10/2010 | Scicinski et al. |
| 2011/0287093 A1 | 11/2011 | Schoenhard |
| 2012/0135072 A1 | 5/2012 | Yum et al. |
| 2012/0135073 A1 | 5/2012 | Yum et al. |
| 2012/0165358 A1 | 6/2012 | Cruz et al. |
| 2013/0281480 A1 | 10/2013 | Yum et al. |
| 2013/0287845 A1 | 10/2013 | Yum et al. |
| 2013/0295168 A1 | 11/2013 | Yum et al. |
| 2013/0309176 A1 | 11/2013 | Port et al. |
| 2013/0317049 A1 | 11/2013 | Yum et al. |
| 2013/0337059 A1 | 12/2013 | Yum et al. |
| 2013/0337060 A1 | 12/2013 | Yum et al. |
| 2014/0275147 A1 | 9/2014 | Yum et al. |
| 2015/0196644 A1 | 7/2015 | Yum et al. |
| 2016/0038592 A1 | 2/2016 | Yum et al. |
| 2016/0136102 A1 | 5/2016 | Yum et al. |
| 2016/0193345 A1 | 7/2016 | Yum et al. |
| 2016/0038479 A1 | 9/2016 | Yum et al. |
| 2016/0303242 A1 | 10/2016 | Yum et al. |
| 2017/0165255 A1 | 6/2017 | Yum et al. |
| 2017/0196978 A1 | 7/2017 | Yum et al. |
| 2017/0209581 A1 | 7/2017 | Yum et al. |

FOREIGN PATENT DOCUMENTS

| | | |
|---|---|---|
| DE | 1569231 | 8/1969 |
| DE | 2213717 | 11/1972 |
| DE | 2321174 | 4/1973 |
| DE | 2438352 | 2/1976 |
| DE | 2720245 | 11/1977 |
| DE | 19714765 | 10/1998 |
| EP | 0244118 | 11/1987 |
| EP | 0535899 | 4/1993 |
| EP | 0539559 | 5/1993 |
| EP | 0539751 | 5/1993 |
| EP | 0544612 | 6/1993 |
| EP | 0621042 | 10/1994 |
| EP | 0290983 | 1/1995 |
| EP | 0640336 | 3/1995 |
| EP | 0773034 | 5/1997 |
| EP | 0778768 | 6/1997 |
| EP | 0537559 | 1/1998 |
| EP | 0711548 | 1/1998 |
| EP | 0635531 | 6/2001 |

(56) References Cited

FOREIGN PATENT DOCUMENTS

| | | |
|---|---|---|
| EP | 0782569 | 3/2002 |
| EP | 1010436 | 10/2002 |
| EP | 0804417 | 6/2003 |
| EP | 0788480 | 7/2003 |
| EP | 0788481 | 8/2003 |
| EP | 0999825 | 10/2003 |
| EP | 1348427 | 10/2003 |
| EP | 1032390 | 11/2003 |
| EP | 1548093 | 6/2005 |
| EP | 2510924 | 10/2012 |
| GB | 1088992 | 10/1967 |
| GB | 2238478 | 6/1991 |
| JP | 59210024 | 11/1984 |
| JP | 62000419 | 1/1987 |
| JP | 2096516 | 4/1990 |
| JP | 5194273 | 8/1993 |
| JP | 7053356 | 2/1995 |
| JP | 7112940 | 5/1995 |
| JP | 7115901 | 5/1995 |
| JP | 7124196 | 5/1995 |
| JP | 9502181 | 3/1997 |
| JP | 11507278 | 6/1999 |
| JP | 2001516728 | 10/2001 |
| JP | 2003508449 | 3/2003 |
| WO | WO 1990003768 | 4/1990 |
| WO | WO 1990003809 | 4/1990 |
| WO | WO 1991018016 | 11/1991 |
| WO | WO 199214466 | 3/1992 |
| WO | WO 1992017900 | 10/1992 |
| WO | WO 1993003751 | 3/1993 |
| WO | WO 1993007833 | 4/1993 |
| WO | WO 1994005265 | 3/1994 |
| WO | WO 1994015587 | 7/1994 |
| WO | WO 1995009613 | 4/1995 |
| WO | WO 1995017901 | 7/1995 |
| WO | WO 1996009290 | 3/1996 |
| WO | WO 1996012699 | 5/1996 |
| WO | WO 1996012700 | 5/1996 |
| WO | WO 1996022281 | 7/1996 |
| WO | WO 1996039995 | 12/1996 |
| WO | WO 1996041616 | 12/1996 |
| WO | WO 1997015285 | 5/1997 |
| WO | WO 1997027840 | 8/1997 |
| WO | WO 1997049391 | 12/1997 |
| WO | WO 1998027962 | 7/1998 |
| WO | WO 1998027963 | 7/1998 |
| WO | WO 1998034596 | 8/1998 |
| WO | WO 1998044903 | 10/1998 |
| WO | WO 1998051246 | 11/1998 |
| WO | WO 1998053837 | 12/1998 |
| WO | WO 1999006023 | 2/1999 |
| WO | WO 1999013913 | 3/1999 |
| WO | WO 1999025349 | 5/1999 |
| WO | WO 2000000120 | 1/2000 |
| WO | WO 200016750 | 3/2000 |
| WO | WO 2000078335 | 12/2000 |
| WO | WO 2001008661 | 2/2001 |
| WO | WO 2001015734 | 3/2001 |
| WO | WO 2001051024 | 7/2001 |
| WO | WO 2001076599 | 10/2001 |
| WO | WO 2002010436 | 2/2002 |
| WO | WO 2002053187 | 7/2002 |
| WO | WO 2002087512 | 11/2002 |
| WO | WO 2003000282 | 1/2003 |
| WO | WO 2003013476 | 2/2003 |
| WO | WO 2003055475 | 7/2003 |
| WO | WO 2003086368 | 10/2003 |
| WO | WO 2003101358 | 12/2003 |
| WO | WO 2004026262 | 4/2004 |
| WO | WO 2004037224 | 5/2004 |
| WO | WO 2004037289 | 5/2004 |
| WO | WO 2004052336 | 6/2004 |
| WO | WO 2004056337 | 7/2004 |
| WO | WO 2004056338 | 7/2004 |
| WO | WO 2004082658 | 9/2004 |
| WO | WO 2004101557 | 11/2004 |
| WO | WO 2005009408 | 2/2005 |
| WO | WO 2005048744 | 6/2005 |
| WO | WO 2005105031 | 11/2005 |
| WO | WO 2005112896 | 12/2005 |
| WO | WO 2005115333 | 12/2005 |
| WO | WO 2006008141 | 1/2006 |
| WO | WO 2006069293 | 6/2006 |
| WO | WO 2006084139 | 8/2006 |
| WO | 2006134018 | 12/2006 |
| WO | WO 2007058923 | 5/2007 |
| WO | 2007070632 | 6/2007 |
| WO | 2007135193 | 11/2007 |
| WO | WO 2008023261 | 2/2008 |
| WO | WO 2009076227 | 6/2009 |
| WO | WO 2009076231 | 6/2009 |
| WO | WO 2009076236 | 6/2009 |
| WO | WO 2009088414 | 7/2009 |
| WO | WO 2013142279 | 9/2013 |
| WO | WO 2014144984 | 3/2014 |
| WO | WO 2004054542 | 7/2014 |
| WO | WO 2014144975 | 9/2014 |

OTHER PUBLICATIONS

Blažková, A. et al; "Viscosity properties of aqueous solutions of hydroxyethylcellulose"; *Chem Papers* 44(3); (1990); pp. 289-301.

"CAB-O-SIL®, Untreated Fumed Silica: Properties & Functions"; *Cabot Corporation, Cab-O-Sil Division*; (1993); pp. 1-34.

Friedmann N, Klutzaritz V, Webster L.; "Efficacy and safety of an extended-release oxycodone (Remoxy) formulation in patients with moderate to severe osteoarthritic pain"; *J Opioid Manag.* 7(3); (2011); pp. 193-202.

Friedmann N, Klutzaritz V, Webster L.; "Long-term safety of Remoxy(R) (extended-release oxycodone) in patients with moderate to severe chronic osteoarthritis or low back pain"; *Pain Med.* 12(5); (2011); pp. 755-760.

"General Characteristics of Polymers"; Museum of Fine Arts, Boston; (2007); pp. 1-4.

Hays Lon R.; "A profile of OxyContin addiction"; *Journal of Addictive Diseases* 23(4); (2004); pp. 1-9.

Japanese Office Action for Japanese Application No. 2010-537128, dated Jun. 5, 2013.

Kamel S., et al; "Pharmaceutical significance of cellulose: A review"; *eXPRESS Polymer Letters*vol. 2, No. 11; (2008); pp. 758-778.

Malhotra Bimal K. et al; . "The pharmacokinetics of oxycodone and its metabolites following single oral doses of Remoxy®, an abuse-deterrent formulation of extended-release oxycodone, in patients with hepatic or renal impairment"; *Journal of Opioid Management* 11:2; Mar./Apr. 2015; pp. 157-169.

"NATROSOL® Hydroxyethylcellulose a Nonionic Water-Soluble Polymer"; *Hercules Incorporated, Aqualon Division*; (1999); pp. 1-24.

Saeio, Kiattisak, et al; "Factors Influencing Drug Dissolution Characteristic From Hydrophilic Polymer Matrix Tablet"; *Scientia Pharmaceutica (Sci. Pharm)* 75; (2007); pp. 147-163.

Selimovic, Seila, and Hu Yue; "Aging Effects in Suspensions of Silica Particles"; *Mat. Res. Soc. Symp. Proc.*, vol. 790 *Materials Research Society*; (2004) pp. P7.11.1-P7.11.6.

Setnik B, Roland CL, Cleveland JM, Webster L.; "The abuse potential of Remoxy®, an extended-release formulation of oxycodone, compared with immediate- and extended-release oxycodone"; Pain Med. 2011; 12(4):618-631.

Webster LR.; "PTI-821: sustained-release oxycodone using gel-cap technology"; *Expert Opin Investig Drugs.* 16(3); (2007); pp. 359-366.

Zamloot M, et al.; "Remoxy®: a novel formulation of extended-release oxycodone developed using the ORADURO® technology"; *J Appl Res.* 10(3) (2010); pp. 88-96.

"New Drugs/Programs"; *Current Drug Discovery*; Nov. 2004; pp. 7-10.

(56) References Cited

OTHER PUBLICATIONS

"Ritalin product monograph"; *CPS Compendium of Pharmaceuticals and Specialties*, 34th ed.; Gillis, M., Ed. Canadian Pharmacists Association: Ottawa, (1999); pp. 1573-1574.
3M, "3M DDS Announces Development of New HFA-Compatible Exipients: Novel Oligomeric Acids as MDI Suspension Aid and Solubilizers" *3M Delivery Newsletter*, vol. 15, *3M Drug Delivery Systems*; Jun. 2000, pp. 9-11.
Abdul-Fattah, Ahmad M., et al; "Preparation and In Vitro Evaluation of Solid Dispersions of Halofantrine."; *International Journal of Pharmaceutics* 235; (2002); pp. 17-33.
Adams, Edgar G, et al.; "A comparison of the abuse liability of tramadol, NSAIDS, and hydrocodone in patients with chronic pain"; *Journal of Pain and Symptom Management.* 31(5); (2006); pp. 465-476.
Ajayaghosh, A., et al., "Solid-Phase Synthesis of N-Methyl- and N-Ethylamides of Peptides Using Photolytically Detachable ((3-Nitro-4-((alkylamino)methyl)benzamido)methyl)polystyrene Resin"; *J. Org. Chem.* 55; (1990); pp. 2826-2829.
Allahham Allahham, et al; "Flow and injection characteristics of pharmaceutical parenteral formulations using a micro-capillary rheometer"; *International Journal of Pharmaceutics.* 270; (2004); pp. 139-148.
Ansel, H.C. et al.; *Pharmaceutical Dosage Forms and Drug Delivery System, sixth ed.,* (1995); 20 pages.
Aungst, B.J., et al; "Improved Oral Bioavailability of an HIV Protease Inhibitor Using Gelucire 44/14 and Labrasol Vehicles"; *Bulletin Technique Gattefosse*, No. 87; (1994); pp. 49-54.
Aungst, B.J., et al; "Amphiphilic vehicles improve the oral bioavailability of a poorly soluble HIV Protease inhibitor at high doses."; *International Journal of Pharmaceutics*, vol. 156; (1997); pp. 79-88.
Bansal, Tripta, et al; "Solid Self Nanoemulsifying Delivery Systems as a Platform Technology for Formulation of Poorly Soluble Drugs"; *Critical Reviews™ in Therapeutic Drug Carrier Systems*, 25(1); (2008); pp. 63-116.
Barakat, N.S.; "Etodolac-Liquid-Filled Dispersion into Hard Gelatin Capsules: An Approach to Improve Dissolution and Stability of Etodolac Formulation"; *Drug Development and Indistrial Pharmacy.* 32; (2006); pp. 865-876.
Barb, R., et al.; "Evaluation of the SABER Delivery System for the Controlled Release of Deslorelin: Effect of Dose in Estrogen Primed Ovarectomized Gilts"; *Proceed. Int'l, Symp. Control. Rel. Bioact. Mater.*; (1999) Controlled Release Society, Inc.; pp. 1170-1171.
Barker, S.A., et al; "An investigation into the structure and bioavailability of α-tocopherol in dispersions Gelucire 44/14"; *Journal of Controlled Release* 91; (2003); pp. 477-488.
Becker & Johnson "Effects of Gonadotropin-Releasing Hormone Infused in a Pulsatile or Continuous Fashion Serum Gonadotropin Concentrations and Ovulation in the Mare"; *J. Anim. Sci.* vol. 70; (1992);. pp. 1208-1215.
Bekersky I, et al.; "Effect of low- and high-fat meals on tacrolimus absorption following 5 mg single oral doses to healthy human subjects"; *J Clin Pharmacol*; 41; (2001); pp. 176-182.
Berge et al. "Pharmaceutical salts" *J Pharm. Sci.* 66(1); Jan. 1977; pp. 1-19.
Betschart, R., et al.; "Evaluation of the SABER™ Delivery System for the Controlled Release of the GnRH Analogue Deslorelin for Advancing Ovulation in Mares: Effect of Gamma Radiation"; *Proceed. In'l. Symp. Control. Rel. Bioact. Mater., 25, Controlled Release Society, Inc.*; (1998); pp. 655-656.
Blachez, P., et al; "Development of immediate release pellets of poorly soluble compounds using Gelucire® 44/14 using melt pelletization"; *Poster, Conference "AAPS Annual Meeting & Exposition"*; Salt Lake City, Utah, United States; Oct. 26, 2003; 2 pages.
Brevard J, et al. "Pain and opioid abuse in a population of substance abuse patients: data from the NAVIPPRO™ system." *Conference paper presented at the 42nd American Pain Society (APS) Annual Scientific Meeting*, Washington D.C.; (2007); 1 page.
Bühler, K.; GnRH Agonists and Safety, In GnRH Analagoues the State of the Art 1993, A Summary of the 3rd International Symposium on GnRH Analogues in Cancer and Human Reproduction, Geneva, Feb. 1993; pp. 139-146.
Burns, P. et al.; "Pharmacodynamic Evaluation of the Saber™ Delivery System for the Controlled Release of the GnRH Analogue Deslorelin Acetate for Advancing Ovulation in Cyclic Mares"; *Proceed. Int'l. Symp. Control. Rel. Bioact. Mater., 24; Controlled Release Society Inc.* (1997); 4 pages.
Carraway, et al.; "Drug Delivery From a Controlled Release Aerosol: Effects of Formulation Variables", *APPS J Abstract. Southern BioSystems, Inc.*, Birmingham AL, USA; (2000); 1 page.
Carraway, et al.; "Drug Release from a Novel Controlled Release Aerosol Based on Sucrose Acetate Isobutyrate" *AAPS Midwest Regional Meeting Chicago*, IL; May 22, 2000; 2 pages.
Cellulose Acetate Butyrate. In: European pharmacopoeia. 4 edn. Strasbourg Cedex, France: Council of Europe; (2001); pp. 853-854.
Chambin, O.; et al; "Interest of Multifunctional Lipid Excipients: Case of Gelucire® 44/14"; *Drug Development and Industrial Pharmacy*, 31; (2005); pp. 527-534.
Chambin, O., et al; "Influence of drug polarity upon the solid-state structure and release properties of self-emulsifying drug delivery systems in relation with water affinity"; *Colloids and Surfaces B: Biointerfaces* 71; (2009); pp. 73-78.
Chauhan, Bhaskar, et al; "Preparation and Characterization of Etoricoxib Solid Dispersions Using Lipid Carriers by Spray Drying Technique"; *AAPS PharmSciTech* 6(3), Article 50; (http://www.aapspharmscitech.org); (2005); pp. E405-E412.
Chauhan, B., et al; "Preparation and evaluation of glibenclamide-polyglycolized glycerides solid dispersions with silicon dioxide by spray drying technique"; *European J. Pharm. Sci.* 26(2); (2005); pp. 219-230.
Chen, X. Q., et al; "Evaluation of Lipid-Based Formulations in Dogs and Monkeys for a Highly Lipophilic Compound"; *Conference "Annual Meeting of AAPS"*; (2007); San Diego, CA; poster abstract; 1 page.
Coy, et al.; "Solid Phase Synthesis of Lutenizing Hormone-Releasing Hormone and Its Analogs"; *Methods Enzymol.* 37; (1975); pp. 416-424.
Cuine, Jean F., et al; "Evaluation of the Impact of Surfactant Digestion on the Bioavailability of Danazol after Oral Administration of Lipidic Self-Emulsifying Formulations to Dogs"; *Journal of Pharmaceutical Sciences*, vol. 97 No. 2; Feb. 2008; pp. 995-1012; article first published online Dec. 6, 2007.
Damian, Festo, et al; "Physicochemical characterization of solid dispersions of the antiviral agent UC-781 with polyethylene glycol 6000 and Gelucire 44/14"; *European Journal of Pharmaceutical Sciences* 10; (2000); pp. 311-322.
Darling, et al. (2000) "Extended Release of Human Growth Hormone Suspended in SABER™ Formulation Design and in Vitro Assessment" Genentech, Inc., South San Francisco, CA USA and Southern BioSystems, Inc. Birmingham AL, USA. Poster; 1 page.
DataRase WPI Section Ch, Week 198532 Derwent Publications Ltd., London GB; Class B07, AN 1985-193549 XP002284488 & JP 60120811 A (Sealer, R P KK) Jun. 28, 1985 (Abstract).
Desai et al.; "Surface Modification of Polymeric Biomaterials for Reduced Thrombogenicity"; *Polym. Mater. Sci. Eng.*, 62; Jun. 1990;. pp. 731-735.
Dodson, K.M., et al. "Oral Controlled Release of Antiretrovirals Using the SABER Delivery System Incorporated into Soft Gelatin Capsules", *AAPS Meeting*, (1999), New Orleans, LA.; 2 pages.
Dordunoo, S.K., et al; "Preformulation Studies on Solid Dispersions Containing Triamterene or Temazepam in Polyethylene Glycols or Gelucire 44/14 for Liquid Filling of Hard Gelatin Capsules"; *Drug Development and Industrial Pharmacy*, vol. 17, No. 12; (1991); pp. 1685-1713.
Dordunoo, Stephen K., et al; "Solidification studies of polyethylene glycols, Gelucire® 44/14 or their dispersions with Triamterene or Temazepam"; *Journal of Pharm. Pharmacology* 48; (1996); pp. 782-789.

(56) References Cited

OTHER PUBLICATIONS

Duan, D.C. et al.; "Novel Dispersing Aids for Hydrofluoroalkane-Based Metered Dose Inhalers"; *1998 Conference of the American Association of Pharmaceutical Scientists*, San Francisco, California; Nov. 1998; 1 page.

Duan, D.C. et al., "Oligomeric Lactic Acids as Solubilizing Aids for HFA-Based Metered Dose Inhalers"; *1998 Conference of the American Association of Pharmaceutical Scientists*, San Francisco, California; Nov. 1998; 1 page.

Dunbar SA, Katz NP; "Chronic opioid therapy for nonmalignant pain in patients with a history of substance abuse: report of 20 cases." *Journal of Pain and Symptom Management*. 11(3); (1996) pp. 163-171.

Edimo, A., et al; "Capacity of Lipophilic Auxiliary Substances to Give Spheres by Extrusion—Spheronization"; *Drug Development and Industrial Pharmacy*, 19(7); (1993); pp. 827-842.

Eliasen, Helle, et al; "Effects of binder rheology on melt agglomeration in a high shear mixer"; *International Journal of Pharmaceutics* 176; (1998); pp. 73-83.

Fernandez, Sylvie, et al; "Lipolysis of the semi-solid self-emulsifying excipient Gelucire® 44/14 by digestive lipases"; *Biochimica et Biophysica Acta* 1781; (2008); pp. 367-375; available online Jun. 3, 2008.

Fitzgerald, B. P., et al., "Effect of Constant Administration of a Gonadotropin-Releasing Hormone Agonist on Reproductive Activity in Mares: Preliminary Evidence on Suppression of Ovulation During the Breeding Season"; *Am. J. Vet. Res.*, vol. 54, No. 10; Oct. 1993; pp. 1746-1751.

Fleury, J., et al., "Evaluation of the Saber.TM. Delivery System for the Controlled Release of the Deslorelin for Advancing Ovulation in the Mare: Effects of Formulation & Dose," Proceed. Int'l. Symp. Control. Rel. Bioact. Mater. 25 (1998) Controlled Release Society, Inc. pp. 657-658.

Gad, Shayne C., et al; "Nonclinical Vehicle Use in Studies by Multiple Routes in Multiple Species"; *International Journal of Toxicology*, 25; Sep. 20, 2006; pp. 1-23.

Gattefossé Corporation (1989); "To Help With Your Impossible Formulations: A Guide to Gattefossé Liquid Excipients"; 6 pages.

Gattefossé (1998); "Oral Route Excipients"; 8 pages.

GELUCIRE® 44/14 brochure (1999); "Immediate Release and Enhanced Bioavailability"; pp. 1-16.

GELUCIRE® Technical Dossier; "Answering the Need for Enhanced Bioavailability"; Oct. 1996; 16 pages.

GELUCIRE® (1996); "Answering the Need for Enhanced Bioavailability"; 5 pages.

Gibson, et al.; "Effects of Formulation Variables on Controlled Release of Paclitaxel and other Chemotherapeutic Agents from a Novel Delivery System" *AAPS New Orleans, LA*; (1999); Southern BioSystems, Inc. Birmingham AL, USA; 2 pages.

Gibson, et al.; "In Vitro and In Vivo Evaluation of a Novel In Situ-Forming Pareteral Delivery System"; *Meeting of Recent Advances in Drug Delivery Systems*, Salt Lake City UT; (1999); Southern BioSystems, Inc. Birmingham AL, USA; 2 pages.

Gilderman L., et al; "Remoxy™: A New Opioid Drug With Effective Analgesia and Abuse-Resistance." *American Pain Society Annual Meeting*, San Antonio, TX, May 2006; 1 page.

Ginther, O.J.; "Follicles"; *Ultrasonic Imaging and Reproductive Events in the Mare*. EquiServices, Chapter 4; Cross Plains, WI; (1986); pp. 43-72.

Ginther, O.J., "Effect of a Synthetic Gonadotropin-Releasing Hormone on Plasma Concentrations of Luteinizing Hormone in Ponies", *Am. J. Vet. Res.*, 1 vol. 35, No. x; Jan. 1974; pp. 79-88.

Ginther, O.J., "Reproductive Efficiency", *Reproductive Biology of the Mare Basic and Applied Aspects*, Second Ed., Chapter 12; (1992); pp. 499-509.

Glajchen, M. "Chronic Pain: Treatment Barriers and Strategies for Clinical Practice." J AM Board Fam Pract. 2001; 14(3): 178-183.

González et al; "Methylphenidate bioavailability from two extended-release formulations"; *International Journal of Clinical Pharmacology Therapeutics*, vol. 40, No. 4; (2002) pp. 175-184.

Gould, Phillip L.; "Salt selection for basic drugs"; *International Journal of Pharmaceutics*, 33 (1986); pp. 201-217.

Greydanus, D. E.; "Psychopharmacology for ADHD in Adolescents: Quo Vadis?"; *Psychiatric Times* vol. 20, No. 5; May 5, 2003; pp. 1-7.

Handbook of Pharmaceutical Excipients: Sixth Edition; "Medium-chain Triglycerides"; *Pharmaceutical Press and American Pharmacists Association* 2009; pp. 429-431.

Harrison, L.A., et al.; "Comaprison of HCG, Buserelin and Luprostiol for Induction of Ovulation in Cycling Mares"; *Equine Veterinary Science*, vol. 11, No. 3; (1991); pp. 163-166.

Hatakeyama et al.; "Synthesis and physical properties of polyurethanes from saccharide-based polycaprolactones"; *Macromolecular Symposia*, vol. 130; (1998); pp. 127-138.

Hauss, David J., et al; "Lipid-Based Delivery Systems for Improving the Bioavailability and Lymphatic Transport of a Poorly Water-Soluble $LTB_4$ Inhibitor"; *Journal of Pharmaceutical Sciences*, vol. 87, No. 2; Feb. 1998; pp. 164-169; published online Jan. 7, 1998.

He, Y., et al. "Oral Formulation of a Novel Antiviral Agent, PG301029, in a Mixture of Gelucire 44/14 and DMA (2:1, wt/wt)"; *AAPS Pharm. Sci. Tech.* 6(1); (2005); pp. E1-E5.

Henry, C.; "Sucrose Acetate Isobutyrate Special Grade for Beverage Applications" *International Food Ingred*; (1995); pp. 47-49.

Hoskin PJ, et al; "The bioavailability and pharmacokinetics of morphine after intravenous, oral and buccal administration in healthy volunteers."; *Br J Clin Pharmacol*; 27 (4); (1989); pp. 499-505.

Hülsmann, S., et al; "Melt extrusion—an alternative method for enhancing the dissolution rate of 17β-estradiol hemihydrate"; *European Journal of Pharmaceutics and Biopharmaceutics* 49; (2000); pp. 237-242.

Hyland, J.H., et al.; "Infusion of Gonadotrophin-releasing hormone (GnRH) Induces Ovulation and Fertile Oestrus in Mares During Seasonal Anoestrus"; *J. Reprod. Fert., Suppl*. 35 (1987); pp. 211-220.

Inciardi James A, et al; "Mechanisms of prescription drug diversion among drug-involved club- and street-based populations"; *Pain Medicine*. 8(2), (2007); pp. 171-183.

Irvine, D.S., et al; "Duration of Oestrus and Time of Ovulation in Mares Treated with Synthetic GnRH (Ay24,031)"; *J. Reprod. Fert. Supp*. 23; (1975); pp. 279-283.

Irvine; "GnRH Clinical Application"; *In Equine Reproduction*, (eds) McKinon, A.O. and Voss, J.L., Chapter 36, Lea & Febiger; (1993); pp. 41-45.

Ishida T, Oguri K, et al; "Isolation and identification of urinary metabolites of oxycodone in rabbits"; *Drug Metab Dispos*; 7(3); (1979); pp. 162-165.

Ishida T, Oguri K, Yoshimura H.; "Determination of oxycodone metabolites in urines and feces of several mammalian species"; *J Pharmacobiodyn*; 5(7); (1982); pp. 521-525.

Itoh, K., et al; "Improvement of physiochemical properties of N-4472 part I formulation design by using self-microemulsifying system"; *Int .J. Pharm.*, 238); (2002); pp. 153-160.

Iwanaga, Kazunori, et al; "Disposition of Lipid-Based Formulation in the Intestinal Tract Affects the Absorption of Poorly Water-Soluble Drugs"; *Biol. Pharm. Bull*. vol. 29, No. 3; (2006); pp. 508-512; published online Dec. 5, 2005.

Iyakuhin Tenkabutsu Kenkyykai Ed.; "Jitsuyo Iyakuhin Tenkabutsu (Practical Medical Additives)"; pub. Kagaku Kogyo-sha; Mar. 5, 1974; Tokyo; 6 pages.

Jannin, V., et al; "Systemes auto-émulsionnables et émulsions séches"; *STP Pharma Pratiques*, vol. 15, No. 3; May/Jun. 2005; pp. 246-255.

Jannin, V., et al; "Approaches for the development of solid and semi-solid lipid-based formulations"; *Advanced Drug Delivery Reviews* 60; (2008); pp. 734-746; available online Nov. 4, 2007.

Jöchle, W., et al.; "Control of Ovulation in the Mare with Ovuplant a Short-Term Release Implant (STI) Containing the GnRH Analogue Deslorelin Acetate: Studies from 1990 to 1994"; *Journal of Equine Veterinary Science*, vol. 14m No. 12; (1994); pp. 632-644.

Johnson, et al; "Biodegradable Delivery Systems for Estradiol: Comparison Between Poly(DL-Lactide) Microspheres and the

(56) References Cited

OTHER PUBLICATIONS

Saber Delivery System"; *Proceed. Int'l Symp. Control. Rel. Bioact. Mater.*, 26; Controlled Release Society, Inc.; (1999); 1 page.
Johnson, R.M., et al; "Applications of Continuous Site-Directed Drug Delivery"; *Proc. West Pharmacol Soc.* vol. 45; (2002); pp. 219-222.
Johnston Lloyd D, et al; "Monitoring the future. National results on adolescent drug use: overview of key findings"; (*NIH Publication No. 05-5726*). Bethesda, MD: *National Institute on Drug Abuse*; (2004); pp. 1-66.
Kaiko; "Pharmacology of Tablets of Oxycontin the Development Process Thereof"; *Palliative Care Research* 7(1); (2005); pp. 3-13.
Kale, A., et al; "Design and Evaluation of Self-Emulsifying Drug Delivery Systems (SEDDS) of Nimodipine"; *AAPS Pharm. Sci. Tech.*, 9(1); (2008); pp. 191-196.
Kane, Anil, et al; "A Statistical Mixture Design Approach for Formulating Poorly Soluble Compounds in Liquid Filled Hard Shell Capsules"; *Bulletin Technique Gattefosse* No. 99; (2006); pp. 43-49.
Karatas, A., et al; "Improved solubility and dissolution rate of piroxicam using gelucire 44/14 and labrasol"; *Il Farmaco* 60(9); (2005); pp. 777-782; available online Aug. 9, 2005.
Katz NP, et al.; "Behavioral monitoring and urine toxicology testing in patients receiving long-term opioid therapy" *Anesth Analg.* 97(4); (2003); pp. 1097-1102.
Katz NP, et al; "Development and preliminary experience with an ease of extractability rating system for prescription opioids"; *Drug Development and Industrial Pharmacy*. 32(6); (2006); pp. 727-746.
Katz NP, et al; "Prescription monitoring of medical and non-medical Schedule II opioid abuse in Massachusetts: 1996-2005"; *Conference paper presented at the 69th College on Problems of Drug Dependence (CPDD)*, Quebec, Canada; (2007); 1 page.
Katz NP, et al; "Challenges in the development of prescription opioid abuse-deterrent formulations"; *Clin J Pain*,; 23(8); (2007); pp. 648-660.
King; "Tablets, Capsules, and Pills" Remington's Pharmaceutical Sciences, Ed. Arthur Osol, Chapter 89, (1980); pp. 1553-1584.
Koga, Kenjiro, et al; "In vitro and in situ evidence for the contribution of Labrasol® and Gelucire 44/14 on transport of cephalexin and cefoperazone by rat intestine"; *European Journal of Pharmaceutics and Biopharmaceutics* 54; (2002); pp. 311-318.
Kulkarni, et al., "Polyactic Acid for Surgical Implants," *Arch. Surg.* vol. 93; (1966); pp. 839-843.
Lacoste, D., et al.; "Reversible Inhibition of Testicular Androgen Secretion by 3-, 5- and 6-Month Controlled-Release Microsphere Formulations of the LH-RH Agonist [D-Trp.sup.6, des-Gly-NH.sub.2]LH-RH Ethylamide in the Dog"; *J. Seroid Biochem.* vol. 33, No. 5; (1989); pp. 1007-1011.
Laforet, Jean-Pierre, et al; "The Right Mix"; *Gattefosse*, vol. 7, No. 1; (1995); pp. 1-10.
Lalovic Bojan, et al; "Pharmacokinetics and pharmacodynamics of oral oxycodone in healthy human subjects: role of circulating active metabolites"; *Clin Pharmacol Ther* 79(5); (2006); pp. 461-479.
Larsen, A., et al; "In vitro evaluation of Pharmaceutical surfactants fate during lipolysis and its effects on solubilization of a poorly soluble model compound: Danazol"; *Conference on When Poor Solubility Becomes an Issue: From Early Stage to Proof of Principles*; (2006); Verona (Italy); 2 pages.
Larsen, Anne, et al; "Pharmaceutical Surfactants in Biorelevant Media: Impact on Lipolysis and Solubility of a Poorly Soluble Compound; Danazol"; *Conference, 5th World Meeting on Pharmaceutics Biopharmaceutics and Pharmaceutical Technology*, Geneva, Switzerland; (2006); 2 pages.
Lopez et a;. "Comparative efficacy of two once daily methylphenidate formulations (Ritalin LA and Concerta) and placebo in children with attention deficit hyperactivity disorder across the school day"; *Pediatr Drugs* 5(8); (2003); pp. 545-555.
Lowden, K.; "Filling hard gelatin capsules: experience in a new environment"; *Pharmaceutical Manufacturing Review*, vol. 10, No. 5; (1998); pp. 27-29.

Loy & Hughes "The Effects of Human Chorionic Gonadotrophin on Ovulation, Length of Estrus, and Fertility in the Mare," Cornell Vet. 56:41-50 (1966).
Markowitz et al; "Advances in the pharmacotherapy of attention-deficit-hyperactivity disorder: focus on methylphenidate formulations"; *Pharmacotherapy* 23(10); (2003); pp. 1281-1299.
Markowitz et al; "Pharmacokinetics of methylphenidate after oral administration of two modified-release formulations in healthy adults"; *Clin Pharmacokinet* 42(4); (2003); pp. 393-401.
Material Safety Data Sheet "Eastman: Cellulose Acetate Butyrate CAB-381-2 BP CAB381-20 BP: Coating Chemicals" Eastman Chemical Company, Publication E-296B, Aug. 1994.
Material Safety Data Sheet "Eastman: Cellulose Esters for Pharmaceutical Drug Delivery" Eastman Chemical Company, Publication PCI-105B, Jun. 2004.
Material Safety Data Sheet of Eastman Chemical Products, "SAIB" Sucrose Acetate Isobutyrate, pp. 1-24. Publication GN-311F (Jun. 2004).
Material Safety Data Sheet of Eastman Fine Chemical Pharmaceutical Ingredients, Sucrose Acetate Isobutyrate Special Grade (SAIB-SG), Publication No. EFC-211, (May 1991).
Material Safety Data Sheet of Eastman Products for the Food Industry, "Sucrose Acetate Isbutyrate (SAIB-SB) for Use in Fruit-Flavored Beverages," Publication No. ZM-90, (Sep. 1989); pp. 2-7.
McCabe SE, et al; "Motives, diversion and routes of administration associated with nonmedical use of prescription opioids"; *Addictive Behaviors*. 32; (2007); pp. 562-575.
McCarthy, P.F., et al.; "Management of Stallions on Large Breeding Farms"; *Veterinary Clinics of North America: Equine Practice*, vol. 8, No. 1; Apr. 1992; pp. 219-235.
McKinnon, A.O., et al.; "Effect of GnRH Analogue (Ovuplant), hCG and Dexamethasone on Time to Ovulation in Cycling Mares"; *World Equine Veterinary Review*, vol. 2: No. 3; (1997); pp. 16-18.
McKinnon, A.O., et al.; "Repeated Use of a GnRH Analogue Deslorelin (Ovuplant) for Hastening Ovulation in the Transitional Mare"; *Equine Veterinary Journal* 29 (2); (1996); pp. 153-155.
McLellan AT, et al; An improved diagnostic instrument for substance abuse patients—The Addiction Severity Index: *The Journal of Nervous and Mental Disease*. vol. 168, No. 1; (1980); pp. 26-33.
Mearns, D.; "Changing Seasons"; *The Blood-Horse*; Sep. 28, 1996; pp. 4794-4765.
Meehan, E., et al; "Monitoring the stability of excipients used in lipid matrix formulations"; (*Poster Abstract*), *Conference "33rd Annual Meeting of the Controlled Release Society"*, Vienna, Austria. Jul. 22, 2006; 2 pages.
Mehuys, E., et al; "Human bioavailability of propranolol from a matrix-in-cylinder system with a HPMC-Gelucire® core"; *Journal of Controlled Release* 107; (2005); pp. 523-536; available online Aug. 1, 2005.
Merrifield, Bruce; "Solid Phase Synthesis"; *Science*, vol. 232; Apr. 18, 1986; pp. 341-347.
Meyer RJ, Hussain AS. Awareness topic: mitigating the risk of ethanol induced dose dumping from oral sustained/controlled release dosage forms. In: FDA's Advisory Committee for Pharmaceutical Science Meeting, Oct. 2005; pp. 1-4.
Montovan, S.M., et al; "The Effect of a Potent GnRH Agonist on Gonadal and Sexual Activity in the Horse"; *Theriogenology*, vol. 33 No. 6; Jun. 1990; pp. 1305-1321.
Mumford, E.L.; "Use of Deslorelin Short-Term Implants to Induce Ovulation in Cycling Mares During Three Consecutive Estrous Cycles"; *Animal Reproduction Science*, vol. 39; (1995); pp. 129-140.
Murray Sally, et al; "Alcohol-associated rapid release of a long-acting opioid"; *CAMJ*;173(7); Sep. 27, 2005; pp. 756.
Nabors, et al; "Controlled Release of Diclofenac-Na from Cellulose Ester Microspheres"; *PDD Presentation 7481 at the 1994 Ninth Annual AAPS Meeting in San Diego, CA*; Nov. 6-10, 1994; 2 pages.
Nakagaki, Arita; "Seizai Butsuri Kagaku (Physical Chemistry of Medical Preparations)", *pub. Asakura Shoten*; Nov. 5, 1968; Tokyo; 6 pages.
Nally, J., et al.; "Induction of Mucosal *IgA* Specific for SeMF3 for *Streptococcus equi* with Intranasal Vaccination Using a Sucrose

(56) References Cited

OTHER PUBLICATIONS

Acetate Isobutyrate Based Delivery System", *Proceed. Int'l. Symp. Control. Rel. Bioact. Mater.*, 26; (1999); Controlled Release Society, Inc. 2 pages.
Nett, T.M., et al.; "Further Studies on the Radioimmunoassay of Gonadotropin-releasing Hormone: Effect of Radioiodination, Antiserum and Unextracted Serum on Levels of Immunoreactivity in Serum"; *Endocrinology* vol. 101, No. 4, (1977); pp. 1135-1144.
O'Driscoll, Caitriona M.; "Lipid-based formulations for intestinal lymphatic delivery"; *European Journal of Pharmaceutical Sciences* 15; (2002); pp. 405-415.
Okumu, et al; "Evaluation of SABER™ as a Local Delivery System for rhVEGF-Formulation Design and In Vitro Assessment" *Genentech, Inc., South San Francisco, CA USA and Southern BioSystems, Inc.* Birmingham AL, USA; (2000); 1 page.
Okumu, et al; "Evaluation of SABER™ as a Local Delivery System for rhVEGF-Formulation Design and In Vitro Assessment" *Genentech, Inc., South San Francisco, CA USA and Southern BioSystems, Inc.* Birmingham AL, USA. Poster; (2001); 1 page.
Patel, Pranav, et al; "Preparation, Evaluation and Comparison of Lipid Based Drug Delivery Systems of Tacrolimus"; *International Journal of Pharmacy and Pharmaceutical Sciences*, vol. 6 Suppl 2; (2014); pp. 588-591.
Patrick et al; "New methylphenidate formulations for the treatment of attention-deficit/hyperactivity disorder" *Expert Opin Drug Deliv* 2(1); (2005); pp. 121-143.
Pelham et al; "Once-a-day Concerta methylphenidate versus three-times-daily methylphenidate in laboratory and natural settings"; *Pediatrics* vol. 107, No. 6; Jun. 6, 2001; pp. 1-15.
Perissutti, B.; et al; "Solid dispersions of carbamazepine with Gelucire 44/14 and 50/13"; *S.T.P. Pharma Sciences* 10(6); (2000); pp. 479-484.
Pozzi, Franco, et al; "Formulations of Ubidecarenone with Improved Bioavailability"; *Eur. J. Pharm. Biopharm*, vol. 37, No. 4; (1991); pp. 243-246.
Pulido et al.; "Enzymatic Regioselective Acylation of Hexoses and Pentoses Using Oxime Esters"; *J. Chem. Soc. Perkin Trans.* 1, (21); (1992); pp. 2891-2898.
Rabb et al.; "Effects of Active Immunication Against GnRH on LH, FSH and Prolactin Storage, Sectretion and Response to Their Secretagogues in Pony Geldings"; *J Anim. Sci.*, 68; (1990); pp. 3322-3329.
Ren, Shan, et al; "In Vitro Metabolic Stability of Moisture-Sensitive Rabeprazole in Human Liver Microsomes and Its Modulation by Pharmaceutical Excipients"; *Arch Pharm Res* vol. 31, No. 3; (2008); pp. 406-413; published online Apr. 13, 2008.
Reynolds, R.C. et al.; "Sucrose acetate isobutyrate (SAIB): historical aspects of its use in beverages and a review of toxicity studies prior to 1988"; *Food Chem. Toxicol*.36(2), (1998); pp. 81-93.
Reynolds, R.C.; "Metabolism and pharmacokinetics of sucrose acetate isobutyrate (SAIB) and sucrose octaisobutyrate (SOIB) in rats, dogs, monkeys or humans: a review"; *Food Chem. Toxicol.*, 36 (2); (1998); pp. 95-99.
Robinson; "Coating of Pharmaceutical Dosage Forms" *Remington's Pharmaceutical Sciences*, Ed. Arthur Osol, Chapter 90; (1980); pp. 1585-1593.
Roser, J.J., et al.; "The Development of Antibodies to Human Chorionic Gonadotrpins Following its Repeated Injection in the Cyclic Mare"; *J. Reprod. Fert Suppl.*, (1979); pp. 173-179.
Roussin, P. et al; "Gelucire® 44/14; A High-Performance System to Enhance Bioavailability of Poorly Water Soluble Drugs"; *Bulletin Technique Gattefosse*, No. 90; (1997); pp. 51-58.
Sachs-Barrable, K., et al; "Lipid Excipients Peceol and Gelucire 44/14 decrease P-glycoprotein mediated efflux of Rhodamine 123 partially due to modifying P-glycoprotein expression within Caco-2 Cells."; *J. Pharm. Pharm. Sci.*, 10(3); (2007); pp. 319-331.
Saeki; "Progress of Orally Opiate Analgesics and Non-Steroidal Anti-Flammatory Agent" *Drug Deliv Syst* 20(5); (2005) pp. 521-529.
Santus et al.; "Osmotic Drug Delivery: A Review of the Patent Liter" *J Control Release* 35(1); (1995); pp. 1-21.
Schamp, Karen, et al; "Development of an in vitro/in vivo correlation for lipid formulations of EMD 50733, a poorly soluble, lipophilic drug substance"; *European Journal of Pharmaceutics and Biopharmaceutics* 62; (2006); pp. 227-234; available online Oct. 24, 2005.
Serajuddin, Abu T.M., et al; "Effect of Vehicle Amphiphilicity on the Dissolution and Bioavailability of a Poorly Water-Soluble Drug from Solid Dispersions"; *Journal of Pharmaceutical Sciences*, vol. 77, No. 5, May 1988; pp. 414-417.
Serajuddin, Abu T.M., et al; "Water Migration from Soft Gelatin Capsule Shell to Fill Material and Its Effect on Drug Solubility"; *Journal of Pharmaceutical Sciences*, vol. 75, No. 1; Jan. 1986; pp. 62-64.
Sethia, Sundeep, et al; "Physicochemical Characterization of Solid Dispersions of Carbamazepine Formulated by Supercritical Carbon Dioxide and Conventional Solvent Evaporation Method"; *Journal of Pharmaceutical Sciences*, vol. 91, No. 9; Sep. 2002; pp. 1948-1957.
Sethia, Sundeep, et al; "In Vitro-In Vivo Evaluation of Supercritical Processed Solid Dispersions: Permeability and Viability Assessment in Caco-2 Cells"; *Journal of Pharmaceutical Sciences*, vol. 93, No. 12; Dec. 2004; pp. 2985-2993; published online Oct. 1, 2004.
Shah, N. H; et al; "Self-Emulsifying Drug Delivery Systems (SEDDS) for Improving In Vitro Dissolution and Oral Absorption of Lipophilic Drugs"; *Bulletin Technique. Gattefossé Report*, No. 85; (1992/1993); pp. 45-54.
Sheen, Pai-Chang, et al; "Bioavailability of a Poorly Water-Soluble Drug from Tablet and Solid Dispersion in Humans"; *Journal of Pharmaceutical Sciences*, vol. 80, No. 7; Jul. 1991; pp. 712-714.
Shimpi Shyam, et al; "Preparation and Evaluation of Diltiazem Hydrochloride-Gelucire 43/01 Floating Granules Prepared by Melt Granulation"; *AAPS PharmSciTech* 5(3), Article 43; (2004); pp. 1-6; (http://www.aapspharmscitech.org).
Smith & Tipton (1996) "A Novel Parental Delivery System" *AAPS Presentation PDD 7270*, Seattle, WA; (1996) Annual Meeting; 2 pages.
Soliman, M. S., et al; "Preparation and in vitro characterization of a semi-solid dispersion of flurbiprofen with Gelucire 44/14 and Labrasol"; *Pharmazie* 60(4); (2005); pp. 288-293.
Srinivas et al.; "Enantioselective pharmacokinetics and pharmacodynamics of dl-threo-methylphenidate in children with attention deficit hyperactivity disorder"; *Clin Pharmacal Ther* 52(5); (1992); pp. 561-568.
Stegemann. S., et al; "When Poor Solubility Becomes an Issue: From Early Stage to Proof of Concept"; *European Journal of Pharmaceutical Sciences* 31; (2007); pp. 249-261.
Strickley, Robert G; "An Overview of Lipid Excipients Currently Available: Strengths, Weaknesses and Opportunity Gaps: The Options for the Formulator"; *Bulletin Technique Gattefosse*, No. 100; (2007); pp. 31-37.
Strickley, Robert G.; "Solubilizing Excipients in Oral and Injectable Formulations"; *Pharmaceutical Research*, vol. 21, No. 2; Feb. 2004; pp. 201-230.
Subramanian, Ramaswamy, et al; "Effect of Lipid Excipients on In Vitro Pancreatic Lipase Activity"; *Drug Development and Industrial Pharmacy*, vol. 29, No. 8; (2003); pp. 885-890.
Sucrose Acetate Isobutyrate, 21 CFR 172.831 (1999).
Sullivan, et al; "Delivery of Taxol® and other Antineoplastic Agents from a Novel System Based on Sucrose Acetate Isobutyrate" *AAPS Boston, MA. Southern BioSystems, Inc.* Birmingham AL, USA (1997); 2 pages.
Sullivan, et al; "Sustained Release of Orally Administered Active Using SABER Delivery System Incorporated into Soft Gelatin Capsules"; *Proceed. Int'l. Control. Rei. Bioact. Mater. Controlled Release Society.* vol. 25; Jun. 1998 Las Vegas NV; pp. 918-919.
Sullivan, et al; "Sustained Release of Progesterone and Estradiol from the SABER™ Delivery System: In Vitro and In Vivo Release Rates" *CRS Las Vegas, NV. Southern BioSystems, Inc.* Birmingham AL, USA; (1998); 2 pages.

(56) References Cited

OTHER PUBLICATIONS

Sullivan, et al; "Sustained Release of Lysozyme from the SABER™ Delivery System" *AAPS, New Orleans, LA. Southern BioSystems, Inc.* Birmingham AL, USA; (1999); 2 pages.
Sullivan, et al. (1998) "Sustained Release of Bupivacaine from the SABER TM Delivery System" AAPS, San Francisco, CA. Southern BioSystems, Inc. Birmingham AL, USA.
Sullivan, et al; "Incorporation of Polymer Microparticles Into Sucrose Acetate Isobutyrate Reduces Burst and Extends Release" *Proceed Int'l Symp. Control. Rel. Bioact. Mater., 27, Controlled Release Society, Inc.* Paris, France; Jul. 7-13, 2000.
Sullivan, J. J., et al.; "Duration of Estrus and Ovulation Time in Nonlactating Mares Given Human Chorionic Gonadotropin During Three Successive Estrous Periods"; *J.A.V.M.A.*, vol. 162, No. x; May 15, 1973; pp. 895-898.
Svensson, A., et al; "Hydration of an amphiphilic excipient Gelucire® 44/14"; *Int. J. Pharm.* 281(1-2); (2004); pp. 107-118.
Swanson et al; "Objective and subjective measures of the pharmacodynamic effects of Adderall in the treatment of children with ADHD in a controlled laboratory classroom setting"; *Psychopharmacol Bull* 34(1); (1998); pp. 55-60.
Swanson et al; "Acute tolerance to methylphenidate in the treatment of attention deficit hyperactivity disorder in children" *Clin Pharmacal Ther* 66(3); (1999); pp. 295-305.
Swanson et al. Ritalin: Theory and Practice. 2nd Edition, Greenhill & Osman Ed., Mary Ann Liebert, Larchmont, NY; (1999) pp. 405-430.
Swanson et al; "Efficacy of a new pattern of delivery of methylphenidate for the treatment of ADHD: effects on activity level in the classroom and on the playground" *J Am Acad Child Adolesc Psychiatry* 41(11); (2002); pp. 1306-1314.
Swanson et al; "Pharmacokinetic and pharmacodynamic properties of stimulants: implications for the design of new treatments for ADHD"; *Behav Brain Res* 130(1-2); (2002); pp. 73-78.
Swanson et al; "Development of a new once-a-day formulation of methylphenidate for the treatment of attention-deficit/hyperactivity disorder: proof-of-concept and proof-of-product studies"; *Arch Gen Psychiatry* 60(2); (2003); pp. 204-211.
Swanson et al; "Serum and brain concentrations of methylphenidate: implications for use and abuse"; *Neurosci Biobehav Rev* 27(7); (2003); pp. 615-621.
Swanson et al; "A comparison of once-daily extended-release methylphenidate formulations in children with attention-deficit/hyperactivity disorder in the laboratory school (the Comacs Study)"; *Pediatrics* 113(3 Pt. 1); (2004); pp. e206-e216.
Swiderski et al.; "Application of 14C Isotope in Studies on the Lability of Sugar Substituents" *Nukleonika, Supl.*, vol. 10; (1966); pp. 347-352.
Tashtoush, Bassam M., et al.; "In Vitro and In Vivo Evaluation of Glibenclamide in Solid Dispersion Systems"; *Drug Development and Industrial Pharmacy*, vol. 30, No. 6; (2004); pp. 601-607.
Thompson, D. L., et al., "Effects of Melatonin and Thyrotropin Releasing Hormone on Mares During the Nonbreeding Season", Journal of Animal Science, vol. 56, No. 3, (1983), pp. 668-677.
Thompson, D. L., et al., "Testosterone Effects on Mares During Synchronization with Altrenogest: FHS, LH, Estrous Duration and Pregnancy Rate"; *Journal of Animal Science*, vol. 56, No. 3; (1983); pp. 678-686.
Tipton; "Peptide Delivery from an In Situ Gelling System Based lon Sucrose Acetate Isobutyrate" *AAPS J Abstract. Southern BioSystems, Inc.* Birmingham AL, USA; (1999); 1 page.
Tipton, "In Situ Gelling Systems"; Sustained-Release Injectable Products, Ed. Senior & Radomsky, Interpharm Press, Denver, CO; (2000); pp. 258-259.

Tipton, et al; "Local Delivery from a Novel Biodegradable in Situ Delivery System"; *Sixth World Biomaterials Congress, Kamuela, HI,. Southern BioSystems, Inc.* Birmingham AL, USA, May 15-20, 2000; 1 page.
Tran, Thao Truong-Dinh; et al; "Dissolution-modulating mechanism of alkalizers and polymers in a nanoemulsifying solid dispersion containing ionizable and poorly water-soluble drug"; *European Journal of Pharmaceutics and Biopharmaceutics* 72; (2009); pp. 83-90; available online Dec. 25, 2008.
Trescot AM, et al; "Opioid Guidelines in the Management of Chronic Non-Cancer Pain." *Pain Physician*, vol. 9; (2006), pp. 1-40.
U.S. Department of Health and Human Services "Guidance for Industry: Food-Effect Bioavailability and Fed Bioequivalence Studies" FDA, Center for Drug Evaluation and Research (CDER), Dec. 2002.
U.S. Appl. No. 12/754,486, filed Apr. 5, 2010, 103 pages; with Preliminary Amendment filed Nov. 23, 2010, 13 pages.
U.S. Appl. No. 60/434,839, filed Dec. 18, 2002, 111 pages.
Vega-Rios Aracelly, et al; "Acid-catalyzed hydrolysis of triacylglycerols obeys monoexponential kinetics."; *International Journal of Chemical Kinetics*, vol. 24; (1992); pp. 887-894.
Venkatesan, N. et al; "Gelucire® 44/14 and Labrasol® in Enhancing Oral Absorption of Poorly Absorbable Drugs"; *Bulletin Technique Gattefosse*, No. 99; (2006); pp. 79-88.
Vila Jato, J.L., et al; "Influence of melting point and HLB on the release of amoxicillin from granulates containing Gelucire as excipients"; *S.T.P. Pharma*, vol. 6, No. 5; (1990); pp. 287-292.
Volkow et al; "Relationship between psychostimulant-induced "high" and dopamine transporter occupancy"; *Proc Natl Acad Sci USA* 93(19); (1996); pp. 10388-10392.
Volkow et al. "Temporal relationships between the pharmacokinetics of methylphenidate in the human brain and its behavioral and cardiovascular effects"; *Psychopharmacology* 123; (1996) pp. 26-33.
Volkow et al; "Methylphenidate and cocaine have a similar in vivo potency to block dopamine transporters in the human brain"; *Life Sciences* vol. 65, No. 1; (1999); PL7-PL12.
Volkow et al; "Relationship between blockade of dopamine transporters by oral methylphenidate and the increases in extracellular dopamine: therapeutic implications"; *Synapse* 43(3); (2002); pp. 181-187.
Volkow, et al; "Dopamine transporter occupancies in the human brain induced by therapeutic doses of oral methylphenidate"; *Am J Psychiatry* 155(10); (1998); pp. 1325-1331.
Voss, J.L., et al; "The Effect of HCG on Duration of Oestrus, Ovulation Time and Fertility in Mares"; *Journal of Reprod. Fert., Suppl.* 23; (1975); pp. 297-301.
Wigal et al; "Reliability and validity of the SKAMP rating scale in a laboratory school setting" *Psychopharmacol Bulletin*, vol. 34, No. 1; (1998); pp. 47-53.
Wigal et al; "Selection of the Optimal Dose Ratio for a Controlled-Delivery Formulation of Methylphenidate"; *The Journal of Applied Research* 3; (2003); pp. 46-63.
Wightman et al; "Transient changes in mesolimbic dopamine and their association with 'reward'"; *Journal of Neurochemistry* 82(4); (2002); pp. 721-735.
Wolraich et al; "Randomized, controlled trial of oros methylphenidate once a day in children with attention-deficit/hyperactivity disorder"; *Pediatrics* 108(4); (2001); pp. 883-892.
Yüksel, Nilüfer, et al; "Enhanced bioavailability of piroxicam using Gelucire 44/14 and Labrasol: in vitro and in vivo evaluation"; *European Journal of Pharmaceutics and Biopharmaceutics* 56; (2003); pp. 453-459.
U.S. Appl. No. 15/486,119, filed Apr. 12, 2017, Yum, et al.

\* cited by examiner

ORAL PHARMACEUTICAL DOSAGE FORMS

CROSS REFERENCE TO RELEVANT APPLICATIONS

This application is a continuation of U.S. application Ser. No. 14/791,073, filed 2 Jul. 2015, now U.S. Pat. No. 9,616,055, which application is a continuation of U.S. application Ser. No. 13/924,232, filed 21 Jun. 2013, which application is a continuation of U.S. application Ser. No. 12/590,195, filed 3 Nov. 2009, which application claims the priority entitlement and full benefit of U.S. Provisional Application Nos. 61/198,244, filed 3 Nov. 2008, and 61/201,015, filed 5 Dec. 2008.

FIELD OF THE INVENTION

The invention relates to oral pharmaceutical dosage forms and the use thereof. More specifically, this invention relates to controlled release oral pharmaceutical dosage forms and their use to deliver methylphenidate.

BACKGROUND

Formulation of drugs for delivery, particularly oral delivery, poses certain challenges. One challenge is to produce an oral controlled-release dosage form that provides for a relatively steady dose of drug over the approximately eight hours during which the dosage form passes through the gastrointestinal tract. Sustained release is often achieved by providing the tablet with a coating that delays release, or by formulating the tablet in such a way that it disintegrates relatively slowly, releasing drug as it does so. A tablet, however, once ingested, is subject to considerable mechanical and chemical stresses as it passes through the esophagus, stomach, duodenum, jejunum, ileum, large intestine and colon, thus providing a significant challenge in maintaining controlled release of the drug formulation. Acids, enzymes and peristalsis can cause the tablet to break apart, resulting in exposure of the inside of the tablet and an increase in surface area of the tablet material. This will tend to increase the delivery rate of the drug or otherwise adversely affect the controlled release properties of the dosage form.

Another challenge is to produce a dosage form, including an oral dosage form, that reduces the potential for drug abuse. In particular, opioids, CNS-depressants, and stimulants are commonly abused. According to a 1999 study by the National Institute on Drug Abuse (NIDA), an estimated 4 million people, about 2 percent of the population age 12 and older, were (at the time of the study) using prescription drugs "non-medically."

While many prescription drugs can be abused, the most common classes of abused drugs are: (1) Opioids—often prescribed to treat pain, (2) CNS Depressants—used to treat anxiety and sleep disorders, and (3) Stimulants—prescribed to treat narcolepsy and attention deficit/hyperactivity disorder.

Stimulants are a class of drugs that enhance brain activity—they cause an increase in alertness, attention, and energy that is accompanied by increases in blood pressure, heart rate, and respiration. Stimulants are frequently prescribed for treating narcolepsy, attention-deficit hyperactivity disorder (ADHD), and depression. Stimulants may also be used for short-term treatment of obesity, and for patients with asthma. Stimulants such as dextroamphetamine (Dexedrine™) and methylphenidate (Ritalin™) have chemical structures that are similar to key brain neurotransmitters called monoamines, which include norepinephrine and dopamine. Stimulants increase the levels of these chemicals in the brain and body. This, in turn, increases blood pressure and heart rate, constricts blood vessels, increases blood glucose, and opens up the pathways of the respiratory system.

The abuse of stimulants has been a growing problem. Over 1.4 million Americans over 12 years old reported abusing stimulants. 2004 National Survey on Drug Use & Health, SAMHSA, U.S. Department of HHS. Twenty-nine percent (29%) of all prescribed stimulants are diverted to someone other than the patient. Stimulants are typically abused in two distinct ways. In one way, prescribed drugs are sold or diverted to individuals who ingest the oral formulations at or around a typical daily dose to promote wakefulness or to increase performance and concentration at a specific time, such as when studying for or taking exams. Stimulants also give rise to euphoria and liking when rapidly absorbed. Abusers in search of this effect are likely to take a much large than normal oral dose, or to extract the active agent (stimulant drug) from the formulation and, after grinding, inhale the resulting powder. A further mechanism of abuse is the extraction of the stimulant drug from the rest of the formulation, dissolution and then injection. 80% of substance abusers use short acting (i.e., immediate release) formulations for ease of availability and in extraction of the stimulant drug. While oral administration of stimulants is the preferred route for abuse, forty percent (40%) of abusers have taken stimulant drugs by grinding and then inhaling. Only a small number of abusers inject stimulant drugs.

A common and particularly dangerous cocktail of drugs is produced when stimulants are mixed with antidepressants or over-the-counter cold medicines containing decongestants. Anti-depressants may enhance the effects of a stimulant, and stimulants in combination with decongestants may cause blood pressure to become dangerously high or lead to irregular heart rhythms, which in extreme cases may be fatal.

Solid dosage forms are particularly susceptible to abuse. For example, tablets for oral drug delivery can be ground down into a powder. Drug addicts and abusers grind down the tablet in order to nasally inhale the drug. Addicts also grind the tablet to extract the drug into alcohol or water to make a concentrated injectable drug solution. Administration of various abused drugs in this way produces a sudden high dose of drug into the blood stream making the user euphoric. These well-known techniques for drug abuse have been used for many years with all manner of drugs.

Attention Deficit Disorders are the most common psychiatric disorders in children with reported rates ranging from 4% to 9%. Attention Deficit Disorder (ADD) is characterized by inattention and impulsivity and may be present with hyperactivity (ADHD). Other characteristics may include aggressiveness, stealing, lying, truancy, setting fires, running away, explosiveness, cognitive and learning problems as well as poor social skills. It is four to five times more frequent in boys than girls.

Stimulant medication, such as amphetamines, have been shown to be the most effective agents in the treatment of children with disorders of activity modulation and attention regulation and result in significant improvement in 70 to 80 percent of affected children. Positive effects of stimulants have been documented in a variety of areas including behavioral, social, perceptual performance, motor activity, impulse control, attention regulation and cognitive performance.

Methylphenidate {dl-threo-methyl-2-phenyl-2-(2-piperidyl) acetate} is the psychostimulant used most frequently in the treatment of hyperactivity and attention deficit disorder. It appears to have a higher incidence of positive effects and a lower incidence of adverse effects than other psychostimulants. The efficacy of methylphenidate ("MPH") in improving attention and behavioral symptoms has been supported by many studies.

SUMMARY OF THE INVENTION

Controlled release oral pharmaceutical dosage forms that include methylphenidate and a controlled release carrier system are provided. It is thus a primary object of the present invention to provide a controlled release oral dosage form that includes methylphenidate and a controlled release carrier system. The dosage form is characterized by providing:

(i) an initial increasing in vivo rate of release of methylphenidate from the controlled release system suitable to provide an initial increasing-rate phase of less than or equal to about 2 hours, and sufficient to provide a therapeutically effective amount of methylphenidate for a rapid onset of action;

(ii) a second, non-ascending in vivo rate of release of methylphenidate from the controlled release system that provides a subsequent non-ascending phase sufficient to provide a therapeutically effective amount of methylphenidate through at least about 11 to 12 hours post administration; and (iii) a single $T_{max}$ of about 5.5 to 7.5 hours post administration. In related objects of the invention, the above-described controlled release oral dosage forms are further characterized as follows: (a) where the initial increasing-rate phase is sufficient to provide an onset of action within about 1 to 1.5 hours post administration; (b) where the single $T_{max}$ occurs at about 6 to 7 hours post administration; and (c) where the subsequent non-ascending phase is sufficient to provide a therapeutically effective amount of methylphenidate through at least about 12 to 14 hours post administration. In further related objects of the invention, the above-described controlled release oral dosage forms are further characterized by having a food effect, such as wherein oral bioavailability of the methylphenidate form the dosage form is increased upon co-administration with food and/or wherein the rate of absorption of methylphenidate is decreased and the extent of absorption of methylphenidate is increased upon co-administration with food. In the practice of the invention, the controlled release (CR) carrier system can be selected from an Osmotic CR carrier system, a Liquid CR carrier system, a Particulate CR carrier system, a CR Matrix carrier system, or a CR Melt-Extrusion Matrix carrier system. In addition, in certain preferred embodiments, the controlled release oral dosage form is abuse-resistant. In such cases, the abuse-resistant controlled release oral dosage forms of the invention can be characterized as follows: (a) the controlled release carrier system provides a decreased risk of misuse or abuse; (b) the abuse-resistant controlled release oral dosage provides a decreased risk of misuse or abuse characterized by a low in vitro solvent extractability value of the methylphenidate from the dosage form; (c) the abuse-resistant controlled release oral dosage provides a decreased risk of misuse or abuse characterized by the absence of any significant effect on absorption of the active agent from the dosage form upon co-ingestion of the dosage form and alcohol by a subject; (d) the abuse-resistant controlled release oral dosage provides a decreased risk of misuse or abuse characterized by a low injectability potential; and/or (e) the abuse-resistant controlled release oral dosage provides a decreased risk of misuse or abuse characterized by the dosage form is not susceptible to common forms of abuse comprising injection, inhalation (crushing and sniffing) and volatilization (smoking). Any of the above-described abuse-resistant controlled release oral dosage forms can be further characterized wherein the controlled release carrier system includes a high viscosity liquid carrier material (HVLCM). The controlled release oral dosage forms (whether or not abuse-resistant) provide unique in vivo release kinetics such that the initial increasing-rate phase and subsequent non-ascending phase are sufficient to provide the methylphenidate in vivo PK profile depicted in FIG. 7 when the dosage form is administered to a subject. It is a further related object of the invention to provide a method of treating Attention Deficit Disorder (ADD) or Attention Deficit Hyperactivity Disorder (ADHD) in a subject, where the method comprises administering the controlled release oral dosage form of the invention to the subject on a once-day (QD) basis.

It is also a primary object of the present invention to provide an abuse-resistant controlled release oral dosage form that includes methylphenidate and a controlled release carrier system. The abuse-resistant dosage form is characterized by providing:

(i) an initial increasing in vivo rate of release of methylphenidate from the controlled release system suitable to provide an initial increasing-rate phase of less than or equal to about 2 hours, and sufficient to provide a therapeutically effective amount of methylphenidate for a rapid onset of action;

(ii) a second, non-ascending in vivo rate of release of methylphenidate from the controlled release system that provides a subsequent non-ascending phase sufficient to provide a therapeutically effective amount of methylphenidate through at least about 11 to 12 hours post administration; and (iii) a single $T_{max}$ of about 5.5 to 7.5 hours post administration, wherein the controlled release carrier system includes an HVLCM, a network former and at least one viscosity enhancing agent. In related objects of the invention, the above-described abuse-resistant controlled release oral dosage forms are further characterized as follows: (a) where the initial increasing-rate phase is sufficient to provide an onset of action within about 1 to 1.5 hours post administration; (b) where the single $T_{max}$ occurs at about 6 to 7 hours post administration; and (c) where the subsequent non-ascending phase is sufficient to provide a therapeutically effective amount of methylphenidate through at least about 12 to 14 hours post administration. It further related objects of the invention, the above-described abuse-resistant controlled release oral dosage forms are further characterized by having a food effect, such as wherein oral bioavailability of the methylphenidate form the dosage form is increased upon co-administration with food and/or wherein the rate of absorption of methylphenidate is decreased and the extent of absorption of methylphenidate is increased upon co-administration with food. The abuse-resistant controlled release oral dosage forms of the invention can be further characterized as follows: (a) the controlled release carrier system provides a decreased risk of misuse or abuse; (b) the abuse-resistant controlled release oral dosage provides a decreased risk of misuse or abuse characterized by a low in vitro solvent extractability value of the methylphenidate from the dosage form; (c) the abuse-resistant controlled release oral dosage provides a decreased risk of misuse or abuse characterized by the absence of any significant effect on absorption of the active agent from the dosage form upon co-ingestion of the dosage form and alcohol by a subject; (d) the abuse-resistant controlled release oral dosage provides a decreased risk of misuse or abuse characterized by a low injectability potential; and/or (e) the abuse-resistant controlled release oral dosage provides a decreased risk of misuse or abuse characterized by the dosage form is not susceptible to common forms of abuse comprising injection, inhalation (crushing and sniffing) and volatilization (smoking). In each of the above-described related objects of the invention, the controlled release carrier system can be further characterized by a unique set of pharmaceutical excipients including solvents, carrier materials, network formers and viscosity enhancing agents. The abuse-resistant controlled release oral dosage forms provide unique in vivo release kinetics such that the initial increasing-rate phase and subsequent non-ascending phase are sufficient to provide the methylphenidate in vivo PK profile depicted in FIG. 7 when the dosage form is administered to a subject. It is a further related object of the invention to provide a method of treating Attention Deficit Disorder (ADD) or Attention Deficit Hyperactivity Disorder (ADHD) in a subject, where the method comprises administering the abuse-resistant controlled release oral dosage form of the invention to the subject on a once-day (QD) basis.

It is a still further primary object of the present invention to provide an abuse-resistant controlled release oral dosage form that includes methylphenidate and a controlled release carrier system. The abuse-resistant dosage form is characterized by providing:

(i) an initial increasing in vivo rate of release of methylphenidate from the controlled release system suitable to provide an initial increasing-rate phase of less than or equal to about 2 hours, and sufficient to provide a therapeutically effective amount of methylphenidate for a rapid onset of action;

(ii) a second, non-ascending in vivo rate of release of methylphenidate from the controlled release system that provides a subsequent non-ascending phase sufficient to provide a therapeutically effective amount of methylphenidate through at least about 11 to 12 hours post administration; and (iii) a single $T_{max}$ of about 5.5 to 7.5 hours post administration, wherein the controlled release carrier system includes an HVLCM, a network former, a rheology modifier and a hydrophilic agent. In related objects of the invention, the above-described abuse-resistant controlled release oral dosage forms are further characterized as follows: (a) where the initial increasing-rate phase is sufficient to provide an onset of action within about 1 to 1.5 hours post administration; (b) where the single $T_{max}$ occurs at about 6 to 7 hours post administration; and (c) where the subsequent non-ascending phase is sufficient to provide a therapeutically effective amount of methylphenidate through at least about 12 to 14 hours post administration. It other related objects of the invention, the above-described abuse-resistant controlled release oral dosage forms are further characterized by having a food effect, such as wherein oral bioavailability of the methylphenidate form the dosage form is increased upon co-administration with food and/or wherein the rate of absorption of methylphenidate is decreased and the extent of absorption of methylphenidate is increased upon co-administration with food. The abuse-resistant controlled release oral dosage forms of the invention can be further characterized as follows: (a) the controlled release carrier system provides a decreased risk of misuse or abuse; (b) the abuse-resistant controlled release oral dosage provides a decreased risk of misuse or abuse characterized by a low in vitro solvent extractability value of the methylphenidate from the dosage form; (c) the abuse-resistant controlled release oral dosage provides a decreased risk of misuse or abuse characterized by the absence of any significant effect on absorption of the active agent from the dosage form upon co-ingestion of the dosage form and alcohol by a subject; (d) the abuse-resistant controlled release oral dosage provides a decreased risk of misuse or abuse characterized by a low injectability potential; and/or (e) the abuse-resistant controlled release oral dosage provides a decreased risk of misuse or abuse characterized by the dosage form is not susceptible to common forms of abuse comprising injection, inhalation (crushing and sniffing) and volatilization (smoking). In each of the above-described related objects of the invention, the controlled release carrier system can be further characterized by a unique set of pharmaceutical excipients including solvents, carrier materials, network formers and viscosity enhancing agents. The abuse-resistant controlled release oral dosage forms provide unique in vivo release kinetics such that the initial increasing-rate phase and subsequent non-ascending phase are sufficient to provide the methylphenidate in vivo PK profile depicted in FIG. 7 when the dosage form is administered to a subject. It is a further related object of the invention to provide a method of treating Attention Deficit Disorder (ADD) or Attention Deficit Hyperactivity Disorder (ADHD) in a subject, where the method comprises administering the abuse-resistant controlled release oral dosage form of the invention to the subject on a once-day (QD) basis.

It is an advantage of the present invention that the controlled release oral dosage forms provide enhanced delivery kinetics of methylphenidate. It is also an advantage of the present invention that the abuse-resistant controlled release oral dosage forms are able to provide enhanced safety features and/or abuse-resistance properties in addition to enhanced in vivo pharmacological performance as compared with prior dosage forms. It is a further advantage of the invention that the inventive dosage forms can be readily constructed and used to provide a wide range of safer and more efficacious pharmacological solutions to the medical field. These and other objects, aspects and advantages of the present invention will readily occur to the skilled person upon reading the instant disclosure and specification.

BRIEF DESCRIPTION OF THE FIGURES

FIG. 10A depicts the cumulative release profiles obtained in the study and compares them with cumulative release data presented in the U.S. Pat. No. 6,919,373; and FIG. 10B depicts the cumulative release in vitro results obtained in the study plotted against input in vivo obtained via deconvolution (open symbols) for both Metadate CD and Concerta.

FIGS. 16A and 16B show the mean dissolution data results from the in vitro dissolution study of MPH1-MPH3 and MPH11-MPH13 Test Capsules as described in Example 2a.

DETAILED DESCRIPTION

Before describing the present invention in detail, it is to be understood that this invention is not limited to particularly exemplified carrier materials or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby expressly incorporated by reference in their entirety.

It must be noted that, as used in this specification and the appended claims, the singular forms "a," "an" and "the" include plural referents unless the content clearly dictates otherwise. Thus, for example, reference to "a non-polymeric carrier material" includes a mixture of two or more such carrier materials, reference to "a solvent" includes a mixture of two or more such solvents, reference to "an excipient" includes mixtures of two or more such materials, and the like.

Figure 1:
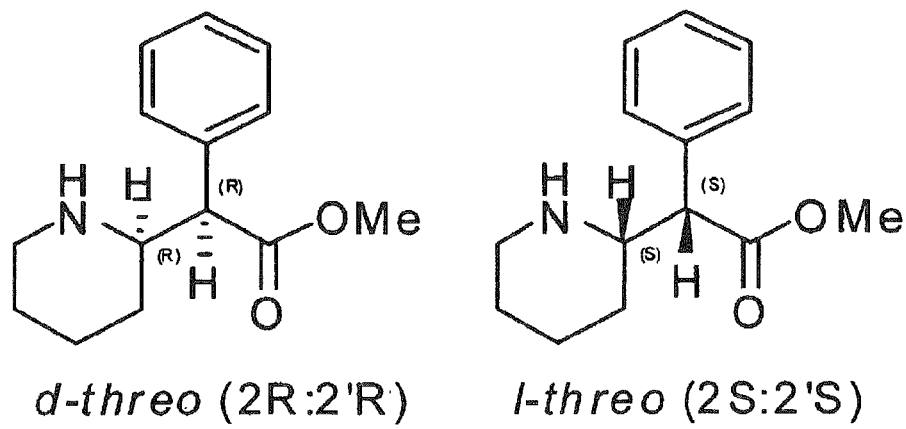
FIG. 1 depicts the chemical structure of the d- and l-threo isomers of methylphenidate.

The mechanism of action of methylphenidate in ADD/ADHD is not fully understood, however the primary effects appear to be mediated through the blockage of the presynaptic dopamine transporter. Methylphenidate also exerts a relatively minor effect on norepinephrine reuptake that also contributes to activity. Volkow, et al. (1998) *Am J Psychiatry* 155:1325-1331; Volkow et al. (1999) *Life Sci* 6:PL7-12; and Volkow et al. (2002) *Synapse* 43:181-187. Unlike amphetamine, methylphenidate blockade of the dopamine receptor is not thought to induce transporter conformation change resulting in the release of dopamine into the synaptic cleft as the receptor returns to its former conformation. Markowitz, et al. (2003) *Pharmacotherapy* 2: 1281-1299. With the exception of Focalin, of the four possible methylphenidate isomers, a mixture of the d,l-threo enantiomers is used in all current immediate and controlled release formulations; the erythro-isomer pair being much less active. Srinivas et al. (1992) *Clin Pharmacol Ther* 52:561-568. The d-threo isomer is the most active of the two threo isomers (a 2:1 potency compared to the d,l-threo-mixture) and is the sole active constituent in the Focalin brand methylphenidate product. The chemical structure of the d- and l-threo isomers of methylphenidate is shown in FIG. 1.

Oral absorption of methylphenidate is essentially complete and rapid, wherein the $T_{max}$ following oral administration of immediate release methylphenidate has been found to be between 1 and 3 hour (mean 1.5 h). The drug crosses the blood-brain barrier readily and the systemic half-life of methylphenidate is approximately 3 hours. Bioavailability is limited and is widely variable between patients due to extensive first-pass metabolism. *CPS Compendium of Pharmaceuticals and Specialties*, 34th ed.; Gillis, M., Ed. Canadian Pharmacists Association: Ottawa, 1999; pp 1573-4. About 70% of the dose is deesterified to the inactive major metabolite, ritalinic acid, which is excreted in the urine. Metabolism of the active d-threo isomer is slower than that of the inactive l-threo isomer resulting in approximately a 10:1 d-threo to l-threo plasma concentration ratio. Food may increase absorption rate but does not affect the extent of absorption. These pharmacokinetic parameters do not differ greatly between adults and children. Markowitz et al. (2003) *Pharmacotherapy* 22:1281-1299.

Immediate release methylphenidate preparations, because of their short half-life, require frequent administration at short intervals to ensure adequate treatment throughout a child's school day. The rapid onset and offset of immediate release methylphenidate preparations means that a medicated child with attention deficit disorder will be maximally affected only for relatively brief periods during the day. Due to its short half-life, immediate release MPH is usually given twice per day, usually once after breakfast and once during the school day, an event that some children and some school personnel apparently avoid, resulting in poor compliance with prescribed regimens. Compliance is a major problem for children who require a midday or mid-afternoon dose as many schools prohibit children from taking medications during the school day and others often insist that all medications be given by a nurse. Poor compliance in taking medication may explain, in part, the variable and conflicting results reported in many studies of the effect of medication on improving the behavior of hyperactive children.

Figure 2:
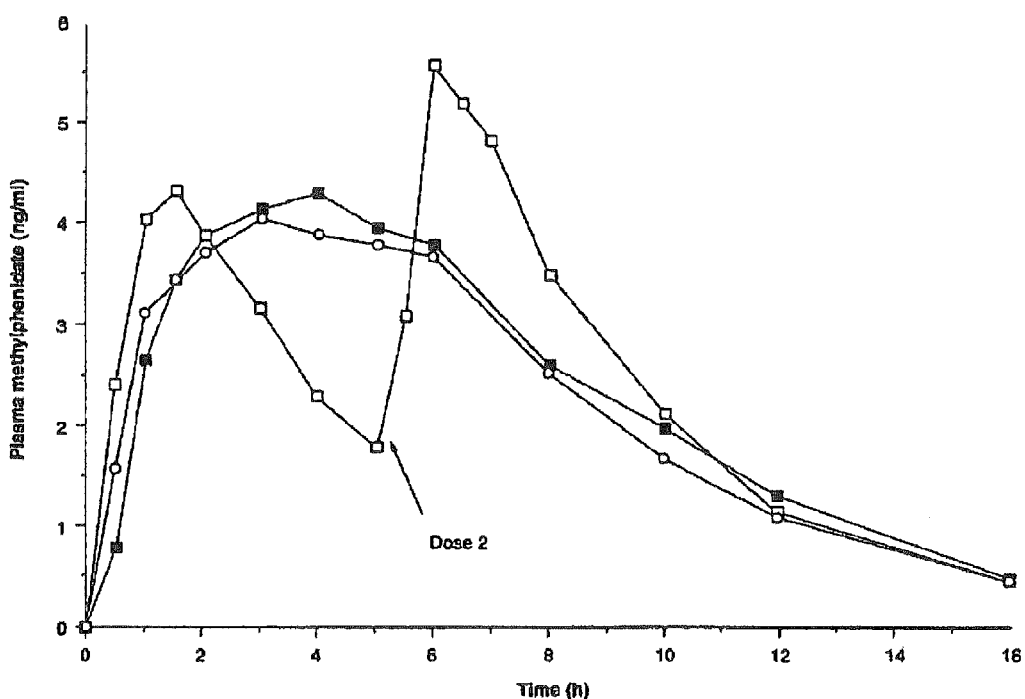
FIG. 2 depicts a comparison of mean pharmacokinetic profiles of immediate release ("IR") methylphenidate Ritalin SR and a generic sustained release methylphenidate.

The rapid clearance of methylphenidate has led to the development of a number of controlled formulations to overcome the so-called treatment "bounce" that resulted from large changes in plasma methylphenidate levels over the course of a day, to increase patient compliance and reduce the stigma associated with having to take medication at school. The first extended release formulations of methylphenidate, Ritalin SR brand and, subsequently, the Metadate ER and Methylin ER brands, used wax-based release systems and were not considered to be useful improvements over immediate release methylphenidate. The poor efficacy of these drugs has been, in part, attributed to a relatively long onset period of 2-3 hours (Greydanus, D. E. *Psychiatric Times*, Vol. 20, No. 5, published online May 1, 2003) that does not allow for behavioral management in the early morning and insufficient duration of action (4-6 hours), failing to eliminate the need for an afternoon dose and, consequently, these products have not been generally recognized as a true QD dose. A comparison of mean pharmacokinetic profiles of immediate release ("IR") methylphenidate, Ritalin SR and a generic sustained release methylphenidate is depicted in FIG. 2. As can be seen, based on PK parameters, the Ritalin SR product has a slower onset and shorter duration than two IR methylphenidate doses. Erratic pharmacokinetics arising from the wax-based release technology and limited available dosage strengths (Ritalin SR provided as only 20 mg strength; Metadate ER and Methylin ER: provided only as 10 and 20 mg strengths) seem to have further limited the attractiveness of the first generation extended release products.

In addition to these factors, a study suggested that a flattened plasma concentration curve after establishment of peak concentration, such as that which could be achieved using the Ritalin-SR product, was not as efficacious as a rising plasma concentration profile. Swanson et al. (1999) *Clin Pharmacol Ther* 66:295-305. The concept of "acute tolerance" was proposed to rationalize the superior efficacy of the rising plasma concentration. This concept is discussed in more detail below.

Figure 3:
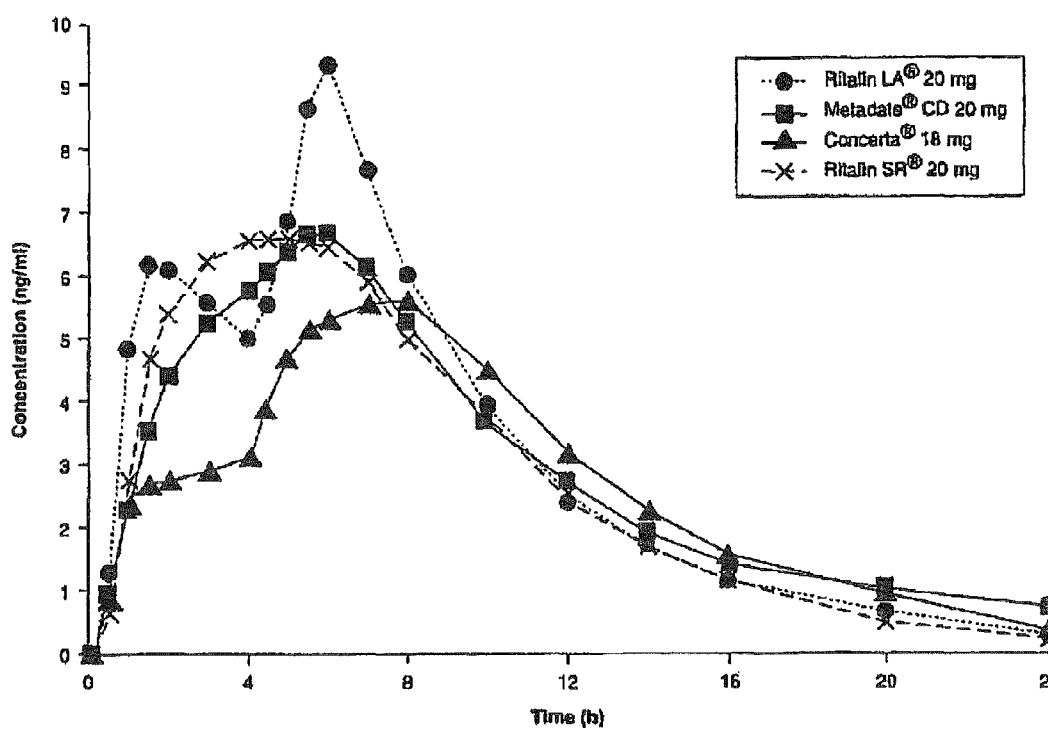
FIG. 3 depicts a comparison of plasma concentrations achieved with the Ritalin LA, Metadate CD, Concerta and Ritalin SR products.
Figure 4:
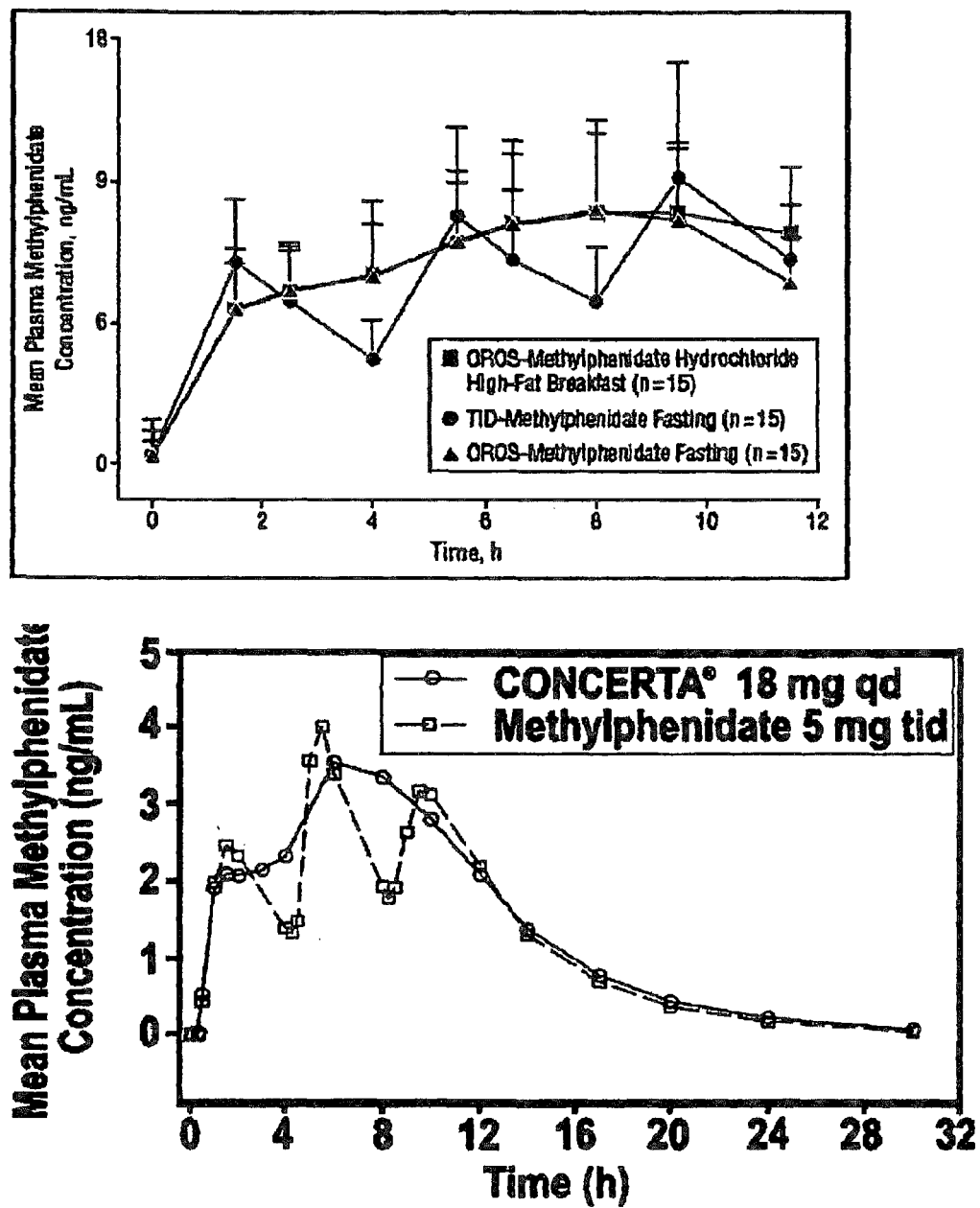
FIG. 4 show the PK profiles from a 3-way crossover study of IR methylphenidate TID and Concerta without food (fasted) and after high-fat breakfast (taken from Swanson et al. (2003) *Arch Gen Psychiatry* 60:46-63) and mean plasma methylphenidate concentrations compared to TID methylphenidate (taken from Concerta label).

New, second generation, extended release methylphenidate formulations have been developed to overcome the above-described limitations of the first generation products (e.g., Ritalin-SR). In particular, Concerta (ALZA, US launch 2000), Ritalin LA (Novartis, US launch 2002) and Metadate CD (UCB, US launch 2001) all have an earlier onset and longer duration of action than Ritalin-SR. A comparison of plasma concentrations achieved with the Ritalin LA, Metadate CD, Concerta and Ritalin SR products (taken from Patrick et al. (2005) *Expert Opin Drug Deliv* 2:121-143) is provided in FIG. 3. The Concerta product is based upon an osmotic capsule ("OROS") controlled release technology and was designed to mimic a TID dosing regimen with two different release formulations within the capsule and a drug "overcoat" to provide an immediate release portion of the total methylphenidate dose. FIG. 4 presents the PK profiles from a 3-way crossover study of IR methylphenidate TID and Concerta without food (fasted) and after high-fat breakfast (taken from Swanson et al. (2003) *Arch Gen Psychiatry* 60:46-63) and mean plasma methylphenidate concentrations compared to TID methylphenidate (taken from Concerta label). As a result, the initial rate of rise for the Concerta product's plasma profile is very similar to that seen with an immediate release dose. Comparison of the pharmacokinetics of Concerta with a TID dose of immediate release methylphenidate is shown in FIG. 4.

Both of the Ritalin LA and Metadate CD second-generation methylphenidate products use microbead technology to deliver an immediate release dose of methylphenidate followed by a second delayed dose, mimicking a BID delivery schedule. Ritalin LA uses a technology ("SODAS") to deliver half the dose immediately followed by the remainder after an interval of 4 hours. Metadate CD uses a different technology ("Diffucaps") to deliver thirty percent (30%) of the methylphenidate dose by immediate release and the remaining seventy percent (70%) after an interval of 3-4 hours. For Metadate CD, this dose schedule was determined in a clinical study to give more consistent results than ratios of, e.g., 20:80 or 40:60, and to approximate to a biphasic plasma concentration versus time profile similar to Ritalin BID in healthy adult subjects and in children with ADHD. Wigal at al. (2003) *Journal of Applied Research* 1:46-63.

A methylphenidate delivery rate that results in a substantially ascending plasma concentration profile has been proposed as a requirement for superior efficacy against ADHD. This hypothesis arose from a dose-sipping study carried out to determine the optimal pharmacokinetic profile for a new methylphenidate formulation. Swanson et al. (1999) *Clin Pharmacol Ther* 66:295-305. The study was carried out by dosing identical capsules containing different quantities of drug at 30 min intervals. The dosing schedules were designed to mimic BID, flat and ascending profiles. For example, a flat profile was achieved by dosing an initial large drug bolus followed by small doses during the day to maintain a steady profile. Surprisingly, a dose schedule mimicking an ascending profile was found to have superior efficacy compared to the flat profile. These studies showed that an ascending methylphenidate dosing regimen became as efficacious as the standard BID dosing regimen by the afternoon, suggesting that a large morning bolus is not required for significant improvement in ADHD symptoms. It was speculated that this large morning bolus dose could potentially give rise to acute tolerance, thereby requiring a larger dose to maintain efficacy later in the day. Swanson et al. (1999) *Clin Pharmacol Ther* 66:295-305. However, a major limitation of this study was that dosing schedules derived from calculated plasma concentrations were modeled from published immediate release methylphenidate data and no pharmacokinetic measurements or actual comparisons with Ritalin SR were undertaken. Nevertheless, the results of these studies led to the development of the Concerta controlled release methylphenidate product (Pelham et al. (2001) *Pediatrics* 107:E105; Wolraich et al. (2001) *Pediatrics* 10:883-892), which since its launch in 2000 has been the most successful methylphenidate formulation for the treatment of ADHD, dominating the market.

The concept of "acute tolerance" was proposed to rationalize the findings described above. Swanson et al. (1999) *Clin Pharmacol Ther* 66:295-305. This hypothesis was supported by previous studies on the PK and effects of intravenously delivered methylphenidate on the brain. Volkow et al. (1999) *Life Sci* 65:PL7-12; Volkow et al. (1996) *Psychopharmacology (Berl)* 123:26-33; Volkow et al. (1996) *Proc Natl Acad Sci USA* 9: 10388-92. In these PET studies, it was found that uptake of $^{11}$C-labeled methylphenidate into the brain after an IV dose was very fast ($T_{max}$<10 min) and was followed by relatively slow clearance (half life=90 min). The rapid onset of methylphenidate into the brain resulted in feelings of euphoria, however these faded rapidly while there were still appreciable methylphenidate brain levels and receptor occupancy. In contrast, when methylphenidate was dosed orally, the brain $T_{max}$ was similar to that measured in plasma and euphoria was not observed, even though the same receptor occupancy levels were reached for the same dose. Volkow, et al. (1998) *Am J Psychiaty* 155:1325-1331; Swanson et al. (2002) *Behav Brain Res* 130:73-78. The differences in brain effects between oral and IV methylphenidate were attributed to acute tolerance at the dopamine transporter. The authors suggested that after IV dosing, the initial rise in dopamine levels was unchecked by acute tolerance thus leading to euphoria, whereas after oral dosing, the comparatively slower increase in brain dopamine levels resulted in acute tolerance which prevented the reinforcing effects seen with IV dosing. This hypothesis was extrapolated to account for the perceived differences in efficacy over time at lower, pharmacological oral doses of methylphenidate.

However, there were no data presented to support this hypothesis of acute tolerance, and moreover alternative hypotheses suggest that the selective euphoric effect of an intravenous dose was due to its effects in a brain region, e.g., mesolimbic vs mesostriatal (Wightman et al. (2002) *J Neurochem* 82:721-735), that is not affected by oral doses of methylphenidate and that has been implicated in the reinforcing effects of abused drugs. Swanson et al. (2003) *Neurosci Biobehav Rev* 27:615-621. The clinical relevance of acute tolerance and the importance of a rising plasma profile therefore remain to be fully substantiated.

Figure 5:
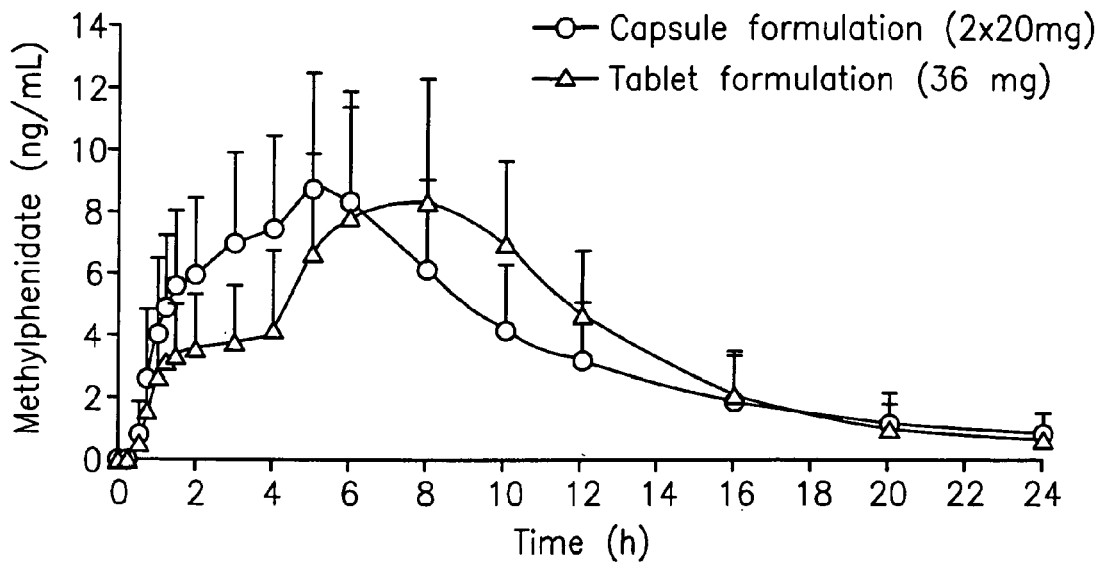
FIG. 5 shows a direct comparison of pharmacokinetics of methylphenidate released from Concerta (tablet formulation) and Metadate CD (capsule formulation), and Ritalin LA
Figure 5:
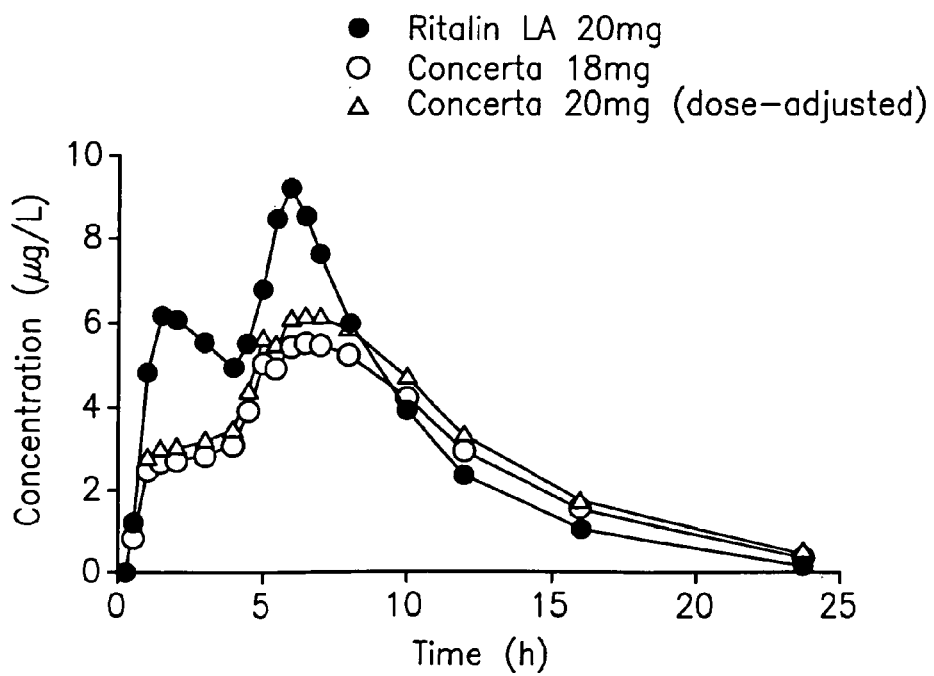

The pharmacokinetics of Concerta have been compared directly with Metadate CD (Gonzalez at al. (2002) *Int J Clin Pharmacol Ther* 40:175-184), a formulation mimicking BID dosing of methylphenidate and Ritalin LA (Markowitz et al. (2003) *Clin Pharmacokinet* 42:393-401), a bimodal BID-like formulation. FIG. 5 shows a direct comparison of pharmacokinetics of methylphenidate released from Concerta (tablet formulation) and Metadate CD (capsule formulation), and Ritalin LA. From the PK profiles, it appears that Concerta has significantly lower plasma concentration between 1 and about 6 hours after dosing (compared to Metadate CD) and between 1 and about 8 hours (for Ritalin LA). After about 8 hours post dose, the plasma concentration of Concerta is higher than that of the other two competitor formulations.

The efficacy and duration of action of Concerta has also been compared directly with Metadate CD and Ritalin LA in two separate studies. Both studies were carried out in children using a laboratory school setting that controls for the structure of the day and enables monitoring of efficacy at different timepoints during the day. Swanson et al. (1998) *Psychopharmacol Bull* 34:55-60. Similar established and validated measures of attention and deportment ("SKAMP") as well as structured math tests were used to assess the patients. In both trials, all the evaluated drugs were found to be effective, however the different release profiles of each formulation resulted in distinct differences between the effects on measures of attention and deportment.

In the first study, Concerta was found to be longer acting than Metadate CD, and Concerta was found to be superior in the period 8 to 12 hours post dose. However, Concerta was found to be less efficacious than the comparator drug in the period up to about 6-8 hours post dose. Swanson et al. (2004) *Pediatrics* 113:e206-216. In this comparative study with Metadate CD no significant differences between the pharmacodynamic trends were seen for measures of SKAMP deportment and PERMP (math test-based measurements) for the different dose levels. However, the effect of dose on SKAMP attention was significant. A high correlation of the initial bolus dose released from the two formulations with Effect Size (a parameter derived from the difference of the active mean and the placebo) for the morning time points was observed. The authors investigated this observation further by normalizing the Effect Size by dose, and hence anticipated plasma concentration, to probe whether the correlation seen was dose-related or whether there was an additional effect, such as acute tolerance, in play. Once this adjustment had been made, the difference in response was found to be insignificant. Based on this observation, the authors proposed that the low dose group may have benefited from a higher dose in the early morning.

In the second study comparing Ritalin LA against Concerta (Lopez et al. (2003) *Paediatr Drugs* 1:545-555), patients were assessed at time increments up to 8 hours rather than the 12 hour duration described in the first study. In the time period between dose and 8 hours, Ritalin LA was found to be more effective than Concerta. At the 8 hour time point, the two drugs were indistinguishable. Interestingly, in the interval between 2 and 4 hours post dose, Ritalin LA was found to be more efficacious than Concerta. This period corresponds to a rapid decrease of methylphenidate plasma concentration resulting from the Ritalin LA formulation. If a smoothly ascending profile were key to activity, it would be expected that Concerta would have superior activity at these time points even if the plasma concentration was lower.

Figure 6:
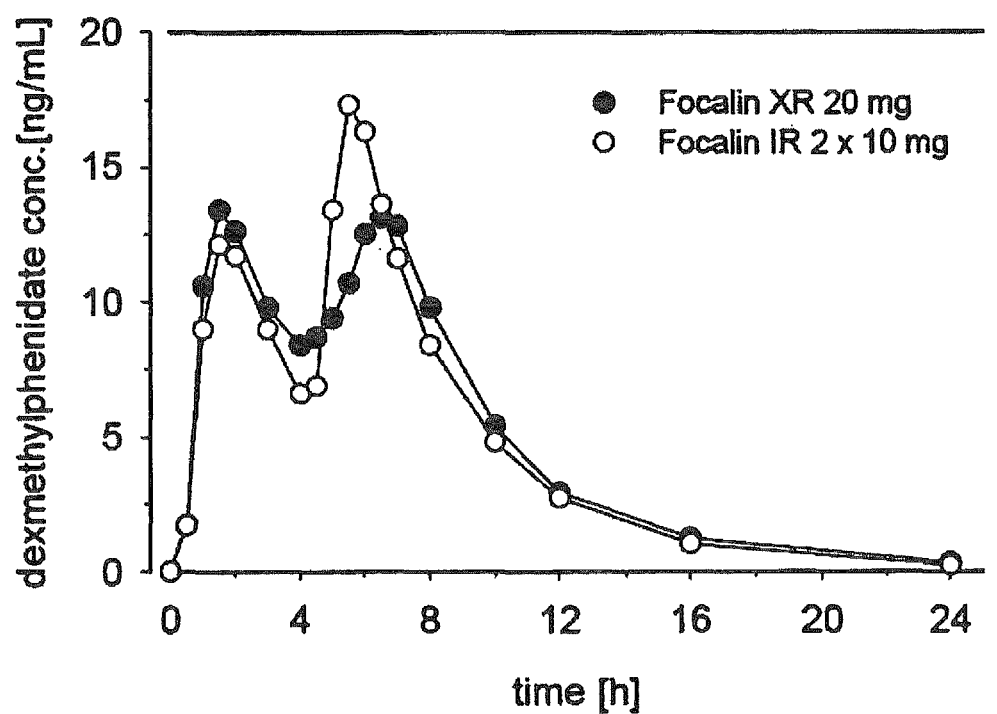
FIG. 6 depicts the PK profile of Focalin XR compared to two IR doses of Focalin IR.

By considering the long-acting methylphenidate formulations as equivalent to BID or TID immediate release dosing, it has been suggested that if acute tolerance were to occur, then the optimum serum concentration at the peak of the equivalents of $2^{nd}$ or $3^{rd}$ immediate release dose in the PK profile of the formulation would need to be higher than the optimal serum concentration at the equivalent peak for the first immediate release dose to ensure adequate efficacy and to override the acute tolerance effect. Swanson et al. (2002) *Behav Brain Res* 130:73-78. Although Concerta does have a PK profile in which the points in the plasma profile that correspond to the $2^{nd}$ and $3^{rd}$ TID equivalent doses are higher than the first peak, data from the comparative trials suggests that, in contradiction to the acute tolerance hypothesis, a higher earlier plasma concentration may be preferred for better efficacy during the morning hours. Of the other long acting formulations of methylphenidate, Ritalin LA and Metadate CD both have bimodal kinetics and have a higher second plasma peak and Focalin XR, a bimodal formulation of the pure d-threo isomer has equal plasma peaks and has been reported to effective for 8-12 hours. See, e.g., FIG. 6 which depicts the PK profile of Focalin XR compared to two IR doses of Focalin IR (taken from the Focalin XR label).

Figure 7:
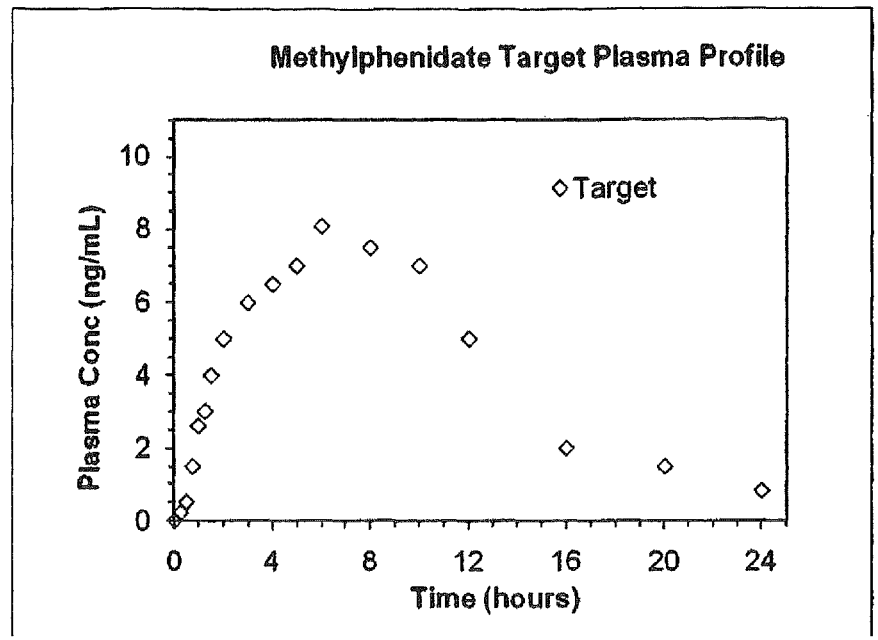
FIG. 7 depicts the methylphenidate PK profile provided by the oral controlled release dosage forms of the present invention.

It is therefore a primary object of the present invention to provide for improved oral controlled release dosage forms for the delivery of methylphenidate for use in the treatment of ADD and ADHD. As used herein, "methylphenidate" includes all forms of the active pharmaceutical ingredient, including dexmethylphenidate, d-threo methylphenidate, and dl-threo-methylphenidate. Contrary to the theories commonly held by key opinion leaders in the ADHD field that dictate the design of current "state-of-the-art" controlled release methylphenidate dosage forms, the inventors believe that the clinical significance of acute tolerance remains theoretical and thus the need for ramping plasma concentrations (ascending release profiles) is not necessary for achieving optimal plasma concentrations in individual patients. The improved oral controlled release dosage forms of the present invention are designed to provide a longer duration of action than that provided by existing CR methylphenidate dosage forms, as well as a rapid onset of action. The controlled release dosage forms are thus characterized by: (i) a first, increasing in vivo rate of release of methylphenidate from the controlled release system that provides an initial increasing-rate phase of less than or equal to about 2 hours, and is sufficient to provide a therapeutically effective amount of methylphenidate for a rapid onset of action; (ii) a second, zero-order or decreasing (i.e., non-ascending) in vivo rate of release of methylphenidate from the controlled release system that provides a subsequent zero order- or decreasing-rate phase sufficient to provide a therapeutically effective amount of methylphenidate through at least about 11 to 12 hours post administration; and (iii) a single $T_{max}$ of about 5.5 to 7.5 hours post administration. The novel and unique in vivo methylphenidate release kinetics provided by the oral controlled release dosage forms of the present invention are sufficient to provide the methylphenidate in vivo PK profile depicted in FIG. 7. A comparison of the methylphenidate in vivo PK profile provided by the present oral dosage forms with the PK profiles from Metadate CD and Concerta products is provided in FIG. 8.

It is generally recognized that the mere presence of an active substance in the gastrointestinal fluids does not, by itself, ensure bioavailability and/or PK performance. Bioavailability is the degree or amount to which a drug substance is absorbed into the systemic circulation in order to be therapeutically available. In order to be absorbed, an active drug substance must be in a solution. The time required for a given proportion of an active drug substance contained in a controlled release dosage form to enter into solution in appropriate physiological fluids is known as the dissolution time. The dissolution time for an active substance from a dosage form is determined as the proportion of the amount of active drug substance released from the dosage unit over a specified time by a test method conducted under standardized conditions. Thus, for oral dosage forms such as the controlled release oral dosage forms of the present invention, physiological fluids mimicking the gastrointestinal tract are used as the media for determining dissolution time. The present state-of-the-art test procedures for establishing dissolution time for controlled release pharmaceutical compositions are well known by the skilled person and described in official compendia world wide.

Although there are many diverse factors that may influence the dissolution of a drug substance from a controlled release system, the dissolution time determined for a pharmacologically active substance from a specific composition is relatively constant and reproducible. Among the different factors affecting the dissolution time are the surface area of the drug substance presented to the dissolution solvent medium, the pH of the solution, the solubility of the substance in the specific solvent medium, and the driving forces of the saturation concentration of dissolved materials in the solvent medium. Thus, the dissolution concentration of an active drug substance is dynamically modified in this steady state as components are removed from the dissolution medium. Under physiological conditions, the saturation level of the dissolved materials is replenished from the controlled release dosage form reserve to maintain a relatively uniform and constant dissolution concentration in the solvent medium, providing for a steady-state absorption.

The transport across a tissue absorption site in the gastrointestinal tract is influenced by the Donnan osmotic equilibrium forces on both sides of the membrane, since the direction of the driving force is the difference between the concentrations of active substance on either side of the membrane, i.e. the amount dissolved in the gastrointestinal fluids and the amount present in the blood. Since the blood levels are constantly being modified by dilution, circulatory changes, tissue storage, metabolic conversion and systemic excretion, the flow of active materials is directed from the gastrointestinal tract into the blood stream.

Notwithstanding the diverse factors influencing both dissolution and absorption of a drug substance, in many cases an important correlation can be established between the in vitro dissolution release performance determined for an oral controlled release dosage form and the in vivo bioavailability/PK performance for that product. This correlation is so firmly established in the art that dissolution time has become generally descriptive of bioavailability potential for many classes of active components contained in a particular dosage form. In view of this relationship, the in vitro dissolution release performance determined for an oral controlled release dosage form is one of the important fundamental characteristics for consideration when evaluating whether a controlled release formulation should be tested in vivo.

The concept of in vitro/in vivo correlation (IVIVC) determination for oral controlled release dosage forms is thus a well-known tool used by pharmaceutical scientists, allowing for the prediction of expected bioavailability and other pharmacological performance characteristics from in vitro dissolution profile characteristics. Information and guidance regarding IVIVC determination can be found on the US FDA website and in other pharmacological reference sites.

Figure 8:
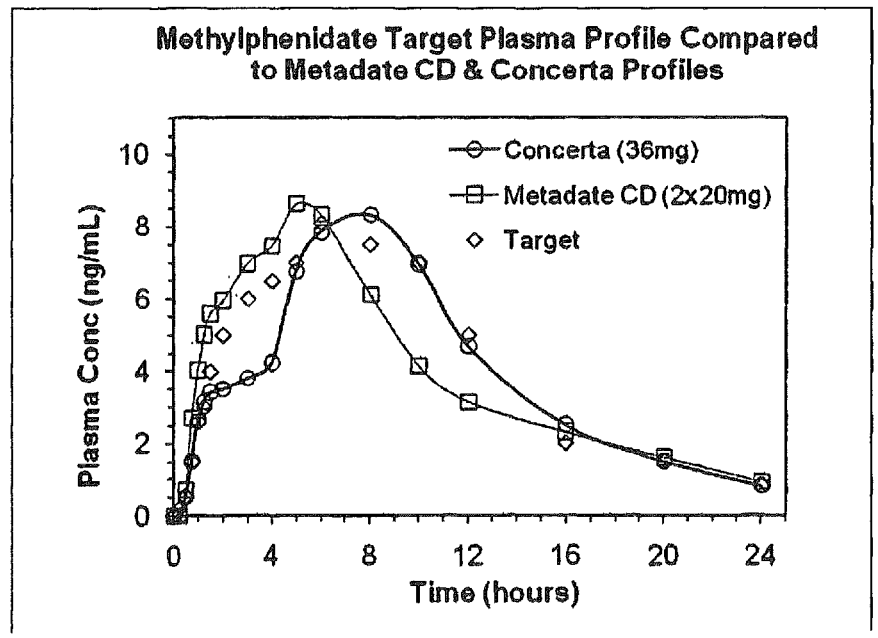
FIG. 8 depicts a comparison of the methylphenidate PK profile provided by the oral controlled release dosage forms of the present invention with the PK profiles from Metadate CD and Concerta products.

Keeping the above general considerations in mind, optimal in vitro release profiles for an oral controlled release dosage form produced in accordance with the present invention can be defined as follows. The methylphenidate plasma profile of FIG. 7 can be defined in relation to plasma profiles reported in the patent literature for Metadate CD and Concerta controlled release methylphenidate products (40 and 36 mg strengths, respectively). This relationship is depicted in FIG. 8. According to the linear theory of pharmacokinetics (PK), the plasma profile of a compound can be written as the convolution of the rate of input into the systemic circulation, I(t), and the unit impulse response, UIR, derived from the plasma profile measured following intravenous (IV) bolus injection. Thus, a target input rate can be defined from the target plasma profile and UIR for methylphenidate by the process of deconvolution.

The next step is to link the input rate in vivo to release rates in vitro. If no human plasma profiles for a candidate methylphenidate formulation are available, this can only be done approximately as follows. Using the human data available for Metadate CD and Concerta, the input rates via deconvolution can be calculated for the two products. In addition, the in vitro methylphenidate release rates can be determined using standard in vitro dissolution testing methods as described herein above, and in the working examples below. This allows one to establish the functional relationships (IVIVC) between the cumulative methylphenidate input rates in vivo and cumulative release in vitro for the Metadate CD and Concerta products as defined by the following:

$$C_p(t) = \int_0^t I(\tau) \cdot \mathrm{UIR}(t-\tau) d\tau$$

wherein the units of the input rate ($I(\tau)$) are mg/hour, and the unit impulse response (UIR) is in units of ng/mL/mg dose; and the human plasma profile ($C_p(t)$) is in units of ng/mL. The integral involves the variable ($\tau$) which denotes time. Time is fixed during any given evaluation of the integral.

Using the IVIVC relationship for Metadate CD, one may then calculate an in vitro release profile from the target in vivo input rate. This profile of cumulative methylphenidate release in vitro provides a target that candidate formulations can match, with a reasonable confidence that such formulations would achieve the target human plasma profile.

Figure 9:
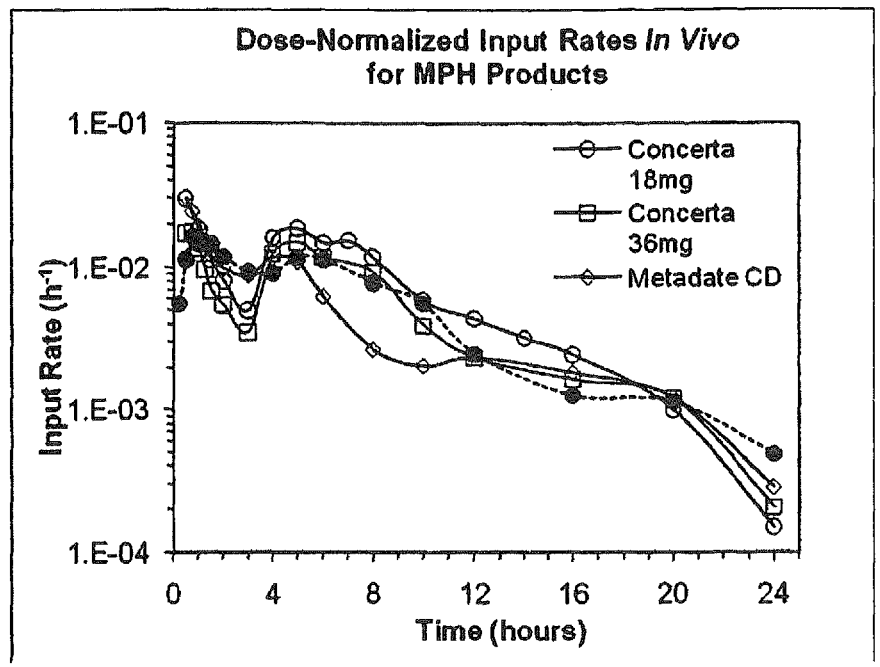
FIG. 9 depicts the dose-normalized results of a deconvolution analysis of Metadate CD and Concerta used to define a target input rate for a controlled release oral dosage form produced in accordance with the present invention.

Next, definition of an approximate impulse response from PK parameters found in Table A-II-1 of *The Pharmacological Basis of Therapeutics* (11$^{th}$ edition, Eds: Brunton et al., McGraw Hill, New York, 2006) can be carried out. Specifically, values of the clearance (CL) and volume of distribution ($V_d$) for the (+) and (−) dextro forms of MPH are averaged and weighted according to their respective bioavailabilities (BA). For plasma data in units of ng/mL, the unit impulse response can be defined as UIR=$10^6 \cdot \exp(-k_{el}t)$/$V_d$ ng/mL/mg; wherein ($k_{el}$) is the terminal elimination rate of methylphenidate from the body, which can be evaluated inter alia, from a non-compartmental analysis of intervenous bolus data. It is defined in terms of two other pharmacokinetic parameters, the whole body clearance (CL) i.e., the volume of blood cleared of a compound in unit time; ($V_d$) which is a measure of the extent to which a compound distributes initially from the systemic circulation to other tissues such that: $k_{el}$=CL/$V_d$ Deconvolution of Metadate CD, Concerta and the target plasma profiles can then be done in WinNonLin (version 5.2, Pharsight Corp., Mountain View, Calif.). The dose-normalized results of such a deconvolution analysis are depicted in FIG. 9.

Figure 10A:
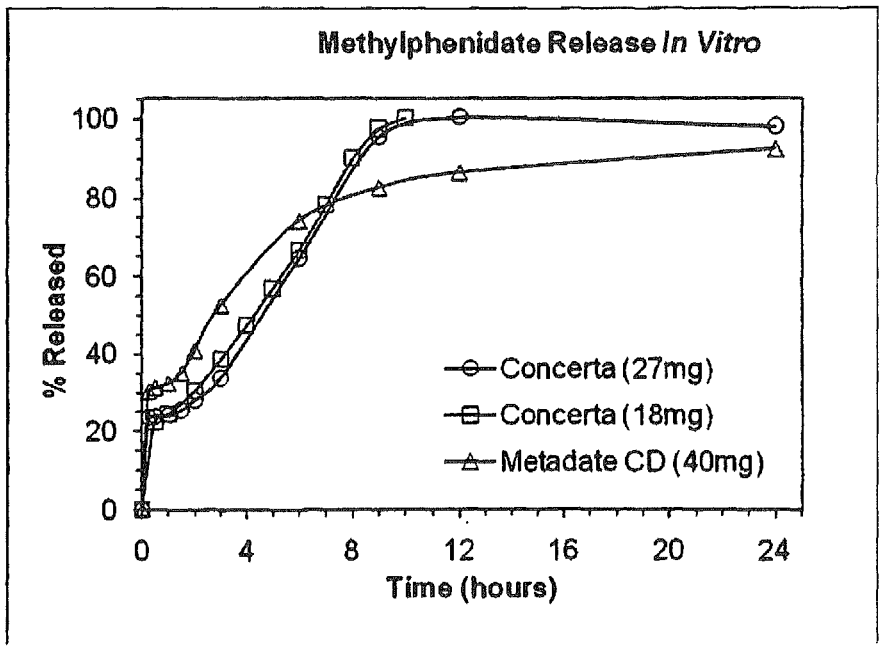
FIGS. 10A and 10B depict the results obtained in Example 2b, where
Figure 10B:
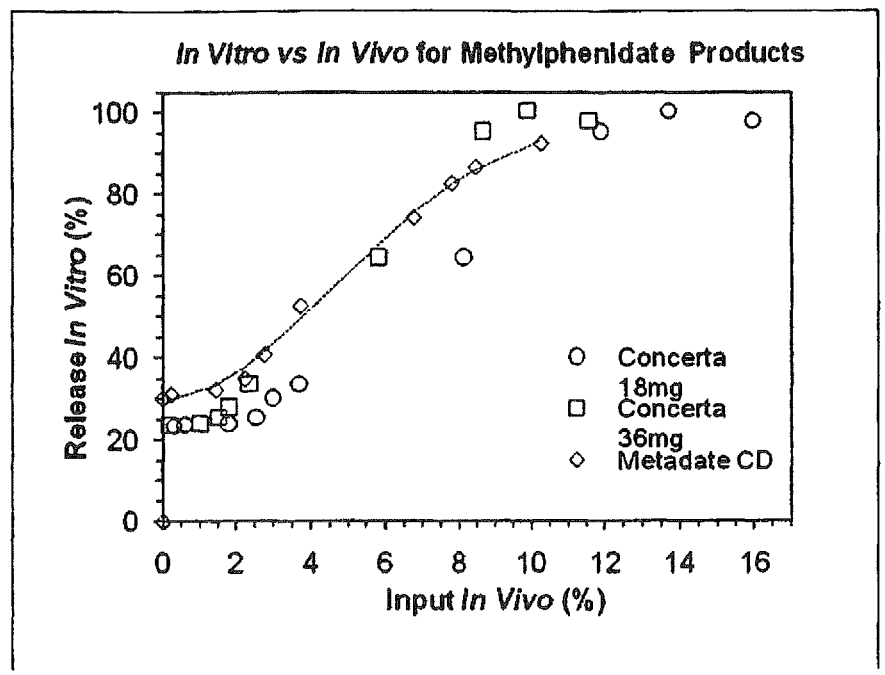

As described in Example 2b, below, the in vitro release for Metadate CD (40 mg) and for various doses of Concerta (18, 27 and 36 mg) were measured. The results of this initial analysis are depicted in FIGS. 10A and 10B. In FIG. 10A, the cumulative release profiles obtained in the measurements are compared with cumulative release data presented in the U.S. Pat. No. 6,919,373 for the Concerta product. In FIG. 10B, the measured cumulative release in vitro is plotted against input in vivo obtained via deconvolution (open symbols) for both Metadate CD and Concerta. The results presented in these figures are described well by Weibull functions:

$$y=(100-\alpha) \cdot [1-e^{-(x/\chi)^\beta}]+\alpha$$

where $\alpha$, $\beta$ and $\chi$ are constants; particularly, where $\alpha$ is the percent of dose that is released from the dosage form immediately, $\chi$ is a scale factor (the extent of input in vivo at which 62.5% of the remaining dose is release in vitro); and $\beta$ alters the shape of the fitting curve. In the case at hand, by a least squares fit of the in vitro and in vivo data, $\alpha$=29.7% (27, 32.5); $\chi$=6.60 (6.24, 6.95); and $\beta$=1.94 (1.65, 2.23), where the parenthetical values define the 95% confidence intervals. The fit for Metadate CD is shown by the dotted line in the graph of FIG. 10B ($r^2_{adj}$=99.6%). An advantage of the Weibull representation is that it can be inverted analytically. This advantage is useful in order to predict cumulative input in vivo and human plasma profiles from in vitro release profiles of selected candidate oral controlled release formulations in the practice of the invention.

Figure 11:
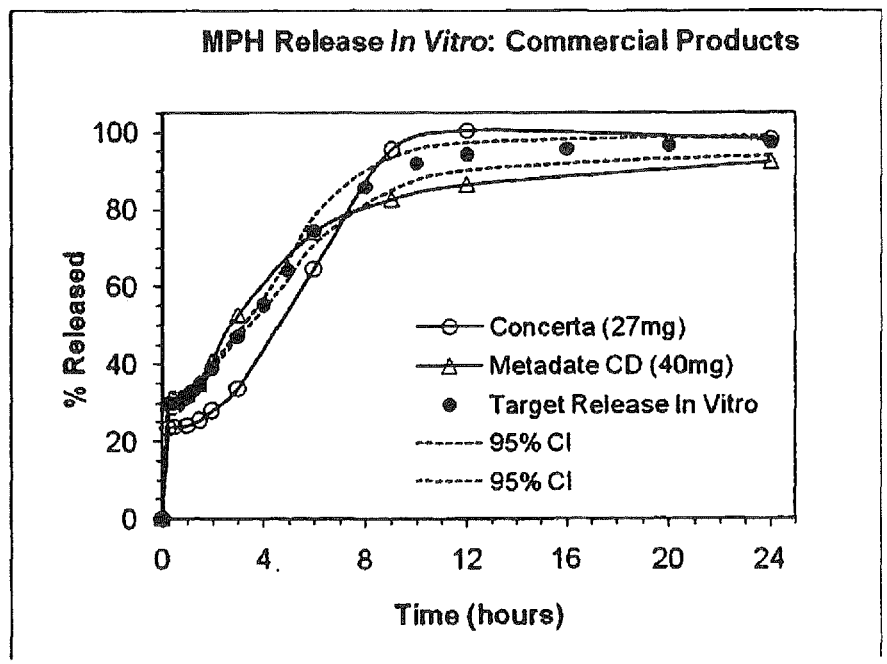
FIG. 11 depicts how the Weibull model for Metadate CD can be applied to calculate target cumulative release in vitro from the target cumulative input in vivo in the practice of the invention.

Accordingly the Weibull model for Metadate CD can now be applied to calculate target cumulative release in vitro from the target cumulative input in vivo. The results of such a calculation are presented in FIG. 11, where confidence intervals for the in vitro release profile are defined by the 95% confidence intervals for the parameters of the Weibull model. In addition, the target in vitro release profile thus obtained can be compared to the methylphenidate in vitro dissolution profiles for candidate formulations as described in Example 2b below.

Figure 12:
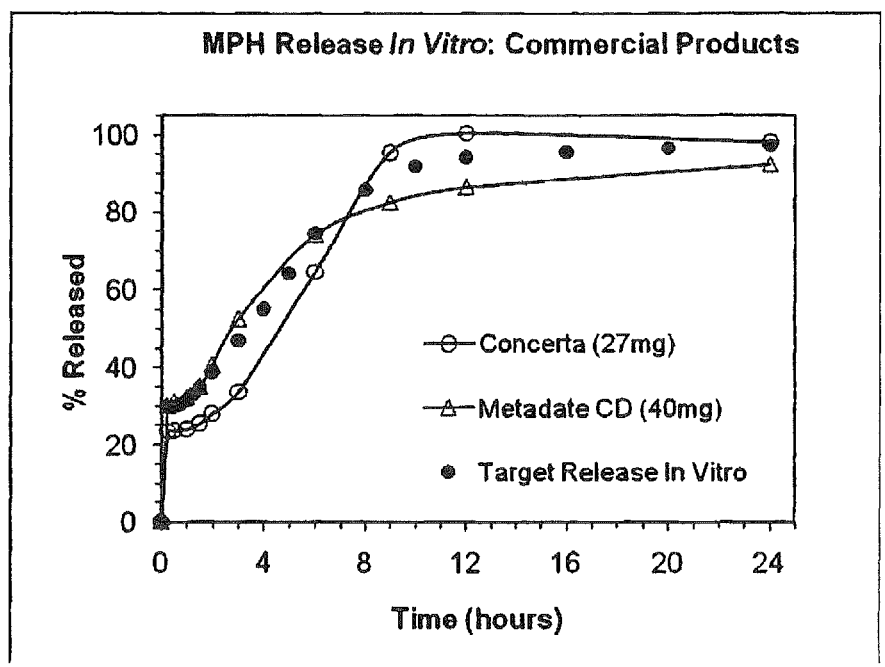
FIG. 12 depicts the target in vitro cumulative release profile of a controlled release oral dosage form produced in accordance with the present invention compared against the release profiles obtained from Metadate CD and Concerta.

It is accordingly also an object of the present invention to provide a controlled release oral dosage form containing methylphenidate, wherein the dosage form is characterized by providing the target in vitro cumulative release profile as depicted in FIG. 12.

In one aspect of the invention, a controlled release oral pharmaceutical dosage form is provided that comprises methylphenidate in a controlled release carrier system. The subject dosage form is characterized by: (i) a first, increasing in vivo rate of release of methylphenidate from the controlled release system that provides an initial increasing-rate phase of less than or equal to about 2 hours, and is sufficient to provide a therapeutically effective amount of methylphenidate for a rapid onset of action; (ii) a second, zero-order or decreasing (i.e., non-ascending) in vivo rate of release of methylphenidate from the controlled release system that provides a subsequent zero order- or decreasing-rate phase sufficient to provide a therapeutically effective amount of methylphenidate through at least about 11 to 12 hours post administration; (iii) a single $T_{max}$ of about 5.5 to 7.5 hours post administration; and (iv) the controlled release carrier system provides enhanced in vivo pharmacokinetic performance. The novel and unique in vivo methylphenidate release kinetics provided by the oral controlled release dosage forms of the present invention are sufficient to provide the methylphenidate in vivo PK profile depicted in FIG. 7. In certain aspects, the in vivo release of methylphenidate from the carrier system is substantially free from food effect. In other aspects, the carrier system has a food effect such that the in vivo absorption of methylphenidate from the carrier system is actually enhanced when administered in the presence of food.

In this regard, the physiological behavior of the stomach is usually determined by whether it contains food (fed state) or is empty (fasted state). In the fed state, food is mixed and partially digested in the distal stomach as the stomach undergoes contractions, helping to move materials into the main part of the stomach for further digestion. At the end of a digestive period, the stomach enters the fasting stage and begins a cycle called the interdigestive myoelectric motor cycle. These changes in physiological behavior, as well as certain concomitant chemical changes (e.g., pH) as the stomach switches between fed and fasted states may give rise to variability in the rate and/or amount of delivery of methylphenidate from an oral dosage form. More particularly, a variety of formulation-dependent food-induced absorption changes (hereinafter "food effect") can occur with controlled release compositions. These changes can include decreases in the rate and/or extent, increases in the rate and/or extent when taken in fed or fasted states, and erratic or variable absorption of methylphenidate from a controlled release composition such as differences in absorption when the composition is taken with low-fat or high-fat meals. In extreme cases, a controlled release composition can have a significant food effect such that when the composition is taken with food, or with different kinds of food (high fat versus low fat meals), there can be a significant increase in absorption (dose dumping) that can cause such a dosage form to be unsafe. In these cases, that is, where a formulation exhibits a pronounced food effect, the dosing relative to meal intake may be made part of the product labeling to assure consistent and safe absorption. If the difference in both the rate and extent of absorption of an active agent from an oral dosage form varies significantly when it is administered in a fed versus a fasted state, the dosage form is characterized as having a food effect. In some cases, a dosage form can have a food effect wherein administration of the dosage form with food will enhance the bioavailability of the methylphenidate active agent. On the other hand, if there is not a significant difference in both the rate and extent of absorption of an active agent from an oral dosage form as between fed and fasted states, the dosage form is characterized as being substantially free from a food effect (e.g., co-administration with food may still have an effect on the maximal plasma concentration of the methylphenidate active agent).

The controlled release carrier systems used to produce the oral dosage forms of the present invention can characterized as: (i) having a food effect (administration of the dosage form with food will have a significant effect on both the rate and extent of absorption of methylphenidate from the dosage form, i.e., the rate of absorption is decreased and the extent of absorption is increased); (ii) having a consistent food effect (administration of the dosage form with food will effect both the rate and extent of absorption of methylphenidate from the dosage form; however, there is not a significant difference or variability in this food effect as between different types of meals or diets); or (iii) substantially free from a food effect (administration of the dosage form with or without food does not significantly effect both the rate to maximal plasma concentration, or $T_{max}$ and the extent of absorption of the methylphenidate active agent, or AUC, although co-administration with food may still have an effect on the maximal plasma concentration, or $C_{max}$, of the methylphenidate active agent).

Accordingly, as used herein, "absence from food effect" means that the ratio of mean AUC fed/fasted is within the accepted 80% to 125% bioequivalence limits for pharmaceutical dosage forms, and the ratio of mean $T_{max}$ fed/fasted is likewise within the accepted 80% to 125% bioequivalence limits. In addition, as used herein, "enhanced in vivo absorption" means that the ratio of mean AUC fed/fasted is at least greater than the 125% upper bioequivalence limit and the ratio of mean $T_{max}$ fed/fasted is greater than the 125% upper bioequivalence limit. As used herein, a "consistent food effect" means that there is enhanced in vivo absorption and the ratio of mean AUC fed high-fat/fed low-fat is within the accepted 80% to 125% bioequivalence limits for pharmaceutical dosage forms, and the ratio of mean $T_{max}$ fed/fasted is likewise within the accepted 80% to 125% bioequivalence limits. By "C" is meant the concentration of methylphenidate in the blood plasma of a subject, generally expressed as mass per unit volume, typically nanograms per milliliter. By "$C_{max}$" is meant the maximum concentration of methylphenidate in the blood plasma of a subject, generally expressed as mass per unit volume, typically nanograms per milliliter, within a specified time interval "T" after administration of the methylphenidate to a subject, or "$T_{max}$". As used herein, "fasted" means that, under a clinical trial setting, a dosage form is administered to a subject that has fasted overnight for at least 10 hours, fasted for an additional 4 hours after dosage administration, and then received a standardized high-fat (breakfast) meal. As used herein, "fed" means that, under a clinical trial setting, a dosage form is administered to a subject immediately after having ingested a high-fat or low-fat standardized meal. A "high-fat" standardized meal consists of 2 slices of toasted white bread spread with butter, two eggs fried in butter, two slices of bacon, 2 oz hash-browned potatoes, and 8 oz whole milk (approximately 33 g protein, 58 to 75 g fat, 58 g carbohydrate, 870 to 1020 calories). A "low-fat" standardized meal consists of one slice of toasted white bread spread with butter or jelly, 1 oz dry cereal (corn flakes), 8 oz skim milk, 6 oz orange juice, and one banana (approximately 17 g protein, 8 g fat, 103 g carbohydrate, 583 calories). All of the above-described pharmacokinetic values can be readily determined by the skilled person using established in vivo clinical trail procedures such as those described below in Example 5, below. Reference may also be made to "Guidance for Industry", Food-Effect Bioavailability and Fed Bioequivalence Studies, US Dept Health and Human Services, FDA, Center for Drug Evaluation and Research (CDER), December 2002.

The methylphenidate can be present in the formulations used to make the dosage forms of the present invention in a neutral form, as a free base form, or in the form of a pharmaceutically acceptable salt. The term "pharmaceutically acceptable salt," as used herein, intends those salts that retain the biological effectiveness and properties of neutral active agents and are not otherwise unacceptable for pharmaceutical use. Pharmaceutically acceptable salts include salts of acidic or basic groups. Pharmaceutically acceptable acid addition salts suitable for use herein are those that form non-toxic acid addition salts, i.e., salts comprising pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Suitable base salts can be formed from bases which form non-toxic salts, for example, aluminium, calcium, lithium, magnesium, potassium, sodium, zinc and diethanolamine salts. See, e.g., Berge et al. (1977) *J. Pharm. Sci.* 6:1-19.

In the controlled release oral dosage forms of the present invention, the methylphenidate will be dissolved (fully or partially) or dispersed within the controlled release carrier system. The phrase "dissolved or dispersed" is intended to encompass all means of establishing a presence of the methylphenidate active agent in the subject controlled release carrier system and includes dissolution, dispersion, partial dissolution and dispersion, and/or suspension and the like. In addition, in certain embodiments of the invention wherein the methylphenidate is in a solid particulate form suspended within the controlled release carrier system, the methylphenidate particulate may be pre-treated with a micronization process to provide a particle population having a substantially homogenous particle size the bulk of which fall within the micron (µm) range.

The methylphenidate will be present in the formulation used to make the present dosage forms in an amount of from about 95 to about 0.1 percent by weight relative to the total weight of the formulation (wt %), in an amount of from about 40 to 1 wt %, in an amount of from about 35 to 1.3 wt %, or in an amount of about 30 to 5 wt %, depending upon the he desired dose required for the dosage form, and the intended use thereof. In certain preferred embodiments, the methylphenidate is present in the formulation in an amount of about 1 to about 10 wt %, and can thus be loaded into a suitable dosage form to provide single dosages ranging from about 0.01 mg to 1000 mg, or from about 0.1 mg to 500 mg, or from about 2 mg to 250 mg, or from about 2 mg to 250 mg, or from about 2 mg to 150 mg, or from about 5 mg to 100 mg, or from about 5 mg to 80 mg. 10, 12, 15, 20, 24, 25, 30, 35, 36, 40, 45, 48 and 60 mg single doses are preferred. The precise amount of methylphenidate desired can be determined by routine methods well known to pharmacological arts.

In addition, the controlled release oral dosage forms of the present invention may be formulated to provide multi-phase (e.g., bimodal) delivery kinetics, for example by the provision of two different components in a single dosage form, one providing an early drug delivery phase and the second, an extended drug delivery phase. This can be achieved in liquid CR carrier systems using, for example, two different formulations in a single dosage form (such as a liquid or solid core formulation placed within a second liquid formulation in a gel cap, or as a capsule containing a liquid or solid formulation placed with a second capsule containing a second formulation, or as a dual compartment dosage form). For particulate CR Carrier systems, this can be achieved using, for example, a capsule containing two different populations of particles, one in immediate release form the other in a delayed release form (see, e.g, U.S. Pat. No. 6,344,215 to Bettman et al.), or as two different populations of particle sizes of the same formulation.

The controlled release oral dosage forms of the present invention may be produced using any suitable oral controlled release system known in the art. Accordingly, in certain embodiments, the dosage forms of the present invention are formulated into dosage forms administrable to patients in need thereof. Specific controlled release dosage forms and methods of using the same will now be described. It will be appreciated that the specific controlled release dosage forms described below are merely exemplary.

Osmotic CR Carrier Systems

In an embodiment, osmotic CR carrier systems can be used to practice the present invention (to provide osmotic dosage forms). Osmotic dosage forms in general utilize osmotic pressure to generate a driving force for imbibing fluid into a compartment formed, at least in part, by a semipermeable membrane that permits free diffusion of fluid but not drug or osmotic agent(s), if present. A significant advantage to osmotic systems is that operation is pH-independent and thus continues at the osmotically determined rate throughout an extended time period even as the dosage form transits the gastrointestinal tract and encounters differing microenvironments having significantly different pH values. A review of such dosage forms can be found in: Santus et al (1995) *Journal of Controlled Release* 35:1-21. In addition, U.S. Pat. Nos. 3,845,770; 3,916,899; 3,995,631; 4,008,719; 4,111,202; 4,160,020; 4,327,725; 4,578,075; 4,681,583; 5,019,397 and 5,156,850 each disclose osmotic devices for the continuous dispensing of active agent Osmotic dosage forms in which a drug composition is delivered as a slurry, suspension or solution from a small exit orifice by the action of an expandable layer are disclosed in U.S. Pat. Nos. 5,633,011; 5,190,765; 5,252,338; 5,620,705; 4,931,285; 5,006,346; 5,024,842; and 5,160,743. Typical devices suitable for use in the practice of the invention include an expandable push layer and a drug layer surrounded by a semipermeable membrane. An example of an osmotic methylphenidate dosage form exhibiting a substantially ascending release rate profile is Concerta which is designed to deliver the active agent at a substantially ascending rate of release for up to about 8 hours.

One preferred embodiment of controlled release dosage form for use herein comprises an osmotic controlled release dosage form, which is disclosed for instance in published US Patent Publication No. 2005/0208132. A first drug layer comprises osmotically active components, and a lower amount of active agent than in second drug layer. The osmotically active component(s) in the first component drug layer comprises an osmagent such as salt and one or more osmopolymer(s) having relatively small molecular weights which exhibit swelling as fluid is imbibed such that release of these osmopolymers through an exit occurs. Additional excipients such as binders, lubricants, antioxidants and colorants may also be included in the first drug layer.

The second drug layer comprises active agent in an admixture with selected excipients adapted to provide an osmotic activity gradient for driving fluid from an external environment through the membrane and for forming a deliverable drug formulation upon imbibition of fluid. The excipients may include a suitable suspending agent, but no osmotically active agent "osmagent" such as salt, sodium chloride. It has been discovered that the omission of salt from this second drug layer, which contains a higher proportion of the overall drug in the dosage form, in combination with the salt in the first drug layer, provides an ascending rate of release creating a longer duration of ascending rate.

The drug layers used in such dosage forms further comprise a hydrophilic polymer carrier. The hydrophilic polymer provides a particle in the drug composition that contributes to the controlled delivery of the active drug. Representative examples of these polymers are poly(alkylene oxide) of 100,000 to 750,000 number-average molecular weight, including poly(ethylene oxide), poly(methylene oxide), poly(butylene oxide) and poly(hexylene oxide); and a poly(carboxymethylcellulose) of 40,000 to 400,000 number-average molecular weight, represented by poly(alkali carboxymethylcellulose), poly(sodium carboxymethylcellulose), poly(potassium carboxymethylcellulose) and poly(lithium carboxymethylcellulose). The drug layers may be formed from particles by comminution that produces the size of the drug and the size of the accompanying polymer used in the fabrication of the drug layer, typically as a core containing the compound.

The ratio of drug concentration between the first drug layer and the second drug layer alters the release rate profile. Release rate profile is calculated as the difference between the maximum release rate and the release rate achieved at the first time point after start-up (for example, at 6 hours), divided by the average release rate between the two data points.

The membrane is formed to be permeable to the passage of an external fluid, such as water and biological fluids, and is substantially impermeable to the passage of osmagent, osmopolymer and the like. As such, it is semipermeable. The selectively semipermeable compositions used for forming the membrane are essentially nonerodible and substantially insoluble in biological fluids during the life of the dosage form. The cellulosic polymers typically have a degree of substitution, "D.S.", on their anhydroglucose unit from greater than 0 up to 3 inclusive. The semipermeable compositions typically include a member selected from the group consisting of cellulose acylate, cellulose diacylate, cellulose triacylate, cellulose triacetate, cellulose acetate, cellulose diacetate, cellulose triacetate, mono-, di- and tri-cellulose alkanylates, mono-, di-, and tri-alkenylates, mono-, di-, and tri-aroylates, and the like.

The push layer comprises an expandable layer in contacting layered arrangement with the second drug layer. The push layer comprises a polymer that imbibes an aqueous or biological fluid and swells to push the drug composition through the exit of the device. An immediate release drug coating may be provided on the surface of the dosage form in circumstances where quick drug release is desired.

Pan coating may be conveniently used to provide such dosage forms, except for the exit orifice. In the pan coating system, the wall-forming composition for the inner wall or the outer wall, as the case may be, is deposited by successive spraying of the appropriate wall composition onto the compressed trilayered or multilayered core comprising the drug layers, optional barrier layer and push layer, accompanied by tumbling in a rotating pan. One or more exit orifices are drilled in the drug layer end of the dosage form, and optional water soluble overcoats, which may be colored (e.g., Opadry colored coatings) or clear (e.g., Opadry Clear), may be coated on the dosage form to provide the finished dosage form. Drilling, including mechanical and laser drilling, through the semipermeable wall can be used to form the exit orifice. Such exits and equipment for forming such exits are disclosed in U.S. Pat. Nos. 3,916,899 and 4,088,864.

Liquid CR Carrier Systems

An alternative controlled release carrier system suitable for use herein is a liquid controlled release dosage form as described in U.S. Pat. No. 4,961,932. While this patent discloses multiple embodiments useful in the practice of the present invention, a preferred embodiment is as follows. The preferred embodiment comprises a plurality of tiny pills that release a drug by osmotic principles. The tiny pills comprise a wall that releases a beneficial agent, such as a drug, by the process of osmotic bursting over time. The drug is present in the form of an osmotic solute, such as a therapeutically acceptable salt, that exhibits an osmotic pressure gradient across the wall against distilled water, or the drug can be mixed with an osmotically effective solute that exhibits an osmotic pressure gradient across the wall against distilled water. The tiny pills are placed in a fluidic means that comprises a concentration substantially equal to or larger than the concentration of the drug in the tiny pills thereby providing an initial concentration gradient substantially equal to zero. The wall forming composition used to manufacture the wall comprises those materials permeable to the passage of an external fluid present in an environment of use and substantially impermeable to the passage of drug and osmotic solute. Typical materials include a member selected from the group consisting of cellulose acylate, cellulose diacylate, cellulose triacylate, cellulose acetate, cellulose diacetate, cellulose triacetate, cellulose acetate having a degree of substitution "D.S." of up to 1 and an acetyl content of 21%; cellulose diacetate having a D.S. of 1 to 2 and an acetyl content of 21% to 35%; cellulose triacetate having a D.S. of 2 to 3 and an acetyl content of 35% to 44.8%, cellulose acetate propionate, cellulose acetate butyrate, ethyl cellulose semipermeable polyurethane, and the like. The osmotic wall can be coated around the drug in varying thicknesses by pan coating, spray-coating, Wurster™ fluid air-suspension coating, coacervation techniques, and the like. The wall is applied using organic solvents such as methylene chloride-methanol, methylene chloride-acetone, methanol-acetone, ethylene dichloride-acetone, and the like. Osmotic wall forming materials, and procedures for forming the wall, and osmotic bursting procedures are disclosed in U.S. Pat. Nos. 2,799,241; 3,952,741; 4,014,334; and 4,016,880. The drug, neat, or a combination of the drug and an osmotically effective solute in the tiny pills typically has a particle size of 0.1 to 1000 micron, and a presently preferred particle size of about 0.5 to 300 microns, average.

Particulate CR Carrier Systems

In certain other alternative embodiments, the methylphenidate is provided in a particulate controlled release carrier system, wherein it is incorporated into or onto a substrate and a controlled release coating is applied thereto. For example, the methylphenidate may be contained within or on a substrate as follows: (i) incorporated into matrix spheroids (e.g., together with a pharmaceutically acceptable spheronizing agent such as microcrystalline cellulose), (ii) coated onto inert pharmaceutically acceptable beads (e.g., nonpareil beads); (iii) incorporated into a normal release tablet core; or (iv) incorporated into a tablet core which comprises a matrix including a controlled release carrier material. Thereafter, a controlled release coating is applied onto substrates such as those mentioned in (i)-(iv) above. The dosage forms of the present invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release the drug in desired areas of the gastro-intestinal (GI) tract, e.g., the stomach or small intestine. When a pH-independent coating is desired, the coating is designed to achieve optimal release regardless of pH-changes in the environmental fluid, e.g., the GI tract. It is also possible to formulate compositions that release a portion of the methylphenidate dose in one desired area of the GI tract, e.g., the stomach, and release the remainder of the dose in another area of the GI tract, e.g., the small intestine.

Formulations according to the invention that utilize pH-dependent coatings may also impart a repeat-action effect whereby unprotected methylphenidate is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropytmethylcellulose phthalate, and methacrylic acid ester copolymers, zein, and the like.

In certain preferred embodiments, the substrate (e.g., tablet core bead, matrix particle) comprising the methylphenidate is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a targeted controlled release profile as described herein. Such formulations are described, e.g., in detail in U.S. Pat. Nos. 5,273,760 and 5,286,493. The particles are preferably film-coated with a material that permits release of the methylphenidate so as to achieve, in combination with the other stated properties the desired in vitro release rate and in vivo plasma levels as determined using the teaching of the present invention. The controlled release coating formulations of the present invention should be capable of producing a strong, continuous film that is smooth and elegant, capable of supporting pigments and other coating additives, non-toxic, inert, and tack-free.

Other examples of controlled release formulations and coatings that may be used in accordance with the present invention include those described in U.S. Pat. Nos. 5,324,351; 5,356,467, and 5,472,712.

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially available aqueous dispersion of ethylcellulose is the Aquacoat brand (FMC Corp., Philadelphia, Pa., U.S.A.). Aquacoat is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat with a suitable plasticizer prior to use.

Another aqueous dispersion of ethylcellulose is commercially available as Surelease brand (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

The hydrophobic material comprising the controlled release coating may comprise a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly (methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described as fully polymerized copolymers of acrylic and methacrylic acid esters with a low content of quaternary ammonium groups.

In order to obtain a desirable in vitro or in vivo dissolution profile in the practice of the invention, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings that may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit brand (Rohm Tech, Inc.). There are several different types of Eudragit polymers. For example, Eudragit "E" is an example of a methacrylic acid copolymer which swells and dissolves in acidic media. Eudragit "L" is a methacrylic acid copolymer which does not swell at about pH<5.7 and is soluble at about pH>6. Eudragit "S" does not swell at about pH<6.5 and is soluble at about pH>7. Eudragit "RL" and Eudragit "RS" are water swellable, and the amount of water absorbed by these polymers is pH-dependent, however, dosage forms coated with Eudragit "RL" and "RS" are pH-independent.

In certain preferred embodiments, the acrylic coating comprises a mixture of two acrylic resin lacquers commercially available from Rohm Pharma under the Tradenames Eudragit "RL30D" and Eudragit "RS30D", respectively. Eudragit "RL30D" and "RS30D" are copolymers of acrylic and methacrylic esters with a low content of quaternary ammonium groups, the molar ratio of ammonium groups to the remaining neutral (meth)acrylic esters being 1:20 in Eudragit "RL30D" and 1:40 in Eudragit "RS30D". The mean molecular weight is about 150,000. The code designations RL (high permeability) and RS (low permeability) refer to the permeability properties of these agents. Eudragit RL/RS mixtures are insoluble in water and in digestive fluids. However, coatings formed from the same are swellable and permeable in aqueous solutions and digestive fluids.

Eudragit RL/RS dispersions used in the practice of the present invention may be mixed together in any desired ratio in order to ultimately obtain a controlled release formulation having a desirable dissolution profile. Desirable controlled release formulations may be obtained, for instance, from a retardant coating derived from 100% Eudragit RL, 50% Eudragit RL and 50% Eudragit RS, and 10% Eudragit RL: 90% Eudragit RS. Of course, one skilled in the art will recognize that other acrylic polymers may also be used, such as, for example, Eudragit L.

In embodiments of the present invention where the coating comprises an aqueous dispersion of a hydrophobic material such as an alkylcellulose or an acrylic polymer, the inclusion of an effective amount of a plasticizer in the aqueous dispersion of hydrophobic material will further improve the physical properties of the controlled release coating. For example, because ethylcellulose has a relatively high glass transition temperature and does not form flexible films under normal coating conditions, it is preferable to incorporate a plasticizer into an ethylcellulose coating containing controlled release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for aqueous dispersions of ethyl cellulose.

Examples of suitable plasticizers for the acrylic polymers used in the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit RL/RS lacquer solutions include polyethylene glycols, propylene glycol, diethyl phthalate, castor oil, and triacetin. Triethyl citrate is an especially preferred plasticizer for aqueous dispersions of ethyl cellulose.

It has further been found that the addition of a small amount of talc reduces the tendency of the aqueous dispersion to stick during processing, and acts as a polishing agent.

When the aqueous dispersion of hydrophobic material is used to coat a substrate including the methylphenidate, for example, inert pharmaceutical beads such as nonpariel 18/20 beads, a plurality of the resultant stabilized solid controlled release beads may thereafter be placed in a gelatin capsule in an amount sufficient to provide an effective controlled release oral dosage form when ingested and contacted by an environmental fluid, e.g., gastric fluid or dissolution media. Alternatively, the substrate may be a tablet core coated with the controlled release coating, and optionally a further film-forming agent or colorant, such as Opadry brand (Colorcon, Inc).

In formulations where an aqueous dispersion of an hydrophobic polymer such as an alkylcellulose is applied to the substrate, it is preferred that the coated substrate is cured at a temperature above the glass transition temperature of the plasticized polymer and at a relative humidity above ambient conditions, until an endpoint is reached at which the coated formulation attains a dissolution profile which is substantially unaffected by exposure to storage conditions, e.g., of elevated temperature and/or humidity. Generally, in such formulations the curing time is about 24 hours or more, and the curing conditions may be, for example, about 60° C. and 85% relative humidity. Detailed information concerning the stabilization of such formulations is set forth in U.S. Pat. Nos. 5,273,760; 5,681,585; and 5,472,712.

In formulations where an aqueous dispersion of an acrylic polymer is applied to the substrate, it is preferred that the coated substrate is cured at a temperature above the glass transition temperature of the plasticized polymer until an endpoint is reached at which the coated formulation attains a dissolution profile which is substantially unaffected by exposure to storage conditions, e.g., of elevated temperature and/or humidity. Generally, the curing time is about 24 hours or more, and the curing temperature may be, for example, about 45° C. Detailed information concerning the stabilization of such formulations is set forth in U.S. Pat. Nos. 5,286,493; 5,580,578; and 5,639,476.

The controlled release profile of the coated formulations of the invention can be altered, for example, by varying the amount of overcoating with the aqueous dispersion of hydrophobic material, altering the manner in which the plasticizer is added to the aqueous dispersion of hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with methylphenidate are prepared, e.g., by dissolving the methylphenidate in water and then spraying the solution onto a substrate, for example, nonpariel 18/20 beads, using a Wuster insert. Optionally, additional ingredients are also added prior to coating the beads in order to assist the binding of the methylphenidate to the beads, and/or to color the solution, etc. For example, a product which includes hydroxypropylmethylcellulose, etc., with or without colorant e.g., Opadry, may be added to the solution and the solution mixed (e.g., for about 1 hour) prior to application of the same onto the beads. The resultant coated substrate, in this example beads, may then be optionally overcoated with a barrier agent, to separate the methylphenidate from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Pre-formulated aqueous dispersions of ethyl-cellulose, such as Aquacoat or Surelease brands, may be used. If Surelease is used, it is not necessary to separately add a plasticizer. Alternatively, pre-formulated aqueous dispersions of acrylic polymers such as Eudragit can be used.

The coating solutions preferably contain, in addition to the film-former, plasticizer, and solvent system (i.e., water), a colorant to provide elegance and product distinction. Color may be added to the solution of the methylphenidate instead, or in addition to the aqueous dispersion of hydrophobic material. For example, color can be added to Aquacoat via the use of alcohol or propylene glycol based color dispersions, milled aluminum flakes and opacifiers such as titanium dioxide by adding color with shear to water soluble polymer solution and then using low shear to the plasticized Aquacoat. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retarding effect of the coating.

The plasticized aqueous dispersion of hydrophobic material may be applied onto the substrate comprising the methylphenidate by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic material to obtain a predetermined sustained release of the methylphenidate when the coated substrate is exposed to aqueous solutions, e.g. gastric fluid, is preferably applied, taking into account the physical characteristics of the methylphenidate active agent, the manner of incorporation of the plasticizer, etc. After coating with the hydrophobic material, a further overcoat of a film-former, such as Opadry, is optionally applied to the beads. This overcoat is provided, if at all, in order to substantially reduce agglomeration of the beads.

The release of methylphenidate from the sustained release formulation of the present invention can be further influenced, i.e., adjusted to a desired rate, by the addition of one or more release-modifying agents, or by providing one or more passageways through the coating. The ratio of hydrophobic material to water-soluble material is determined by, among other factors, the release rate required and the solubility characteristics of the materials selected.

The release-modifying agents that function as pore-formers may be organic or inorganic, and include materials that can be dissolved, extracted or leached from the coating in the environment of use. The pore-formers may comprise one or more hydrophilic materials such as hydroxypropylmethylcellulose.

The controlled release coatings of the present invention can also include erosion-promoting agents such as starch and gums.

The controlled release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The controlled release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864. The passageway can have any shape such as round, triangular, square, elliptical, irregular, etc.

The substrate used in the practice of the present invention may be prepared by a spheronizing agent together with the methylphenidate that can be spheronized to form spheroids. Microcrystalline cellulose is preferred. A suitable microcrystalline cellulose is, for example, the material sold as Avicel PH 101 (FMC Corporation). In such embodiments, in addition to the methylphenidate and spheronizing agent, the spheroids may also contain a binder. Suitable binders, such as low-viscosity, water-soluble polymers, will be well known to those skilled in the pharmaceutical art. However, water-soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer or ethyl cellulose. In such embodiments, the controlled release coating will generally include a water insoluble material such as (a) a wax, either alone or in admixture with a fatty alcohol; or (b) shellac or zein.

In one embodiment of the invention, the controlled release methylphenidate formulation is prepared as a multilayered release (MLR) formulation comprising coated inert beads. A summary of one method of manufacturing such a formulation is outlined as follows. First, immediate release (IR) methylphenidate beads are prepared by spraying a solution of methylphenidate in water over sugar beads in a fluid bed dryer with a drug load of about 8%. The spray process is carried out in a fluid bed dryer, equipped with a Wurster column. A clear overcoat of HPMC is applied using an Opadry material (e.g., Opadry Clear (Formula No: YS-1-7006)), to a weight gain of about 1%. Next, a controlled release coating is applied to the IR beads, which converts the same into controlled release (CR) beads. This is accomplished by spraying a solution of Eudragit RS 30 D, triethyl citrate (plasticizer) and talc (glidant), onto the IR beads. Next, the coated beads are cured in order to obtain a stabilized release rate of the methylphenidate. In preferred embodiments of the present invention where the CR coating utilizes an acrylic resin to control the release of the methylphenidate, the CR beads at this stage are subjected to oven curing at a temperature above the Tg of the plasticized acrylic polymer of the required time period, the optimum values of the temperature and time for the particular formulation being determined experimentally. In certain embodiments of the present invention, the stabilized product is obtained via oven curing conducted at a temperature of about 40-50° C. for a time period of about 12 to about 24 hours or longer. An enteric coating is then applied onto the CR beads to convert the same into enteric coated CR (ECCR) beads. This is accomplished by spraying a solution of Eudragit L 30 D-55 dispersion, triethyl citrate (plasticizer) and talc (glidant) onto the CR beads. Finally, an immediate release coating is applied onto the ECCR beads (referred to as, e.g., an IR Topcoat). This is accomplished by spraying a solution of methylphenidate in water over EC CR beads.

Matrix CR Carrier Systems

In certain preferred embodiments of the present invention, the controlled release oral dosage form is produced using a formulation that comprises a matrix controlled release carrier system including the methylphenidate and a controlled release carrier material (which may comprise one or more hydrophobic materials, such as an alkylcellulose and/or an acrylic polymer as previously defined herein). The materials suitable for inclusion in a controlled release matrix will depend on the method used to form the matrix.

Suitable materials for inclusion in the controlled release matrices of the invention, in addition to methylphenidate, include:

(A) hydrophilic and/or hydrophobic materials, such as gums; alkylcelluloses; cellulose ethers, including hydroxyalkylcelluloses and carboxyalkylcelluloses; acrylic resins, including all of the acrylic polymers and copolymers discussed above, and protein-derived materials. This list is not meant to be exclusive, and any pharmaceutically acceptable hydrophobic material or hydrophilic material that is capable of imparting the desired controlled release profile of methylphenidate is meant to be included herein. The dosage form may comprise, e.g., from about 1% to about 80% by weight of such material.

In certain embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxy-ethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing. In yet other embodiments, the hydrophobic material is an alkylcellulose.

(B) digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural or synthetic waxes, polyhydric alcohols, including polyalkylene glycols. The oral dosage form may contain up to 60% (by weight) of such material. In certain embodiments, a combination of two or more hydrocarbon materials are included in the matrix formulations. If an additional hydrocarbon material is included, it is preferably selected from natural and synthetic waxes, fatty acids, fatty alcohols, and mixtures of the same.

Preferred hydrocarbons are water-insoluble with more or less pronounced hydrophilic and/or hydrophobic trends, and have a melting point from about 30° C. to about 200° C., preferably from about 45° C. to about 90° C.

For purposes of the present invention, a wax-like substance is defined as any material that is normally solid at room temperature and has a melting point of from about 30° C. to about 100° C. Suitable waxes include, for example, beeswax, glycowax, castor wax and carnauba wax.

Aliphatic alcohols used in the above compostions may be, for example, lauryl alcohol, myristyl alcohol or stearyl, cetyl and/or cetostearyl alcohol. The amount of aliphatic alcohol, if included in the present controlled oral dosage forms, will be determined, as above, by the precise rate of methylphenidate release required. In certain embodiments, the oral dosage form contains between 20% and 50% (by wt) aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/polyalkylene glycol used in the controlled release formulation determines, to a considerable extent, the release rate of the methylphenidate from the dosage form.

Suitable polyalkylene glycols include, for example, polypropylene glycol or polyethylene glycol. The number average molecular weight of the at least one polyalkylene glycol is preferred between 1,000 and 15,000 especially between 1,500 and 12,000.

In addition to the above ingredients, a controlled release matrix may also contain suitable quantities of other materials, e.g. diluents, lubricants, binders, granulating aids, colorants, flavorants and glidants that are conventional in the pharmaceutical art.

In order to facilitate the preparation of a solid controlled release oral dosage form according to this invention, any method of preparing a matrix formulation known to those skilled in the art may be used. For example incorporation in the matrix may be effected, for example, by (a) forming granules comprising at least one water-soluble hydroxyalkyl cellulose and methylphenidate; (b) mixing the hydroxyalkyl cellulose containing granules with at least one $C_2$-$C_{36}$ aliphatic alcohol; and (c) optionally, compressing and shaping the granules. Preferably, the granules are formed by wet granulating the hydroxyalkyl cellulose/methylphenidate with water. In a particularly preferred embodiment of this process, the amount of water added during the wet granulation step is preferably between 1.5 and 5 times, especially between 1.75 and 3.5 times, the dry weight of the methylphenidate.

In yet other alternative embodiments, a spheronizing agent, together with the methylphenidate can be spheronized to form spheroids. Microcrystalline cellulose is preferred. A suitable microcrystalline cellulose is, for example, the material sold as Avicel PH 101 (FMC Corporation). In such embodiments, in addition to the methylphenidate and spheronizing agent, the spheroids may also contain a binder. Suitable binders, such as low viscosity, water-soluble polymers, will be well known to those skilled in the pharmaceutical art. However, water-soluble hydroxy lower alkyl celluloses, such as hydroxypropylcellulose, are preferred. Additionally (or alternatively) the spheroids may contain a water-insoluble polymer, especially an acrylic polymer, an acrylic copolymer, such as a methacrylic acid-ethyl acrylate copolymer, or ethyl cellulose. In such embodiments, the controlled release coating will generally include a hydrophobic material such as a wax, either alone or in admixture with a fatty alcohol; or shellac or zein.

Melt-Extrusion Matrix CR Carrier Systems

In certain other embodiments of the present invention, the controlled release matrices used in the dosage form may be prepared via melt-granulation or melt-extrusion techniques. Such formulations are described in U.S. Pat. Nos. 5,965,161 and 5,958,452. Generally, melt-granulation techniques involve melting a normally solid hydrophobic material, e.g. a wax, and incorporating a powdered drug therein. To obtain a controlled release dosage form, it may be necessary to incorporate an additional hydrophobic substance, e.g. ethylcellulose or a water-insoluble acrylic polymer, into the molten wax hydrophobic material. Examples of controlled release formulations prepared via melt-granulation techniques are found in U.S. Pat. No. 4,861,598.

The additional hydrophobic material may comprise one or more water-insoluble wax-like thermoplastic substances possibly mixed with one or more wax-like thermoplastic substances being less hydrophobic than said one or more water-insoluble, wax-like substances. In order to achieve constant release, the individual wax-like substances in the formulation should be substantially non-degradable and insoluble in gastrointestinal fluids during the initial release phases. Useful water-insoluble, wax-like substances may be those with a water-solubility that is lower than about 1:5,000 (w/w).

In addition to the above ingredients, a controlled release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation. In addition to the above ingredients, a controlled release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the Handbook of Pharmaceutical Excipients, American Pharmaceutical Association (1986).

The preparation of a suitable melt-extruded controlled release matrix according to the present invention may, for example, include the steps of blending the methylphenidate together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides controlled release of the therapeutically active agent for up to about 24 hours. The multiparticulates may be divided into unit doses via placement into a gelatin capsule, or may be compressed into a suitable tablet form.

An optional process for preparing the melt extrusions includes directly metering into an extruder a hydrophobic material, the methylphenidate, and an optional binder, heating the homogenous mixture; extruding the homogenous mixture to thereby form strands; cooling the strands containing the homogeneous mixture; cutting the strands into particles having a size from about 0.1 mm to about 12 mm; and dividing said particles into unit doses.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

Melt extruded multiparticulate systems can be provided in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing methylphenidate and one or more excipients, preferably including a hydrophobic material as described above. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one particular embodiment, controlled release oral dosage forms are prepared to include an effective amount of melt-extruded multiparticulates within a capsule. For example, a plurality of the melt-extruded multiparticulates may be placed in a gelatin capsule in an amount sufficient to provide an effective controlled release dose when ingested and contacted by gastric fluid.

In another embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in Remington's Pharmaceutical Sciences, (Arthur Osol, editor), 1553-1593 (1980).

In yet another embodiment, the extrudate can be shaped into tablets as set forth in U.S. Pat. No. 4,957,681.

Optionally, the controlled release melt-extruded multiparticulate systems or tablets can be coated, or the gelatin capsule can be further coated, with a controlled release coating such as the controlled release coatings described above. Such coatings preferably include a sufficient amount of hydrophobic material to obtain a weight gain level from about 2 to about 30 percent, although the overcoat may be greater.

The melt-extruded unit dosage forms of the present invention may further include combinations of melt-extruded multiparticulates containing methylphenidate before being encapsulated. Furthermore, the unit dosage forms can also include an amount of an immediate release methylphenidate for prompt therapeutic effect. The immediate release methylphenidate may be incorporated, e.g., as separate pellets within a gelatin capsule, or may be coated on the surface of the multiparticulates after preparation of the dosage forms (e.g., controlled release coating or matrix-based). The unit dosage forms of the present invention may also contain a combination of controlled release beads and matrix multiparticulates to achieve a desired effect.

In other embodiments, the melt-extruded material is prepared without the inclusion of the methylphenidate, which is added thereafter to the extrudate. Such formulations typically will have the methylphenidate blended together with the extruded matrix material, and then the mixture would be tableted in order to provide a slow release formulation.

The substrates of the present invention may be also be prepared via a melt pelletization technique. In such circumstances, the methylphenidate in finely divided form is combined with a binder (also in particulate form and other optional inert ingredients, and thereafter the mixture is pelletized, e.g., by mechanically working the mixture in a high shear mixer to form the pellets (granules, spheres). Thereafter, the pellets (granules, spheres) may be sieved in order to obtain pellets of the requisite size. The binder material is preferably in particulate form and has a melting point above about 40° C. Suitable binder substances include, for example, hydrogenated castor oil, hydrogenated vegetable oil, other hydrogenated fats, fatty acid esters, fatty acid glycerides, and the like.

In accordance with the present invention, all of the above-described controlled release oral methylphenidate dosage forms (formed using Osmotic Controlled Release (CR) carrier systems, Liquid CR carrier systems, Particulate CR carrier systems, CR Matrix carrier systems and CR Melt-Extrusion Matrix carrier systems) may be formulated so as to produce targeted plasma levels of methylphenidate over a particular period. This is obviously of great importance in maintaining a methylphenidate plasma level within an appropriate therapeutic range to provide: (i) an initial increasing in vivo rate of release of methylphenidate from the controlled release system suitable to provide an initial increasing-rate phase of less than or equal to about 2 hours, and sufficient to provide a therapeutically effective amount of methylphenidate for a rapid onset of action; (ii) a second, zero-order or decreasing (i.e., non-ascending) in vivo rate of release of methylphenidate from the controlled release system that provides a subsequent zero order- or decreasing-rate phase sufficient to provide a therapeutically effective amount of methylphenidate through at least about 11 to 12 hours post administration; and (iii) a single $T_{max}$ of about 5.5 to 7.5 hours post administration. The exact time to maximum plasma concentration may be adjusted by adjusting various components of the controlled release carrier system as taught herein. The novel and unique in vivo methylphenidate release kinetics provided by the oral controlled release dosage forms of the present invention are sufficient to provide the methylphenidate in vivo PK profile depicted in FIG. 7.

Once per day (QD) is typically used to maintain a sufficient clinical effect, e.g., to treat ADD or ADHD. Other dosage regimens may be determined by a physician in accordance with standard practices.

Abuse-Resistant Controlled Release Systems

In U.S. Patent Publication No. US 2004/0161382, hereinafter referred to as the "382 Publication", certain pharmaceutical dosage forms and drug-delivery devices suitable for oral delivery of pharmacologically active agents are described. These novel dosage forms and devices feature a unique combination of pharmaceutical excipients including an HVLCM, a network former, and an optional rheology modifier and/or a solvent that together provide a controlled release carrier system. The controlled release carrier system is loaded with an active agent of interest, and will release the same over a period of time when in an aqueous environment, and in particular, an environment similar to that of the GI tract of a mammal. The controlled release carrier system can further provide the added benefit of enhanced abuse-resistance, wherein the carrier system resists various physical disruption and other in vitro extraction techniques (e.g., extraction into ethanol, water or other common solvents) that could be employed by someone wishing to disable the controlled release function of the system to access substantially all or most of the sequestered active agent in an immediate release form that can be ingested, inhaled or injected to provide a euphoric effect. The 382 Publication therefore describes a number of controlled release carrier systems that can be used to produce oral dosage forms or delivery devices that provide desirable controlled release kinetics and/or abuse-resistance characteristics.

It is a primary object of the present invention to provide for improved methylphenidate controlled release oral dosage forms, where such improved dosage forms are based upon the controlled release carrier systems described in the 382 Publication. In this regard, there has remained a need in the art to provide a controlled release carrier system that provides all of the benefits of those described in the 382 Publication as well as providing enhanced safety features and/or abuse-resistance properties in addition to enhanced in vivo pharmacological performance. One of the key hindrances facing the skilled person desiring to provide such a controlled release carrier system resides in the very nature of the carrier system itself. More particularly, the unique controlled release carrier system is responsible for in vivo pharmacological performance, where the active agent must be delivered from the system by diffusion from the system as it transits the GI tract. This same controlled release carrier system is also responsible for the in vitro abuse-resistance and in vivo safety performance, that is, the carrier system must prevent active agent from leaving the system when contacted with very efficient aqueous solvents and/or prolonged exposure to aqueous environments having a low or high pH.

Thus, manipulations that can be made to the controlled release system in order to, for example, increase overall delivery efficiency (AUC) or to provide for extended release rates (manipulations designed to increase release of the active agent from the controlled release carrier system) typically will frustrate the in vitro abuse-resistance and in vivo safety performance of that same system. This is because, generally, formulation manipulations that increase $C_{max}$ or decrease $T_{max}$ can frustrate abuse-resistance by allowing more/faster extractability (e.g., changes designed to increase rate/extent of in vivo drug release also increase rate/extent of in vitro drug release when attempts are made to defeat the controlled release mechanism of a dosage form).

The term "AUC" means the area under the curve obtained from an in vive assay in a subject by plotting blood plasma concentration of the active agent in the subject against time, as measured from the time of administration, to a time "T" after administration. The time T will correspond to the delivery period of the active agent to a subject. In like manner, manipulations that can be made to the controlled release system in order to enhance in vitro abuse-resistance and in vivo safety performance (manipulations designed to decrease release of active agent from the controlled release carrier system) typically will frustrate the in vivo pharmacological performance of that same system. As used throughout this specification and the attached claims, the terms "abuse-resistance" and abuse-resistant" are completely interchangeable with the related terms "abuse-deterrence" and "abuse-deterrent", as well as "tamper-resistance" and "tamper-resistant", and thus mean exactly the same thing.

Accordingly, it is a primary object of the invention to provide a controlled release oral pharmaceutical dosage form that comprises methyiphenidate in a controlled release carrier system. The subject dosage form is characterized by: (i) a first, increasing in vivo rate of release of methylphenidate from the controlled release system that provides an initial increasing-rate phase of less than or equal to about 2 hours, and is sufficient to provide a therapeutically effective amount of methylphenidate for a rapid onset of action; (ii) a second, zero-order or decreasing (i.e., non-ascending) in vivo rate of release of methylphenidate from the controlled release system that provides a subsequent zero order- or decreasing-rate phase sufficient to provide a therapeutically effective amount of methylphenidate through at least about 11 to 12 hours post administration; (iii) a single $T_{max}$ of about 5.5 to 7.5 hours post administration; and (iv) the dosage form is abuse-resistant. The novel and unique in vivo methylphenidate release kinetics provided by the abuse-resistant oral dosage forms of the present invention are sufficient to provide the methylphenidate in vivo PK profile depicted in FIG. 7. By "abuse-resistant", herein, it is meant that the dosage form is resistant to extraction in ethanol (80 proof) such that: less than about 50%, preferably less than about 45% and more preferably less than about 25 to 40% of the active agent is extracted after 60 minutes of extraction in ethanol at ambient temperature (RT); and less than about 30%, more preferably less than about 28% and more preferably less than about 25 to 27%6 of the active agent is extracted after 60 minutes of extraction in ethanol at 60° C. By the term "ambient temperature", used interchangeabley herein with "room temperature" and/or "RT", is meant the normal temperature of a working area or laboratory and ranges from about 18 to 25° C., and is more particularly used herein to denote a normal temperature of 25° C. Suitable in vitro test methodology, techniques, apparatus and equipment to determine if a dosage form is properly resistant to extraction in ethanol are described below in Example 3. In certain preferred embodiments, the "abuse-resistant" dosage form is also resistant to extraction in a panel of common household solvents, that is, the dosage form is further resistant to extraction in one or more of the following solvents: hot and cold water; hot tea; cola soft drinks; saturated baking soda solution; vinegar; strong acid (e.g., HCl); and aqueous buffers ranging from pH1 to pH12.

In certain other preferred embodiments of the invention, the abuse-resistant oral pharmaceutical dosage forms comprise a controlled release carrier system that can provide a decreased risk of misuse or abuse. An important advantage of the dosage forms disclosed herein is that they have abuse-resistant characteristics and/or reduced risk of diversion. In this regard, the formulation contained within the dosage form (the controlled release carrier system and the methylphenidate) is neither susceptible to common crushing, pulverization or attrition techniques, nor susceptible to extraction using common household solvents such as ethanol. In addition, the formulation contained within the dosage form (the controlled release carrier system and the methylphenidate) is also not susceptible to common heat extraction techniques (e.g., microwaving), vaporization techniques (e.g., volatilization or smoking), nor injection techniques due to very poor syringeability and/or injectability properties of the formulation.

Specifically, since the abuse-resistant dosage forms of the present invention are provided as a highly viscous liquid, the formulations avoid the possibility of crushing for the purpose of inhalation. However, in a particular aspect of the invention, enhanced safety features can further be provided by the controlled release carrier system. In this regard, the subject dosage forms are characterized as having either one or both of the following enhanced safety features: the controlled release carrier system is characterized by a low in vitro solvent extractability value of the methylphenidate from the dosage form; and/or the carrier system is characterized by the absence of any significant effect on absorption of the methylphenidate from the dosage form upon co-ingestion of the dosage form with ethanol by a subject, or upon chewing (masticating) or holding the tablet within the mouth (buccal cavity) instead of swallowing the dosage form whole as intended. This second feature, so-called "dose-dumping" is of critical concern to regulatory agencies concerned with the safety of potent pharmaceutical agents. This is because, unlike the standard concerns about intentional abuse, a patient may inadvertently take a controlled release dosage form containing a high potency or dangerous active agent with a glass of wine, or a cocktail, or a child may find a dropped capsule and chew the same. If this activity is enough to defeat the controlled release system, the dosage form could be considered unsafe for this important safety reason.

Accordingly, in certain particularly preferred embodiments of the invention, an abuse-resistant oral methylphenidate dosage form is provided that is characterized by: (i) a first, increasing in vivo rate of release of methylphenidate from the controlled release system that provides an initial increasing-rate phase of less than or equal to about 2 hours, and is sufficient to provide a therapeutically effective amount of methylphenidate for a rapid onset of action; (ii) a second, zero-order or decreasing (i.e., non-ascending) in vivo rate of release of methylphenidate from the controlled release system that provides a subsequent zero order- or decreasing-rate phase sufficient to provide a therapeutically effective amount of methylphenidate through at least about 11 to 12 hours post administration; (iii) a single $T_{max}$ of about 5.5 to 7.5 hours post administration; and (iv) the controlled release carrier system provides a decreased risk of misuse or abuse, characterized by the absence of any significant effect on absorption of the methylphenidate from the dosage form upon co-ingestion of the dosage form with ethanol by a subject. The novel and unique in vivo methylphenidate release kinetics provided by the abuse-resistant oral dosage forms of the present invention are sufficient to provide the methylphenidate in vivo PK profile depicted in FIG. 7. The ability of an abuse-resistant oral dosage form to avoid this dose-dumping effect can be assessed using carefully controlled in vivo human clinical trial methods such as those described below in Example 5. By "no significant effect", it is meant that both the $C_{max}$ ratio and the AUC ratio of absorption of the methylphenidate from the dosage form when taken with water, or with 4%, 20% or 40% ethanol is within a range of about 0.8 to 1.2.

In another particularly preferred embodiment of the invention, an abuse-resistant oral methylphenidate dosage form is provided that is characterized by: (i) a first, increasing in vivo rate of release of methylphenidate from the controlled release system that provides an initial increasing-rate phase of less than or equal to about 2 hours, and is sufficient to provide a therapeutically effective amount of methylphenidate for a rapid onset of action; (ii) a second, zero-order or decreasing (i.e., non-ascending) in vivo rate of release of methylphenidate from the controlled release system that provides a subsequent zero order- or decreasing-rate phase sufficient to provide a therapeutically effective amount of methylphenidate through at least about 11 to 12 hours post administration; (iii) a single $T_{max}$ of about 5.5 to 7.5 hours post administration; and (iv) a controlled release carrier system that provides for a decreased risk of misuse or abuse, characterized by a low in vitro solvent extractability value of the methylphenidate from the dosage form. The novel and unique in vivo methylphenidate release kinetics provided by the abuse-resistant oral dosage forms of the present invention are sufficient to provide the methylphenidate in vivo PK profile depicted in FIG. 7. Suitable in vitro test methodology, techniques and apparatus to determine if a dosage form is properly characterized as having "a low in vitro solvent extractability value" are described below in Example 3. In summary, a test dosage form can be placed within a suitable amount of a liquid that my be readily obtained, for example water, alcohol (ethanol), soft drinks, vinegar, baking soda solutions, and the like. After a suitable time (and, for example, with suitable agitation or application of heat), the liquid "extraction solvent" can be tested for the presence of extracted methylphenidate. Any number of such liquids can be assembled into a "panel" of extraction solvents for the purposes of such testing. Accordingly, in these preferred embodiments, the abuse-resistant dosage form is resistant to extraction across a panel of common household solvents.

The controlled release carrier systems that are employed in the abuse-resistant oral pharmaceutical dosage forms disclosed and claimed herein are formed by the combination of a High Viscosity Liquid Carrier Material ("HVLCM"), a network former, and a rheology modifier. An HVLCM is a non-polymeric, non-water soluble liquid material having a viscosity of at least 5,000 cP at 37° C. that will not crystallize neat under ambient or physiological conditions. The term "non-water soluble" refers to a material that is soluble in water to a degree of less than one percent by weight under ambient conditions. The term "non-polymeric" refers to esters or mixed esters having essentially no repeating units in the acid moiety of the ester, as well as esters or mixed esters having acid moieties wherein functional units in the acid moiety are repeated a small number of times (i.e., oligomers). Generally, materials having more than five identical and adjacent repeating units or mers in the acid moiety of the ester are excluded by the term "non-polymeric" as used herein, but materials containing dimers, trimers, tetramers, or pentamers are included within the scope of this term. When the ester is formed from hydroxy-containing carboxylic acid moieties that can further esterify, such as lactic acid or glycolic acid, the number of repeat units is calculated based upon the number of lactide or glycolide moieties, rather than upon the number of lactic acid or glycolic acid moieties, where a lactide repeat unit contains two lactic acid moieties esterified by their respective hydroxy and carboxy moieties, and where a glycolide repeat unit contains two glycolic acid moieties esterified by their respective hydroxy and carboxy moieties. Esters having 1 to about 20 etherified polyols in the alcohol moiety thereof, or 1 to about 10 glycerol moieties in the alcohol moiety thereof, are considered non-polymeric as that term is used herein. HVLCMs may be carbohydrate-based, and may include one or more cyclic carbohydrates chemically combined with one or more carboxylic acids. HVLCMs also include non-polymeric eaters or mixed esters of one or more carboxylic acids, having a viscosity of at least 5,000 cP at 37° C., that do not crystallize neat under ambient or physiological conditions, wherein when the ester contains an alcohol moiety (e.g., glycerol). The ester may, for example comprise from about 2 to about 20 hydroxy acid moieties. Various HVLCMs used with the present controlled release carrier systems are described in U.S. Pat. Nos. 5,747,058; 5,968,542; and 6,413, 536. The present invention may employ any HVLCM described in these patents but is not limited to any specifically described materials. The HVLCM is typically present in a dosage form according to the invention in an amount of from 30 to 60%, for example from 35 to 45%, by weight.

Figure 13:
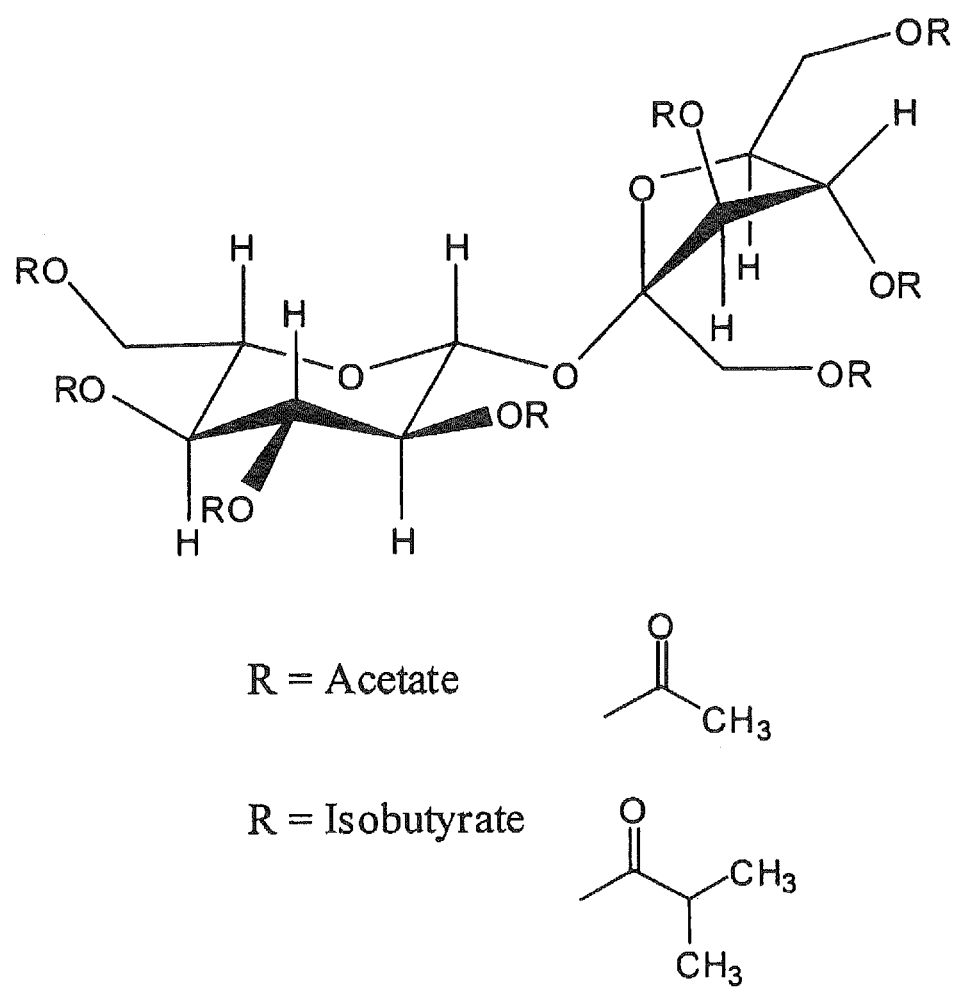
FIG. 13 depicts the chemical structure of sucrose acetate isobutyrate (SAIB).

In certain preferred embodiments of the invention, the controlled release carrier system comprises Sucrose Acetate Isobutyrate ("SAIB") as the HVLCM. SAIB is a non-polymeric highly viscous liquid at temperatures ranging from −80° C. to over 100° C., it is a fully esterified sucrose derivative. The chemical structure of SAIB is depicted herein as FIG. 13. The SAIB material is available from a variety of commercial sources including Eastman Chemical Company, where it is available as a mixed ester that does not crystallize but exists as a very highly viscous liquid. It is a hydrophobic, non-crystalline, low molecular weight molecule that is water insoluble and has a viscosity that varies with temperature. For example, pure SAIB exhibits a viscosity of approximately 2,000,000 centipoise (cP) at ambient temperature (RT) and approximately 600 cP at 80° C. The SAIB material has unique solution-viscosity relationship in that a SAIB solution established in a number of organic solvents has a significantly lower viscosity value than the pure SAIB material, and therefore the SAIB-organic solvent solutions render themselves capable of processing using conventional equipment such as mixers, liquid pumps and capsule production machines. SAIB also has applications in drug formulation and delivery, for example as described in U.S. Pat. Nos. 5,747,058; 5,968,542; 6,413,536; and 6,498,153. In the present invention, SAIB may be used as the HVLCM and may be present in quantities that vary significantly. For example, quantities of at least about 30, 35, 40, 50, 60, or from 61 to 99.9 percent by weight of the HVLCM, which can include one or more suitable HVLCM, relative to the total weight of the formulation (wt %) used to make the dosage form can be used. Typically, SAIB is present in a dosage form according to the invention in an amount of from 30 to 60% by weight, for example from 35 to 45% by weight.

In certain circumstances, it may be beneficial to provide a SAIB carrier material having a lower peroxide level to avoid peroxide-based degradation of various components of the controlled release carrier system and/or active agent. See, e.g., U.S. Patent Publication Number US 2007/0027105, "Peroxide Removal From Drug Delivery Vehicle". Various specific pharmaceutical formulations containing SAIB at about 40 wt % that are used to produce suitable dosage forms are discussed in the examples.

A "rheology modifier", as used herein, refers to a substance that possesses both a hydrophobic and a hydrophilic moiety. Rheology modifiers used in the practice of the invention generally have a logarithm of octanol-water partition coefficient ("Log P") of between about −7 and +15, preferably between −5 and +10, more preferable between −1 and +7. In addition, the rheology modifier will typically have a molecular weight of around 1,000 daltons or less. Rheology refers to the property of deformation and/or flow of a liquid material, and rheology modifiers are used to modify (lower) viscosity and (increase) flowability of the HVLCM and other constituents used in the controlled release carrier system, that is, to plasticize the HVLCM and other constituents. The rheology modifier may thus be a plasticizer, typically a plasticizer for the HVLCM. Rheology modifiers that are useful herein include, for example, caprylic/capric triglyceride (Migliol 810), isopropyl myristate ("IPM"), ethyl oleate, triethyl citrate, dimethyl phthalate, labrafil, labrasol, Gelucires, and benzyl benzoate. In certain preferred embodiments of the invention, the rheology modifier is IPM. The IPM material is a pharmaceutically acceptable hydrophobic solvent. The rheology modifier, which can include one or more suitable rheology modifier material, can be present in the formulations at from about 0.1 to about 20 percent by weight relative to the total weight of the formulation (wt %) used to produce the dosage forms of the present invention, preferably at from about 1 to about 18 wt %, and more preferably at from about 2 to about 15 wt %.

A "network former" refers to a material or compound that forms a network structure when introduced into a liquid medium (such as a HVLCM or a controlled release carrier system comprising an HVLCM). Network formers may be added to the liquid formulation such that, upon exposure to an aqueous environment, they form a three dimensional network within the formulation. While not wishing to be bound by any particular theory, it is believed that the network former allows the formation of a micro-network within the formulation upon exposure to an aqueous environment. This micro-network formation appears to be due, at least in part, to a phase inversion (e.g., a change in glass transition temperature, $T_g$) of the network former. The result is believed to be a skin or surface layer of precipitated network former at the interface between the dosage form and the aqueous environment of the GI tract, as well as the formation of a three-dimensional micro-network of precipitated network former within the dosage form. The network forwer is selected so as to have good solubility in the selected solvent used in the formulations, for example a solubility of between about 0.1 and 20 wt %. Additionally, good network formers will typically have a Log P between about −1 to 7. Suitable network formers include, for example, cellulose acetate butyrate ("CAB"), carbohydrate polymers, organic acids of carbohydrate polymers and other polymers, hydrogels, cellulose acetate phthalate, ethyl cellulose, Pluronic, Eudragit, Carbomer, hydroxyl propyl methyl cellulose, other cellulose acetates such as cellulose triacetate, PMMA, as well as any other material capable of associating, aligning or congealing to form three-dimensional networks in an aqueous environment. A particularly preferred network former for use in the practice of the invention is cellulose acetate butyrate grade 381-20 BP ("CAB 381-20" available from Eastman Chemicals). CAB 381-20 is a non-biodegradable polymer material that has the following chemical and physical characteristics: butyryl content of 36%, acetyl content of 15.5%, hydroxy content of 0.8%, a melting point of 185-196° C., glass transition temperature of 128° C., and a molecular weight number average of 66,000 to 83,000. Preferably, if a CAB material is used in the present formulations, it should be subjected to an ethanol washing step (and subsequent drying step) prior to addition to the formulation in order to remove potential contaminants therefrom. The network former, which can include one or more suitable network former materials, can be present in the formulations at from about 0.1 to about 20 percent by weight relative to the total weight of the formulation (wt %), preferably at from about 1 to about 18 wt %, more preferably at from about 2 to about 10 wt %, and even more preferably at from about 4 to about 6 wt %.

In addition to the combination of the HVLCM, network former and rheology modifier materials discussed above, the controlled release carrier systems that are employed in the abuse-resistant oral methylphenidate dosage forms disclosed and claimed herein can further include a number additional excipient materials including solvents, viscosity enhancing agents, hydrophilic agents, surfactants, and stabilizing agents.

The term "solvent", as used herein, refers to any substance that dissolves another substance (solute). Solvents may be used in the controlled release carrier systems of the present invention to dissolve one or more of the following constituents: HVCLMs; active agents; network formers; rheology modifiers; viscosity enhancing agents; hydrophilic agents; surfactants; and stabilizing agents. Preferably, the solvent can dissolve both the HVLCM and the network former. In addition, materials that can serve as rheology modifiers in certain controlled release carrier systems can also serve the function as a solvent to one or more constituent (e.g., the HVLCM, or the methylphenidate), or serve solely as a solvent in other carrier systems. One example of such a solvent is IPM, which is a hydrophobic solvent. In one embodiment of the invention, therefore, a dosage form may comprise both a hydrophilic solvent and a hydrophobic solvent Organic solvents suitable for use with the present invention include, but are not limited to: substituted heterocyclic compounds such as N-methyl-2-pyrrolidone (NMP) and 2-pyrrolidone (2-pyrol); triacetin; esters of carbonic acid and alkyl alcohols such as propylene carbonate, ethylene carbonate and dimethyl carbonate; fatty acids such as acetic acid, lactic acid and heptanoic acid; alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate (IPM), dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; ether alcohols such as 2-ethoxyethanol, ethylene glycol dimethyl ether, glycofurol and glycerol formal; alcohols such as benzyl alcohol, ethanol and propanol; polyhydroxy alcohols such as propylene glycol, polyethylene glycol (PEG), glycerin (glycerol), 1,3-butyleneglycol, and isopropylidene glycol (2,2-dimethyl-1,3-dioxolone-4-methanol); Solketal; dialkylamides such as dimethylformamide, dimethylacetamide; dimethylsulfoxide (DMSO) and dimethylsulfone; tetrahydrofuran; lactones such as ε-caprolactone and butyrolactone; cyclic alkyl amides such as caprolactam; aromatic amides such as N,N-dimethyl-m-toluamide, and 1-dodecylazacycloheptan-2-one; and the like; and mixtures and combinations thereof. Preferred solvents include triacetin, N-methyl-2-pyrrolidone, 2-pyrrolidone, dimethylsulfoxide, ethyl lactate, propylene carbonate, and glycofurol. In one particular preferred embodiment, the solvent is triacetin which is a hydrophilic solvent. The hydrophilic triacetin solvent can preferably be combined with the IPM rheology modifier which is a hydrophobic solvent to provide a solvent hydrophobic/hydrophilic solvent system within the controlled release carrier system. The solvent, which can include one or more suitable solvent materials, can be present in the formulations at from about 0.1 to about 40 percent by weight relative to the total weight of the formulation (wt %), preferably at from about 1 to about 35 wt %, more preferably at from about 10 to about 30 wt %, and even more preferably at from about 15 to about 28 wt %.

A "viscosity enhancing agent" or "second viscosity enhancing agent" is a material that can be added to the controlled release carrier system in order to increase the viscosity of the resulting carrier system. Viscosity enhancing agents can be selected to have good hydrogen bonding capability, such as a bonding capability greater than or equal to one per molecule. In certain cases, the viscosity enhancing agent has very low to no significant solubility in the formulation. If the agent is soluble, then preferably the solubility is less than 50 wt %. For inorganic or mineral viscosity enhancing agents, it is preferable if the material has a specific surface area greater than or equal to about 100 m2/g. For those skilled in the use of pharmaceutical systems using an HVLCM, particularly SAIB, it is generally known that as the viscosity of the controlled release system increases, e.g., as a solvent for the HVLCM leaves the system or by addition of a polymer material, release of the active agent from that carrier system will typically slow down since the HVLCM carrier matrix material has become more resistant to diffusion of the agent from the matrix material. Accordingly, it may be counter-intuitive for the skilled person to purposefully enhance (increase) the overall viscosity of the present controlled release carrier systems when it is desired to enhance the in vivo pharmacological performance of such systems to, for example, extend and/or increase the release performance to increase bioavailability of an active agent. However, it has been found that in certain dosage forms of the present invention, the addition of a viscosity enhancing agent can be used to provide dosage forms having enhanced in vive pharmacological performance as well as enhanced safety features and/or abuse-resistance properties as required herein. Suitable viscosity enhancing agents include biodegradable and non-biodegradable polymer materials. Non-limiting examples of suitable biodegradable polymers and oligomers include: poly(lactide), poly(lactide-co-glycolide), poly(glycolide), poly (caprolactone), polyamides, polyanhydrides, polyamino acids, polyorthoesters, polycyanoacrylates, poly(phosphazines), poly(phosphoesters), polyesteramides, polydioxanones, polyacetals, polyketals, polycarbonates, polyorthocarbonates, degradable polyurethanes, polyhydroxybutyrates, polyhydroxyvalerates, polyalkylene oxalates, polyalkylene succinates, poly(malic acid), chitin, chitosan, and copolymers, terpolymers, oxidized cellulose, hydroxyethyl cellulose, or combinations or mixtures of the above materials. Suitable non-biodegradable polymers include: polyacrylates, ethylene-vinyl acetate polymers, cellulose and cellulose derivatives, acyl substituted cellulose acetates and derivatives thereof including cellulose acetate butyrate (CAB), which is also used herein as a network former, non-erodible polyurethanes, polystyrenes, polyvinyl chloride, polyvinyl fluoride, polyvinyl (imidazole), chlorosulphonated polyolefins, polyethylene oxide, and polyethylene. Other suitable viscosity enhancing materials include stiffening agents such as clay compounds, including, talc, bentonite and kaolin, and metal oxides including silicon dioxide, zinc oxide, magnesium oxide, titanium oxide, and calcium oxide. In one preferred embodiment of the invention, a colloidal silicon dioxide (Cab-O-Sil) is used as a viscosity enhancing agent in a controlled release carrier system that further contains CAB as a network former. The colloidal silicon dioxide may further be characterized as a thixtropic agent since it is thought to enhance viscosity at resting conditions, which may be useful for product stability purposes, while also serving as viscosity thinning agent under conditions of mechanical stress which may be useful for controlled release performance. The viscosity enhancing agent, which can include one or more suitable viscosity enhancing material, can be present in the formulations at from about 0.01 to about 10 percent by weight relative to the total weight of the formulation (wt %) used to produce the dosage forms of the present invention, preferably at from about 0.1 to about 6 wt %, and more preferably at from about 1 to about 2 wt %.

Materials that can be used as "hydrophilic agents" in the practice of the invention include those that have natural affinity for aqueous systems. A material may be regarded as a hydrophilic agent for the purposes of this invention if the material displays a water sorption between about 10 to 100% (w/w). Hydrophilic agents will have a low Log P value. As discussed herein above, there are a number of constituents used to produce the controlled release carrier systems of the present invention that can be classed as a hydrophilic material (e.g., a hydrophilic solvent), or at least a material having a hydrophilic portion (e.g., a rheology modifier). Since the HVLCM material used in the present carrier systems is hydrophobic, it may be useful to include other materials in the carrier system that are hydrophilic in order to provide a carrier system that is balanced to have both hydrophobic and hydrophilic characteristics. For example, it is believed that the inclusion of one or more hydrophilic agent in the controlled release carrier systems of the present invention may participate in the control of methylphenidate diffusion from the carrier system. Accordingly, suitable hydrophilic agents include, but are not limited to, sugars such as sorbitol, lactose, mannitol, fructose, sucrose and dextrose, salts such as sodium chloride and sodium carbonate, starches, hyaluronic acid, glycine, fibrin, collagen, polymers such as hydroxylpropylcellulose ("HPC"), carboxymethylcellulose, hydroxyethyl cellulose ("HEC"); polyethylene glycol and polyvinylpyrrolidone, and the like. In a particularly preferred embodiment, a controlled release carrier system is provided that includes HEC as a hydrophilic agent. The hydrophilic agent, which can include one or more suitable hydrophilic agent material, can be present in the formulations at from about 0.1 to about 10 percent by weight relative to the total weight of the formulation (wt %) used to produce the dosage forms of the present invention, preferably at from about 1 to about 8 wt %, and more preferably at from about 3 to about 6 wt %. The hydrophilic agent may alternatively constitute the "first viscosity enhancing agent" of an embodiment of the invention.

Materials that can be used as "surfactants" in the practice of the invention include neutral and/or anionic/cationic excipients. Accordingly, suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics); polyoxyethylenesorbitans, e.g., TWEEN® surfactants (Atlas Chemical Industries); polysorbates; polyoxyethylene ethers, e.g. Brij; pharmaceutically acceptable fatty acid esters, e.g., lauryl sulfate and salts thereof, ampiphilic surfactants (glycerides, etc.); Gelucires (saturated polyglycolized glyceride (e.g., Gattefosse brand); and like materials. Surfactants, which can include one or more suitable surfactant material, can be present in the formulations at from about 0.01 to about 5 percent by weight relative to the total weight of the formulation (wt %) used to produce the dosage forms of the present invention, preferably at from about 0.1 to about 5 wt %, and more preferably at from about 0.1 to about 3 wt %.

Materials that can be used as stabilizing agents in the practice of the invention include any material or substance that can inhibit or reduce degradation (e.g., by chemical reactions) of other substances or substances in the controlled release carrier system with which the stabilizer is mixed. Exemplary stabilizers typically are antioxidants that prevent oxidative damage and degradation, e.g., sodium citrate, ascorbyl plamitate, vitamin A, and propyl gallate and/or reducing agents. Other examples include ascorbic acid, vitamin E, sodium bisulfite, butylhydroxyl toluene ("BHT"), BHA, acetylcysteine, monothioglycerol, phenyl-alpha-nathylamine, lecithin, and EDTA. These stabilizing materials, which can include one or more suitable such materials, can be present in the formulations at from about 0.001 to about 2 percent by weight relative to the total weight of the formulation (wt %) used to produce the dosage forms of the present invention, preferably at from about 0.01 to about 0.1 wt %, and more preferably at from about 0.01 to about 0.02 wt %.

An oral abuse-resistant methylphenidate dosage form comprising a controlled release carrier system which comprises a HVLCM, a network former, a rheology modifier, a hydrophilic agent and a solvent can thus contain: (a) from 1.3 to 35 wt % such as 5 to 10 wt % of the methylphenidate; (b) from 2 to 10 wt % such as 4 to 6 wt % of the network former; (c) from 0.1 to 20 wt % for example 2 to 15 wt % of the rheology modifier; (d) from 1 to 8 wt % for example 3 to 6 wt % of the hydrophilic agent; (e) from 10 to 40 wt % for example from 10 to 30 wt % of the solvent; and (f) from 30 to 60 wt % such as 35 to 45 wt % of the HVLCM. Typically, the HVLCM is sucrose acetate isobutyrate (SAIB); the network former is selected from cellulose acetate butyrate (CAB), cellulose acetate phthalate, ethyl cellulose, hydroxypropylmethyl cellulose and cellulose triacetate; the rheology modifier is selected from isopropyl myristate (IPM), caprylic/capric triglyceride, ethyl oleate, triethyl citrate, dimethyl phthalate and benzyl benzoate; the hydrophilic agent is selected from hydroxyethylcellulose (HEC), hydroxypropylcellulose, caboxymethylcellulose, polyethylene glycol and polyvinylpyrrolidone; and the solvent is selected from triacetin, N-methyl-2-pyrrolidone, 2-pyrrolidone, dimethylsulfoxide, ethyl lactate, propylene carbonate and glycofurol. Preferably, the HVLCM is SAIB, the network former is CAB, the rheology modifier is IPM, the hydrophilic agent is HEC, and the solvent is triacetin.

The controlled release carrier system can further comprise a viscosity enhancing agent such as silicon dioxide. The viscosity enhancing agent is typically present in an amount from 0.1 to 6 wt % such as 1 to 2 wt %.

In an alternative embodiment, an oral abuse-resistant methylphenidate dosage form comprising a controlled release carrier system which comprises a HVLCM, a network former, a first viscosity enhancing agent, a hydrophilic solvent and a hydrophobic solvent, can contain: (a) from 1.3 to 35 wt % such as 5 to 10 wt % of the methylphenidate; (b) from 2 to 10 wt % such as 4 to 6 wt % of the network former, (c) from 1 to 8 wt % for example 3 to 6 wt % of the first viscosity enhancing agent; (d) from 10 to 40 wt % for example 10 to 30 wt % of the hydrophilic solvent; (e) from 0.1 to 20 wt % for example from 2 to 15 wt % of the hydrophobic solvent; and (f) from 30 to 60 wt % such as 35 to 45 wt % of the HVLCM. Typically in this embodiment the HVLCM is SAIB; the network former is selected from CAB, cellulose acetate phthalate, ethyl cellulose, hydroxypropylmethyl cellulose and cellulose triacetate; the first viscosity enhancing agent is HEC, hydroxypropylcellulose, carboxymethylcellulose, polyethylene glycol and polyvinylpyrrolidone; the hydrophilic solvent is selected from triacetin, N-methyl-2-pyrrolidone, 2-pyrrolidone, dimethylsulfoxide, ethyl lactate, propylene carbonate and glycofurol; and the hydrophobic solvent is IPM. Preferably, the HVLCM is SAIB, the network former is CAB, the first viscosity enhancing agent is HEC, the hydrophilic solvent is triacetin, and the hydrophobic solvent is IPM.

The controlled release system can further comprise a second viscosity enhancing agent such as silicone dioxide. The second viscosity enhancing agent is typically present in an amount from 0.1 to 6 wt % such as 1 to 2 wt %.

Once all of the constituents have been selected to produce a controlled release carrier system in accordance with the present invention, a liquid pharmaceutical formulation can be prepared by simply mixing, for example a HVLCM, a rheology modifier, a network former, the methylphenidate, a solvent and any additional additives. The formulations of the present invention are produced as liquid mixtures, and have a number of excipient ingredients that are in solution, suspension, or in partial solution within the final formulation. Suitable methods for compounding or manufacturing the formulations make use of typical pharmaceutical/chemical mixing and handling apparatus and techniques. Since the liquid formulations of the invention are formed from a mixture number of highly viscous liquids and solids, they will tend to have exceptionally high final viscosities. Accordingly, the specific equipment and techniques employed in the manufacture of such formulations are preferably selected so as to accommodate such material demands. In particular, various excipients, such as network formers, are typically added to the formulation mixture in the solid or semi-solid state, and as such they may be screened or otherwise size-reduced prior to addition to a formulation mixing apparatus. Other solid excipients may require melting prior to addition to the liquid mixture. The HVLCM materials are very high viscosity liquid materials, however they tend to exhibit a dramatic reduction in viscosity with increases in heat, and as such the mixing apparatus may be heated to accommodate the addition of the HVLCM material or other similar materials. However, the mixing and processing conditions must take into account the final integrity of the formulation, and as such the mixing conditions are preferably selected so as to have a low-sheer effect on the formulation, and to avoid any extended or pronounced excursions into high or low heat conditions. Once the formulation has been properly combined, an appropriate amount of the resulting liquid mixture can be placed into a suitable capsule, such as a gelatin capsule or the like to provide an oral methylphenidate dosage form. Alternative liquid formulations may include emulsifying the mixture in water, and introducing this emulsion into a capsule.

With regard to a formulation that is formed from the mixture of methylphenidate, a HVLCM, a network former, a rheology modifier, a hydrophilic agent and a solvent, one suitable manufacturing or compounding process would include the steps of: preheating the HVLCM; mixing the solvent with the preheated HVLCM to form a uniform solution of the HVLCM in the solvent; adding and mixing the rheology modifier optionally, adding and mixing a viscosity enhancing agent; homogenizing the formulation, adding and mixing the methylphenidate; and then adding and mixing the hydrophilic agent. Furthermore, the process can include the step of filling capsules with the formulation obtained in the process and, optionally, packaging the filled capsules into unit dose blisters or multidose plastic bottles.

With regard to a formulation that is formed from the mixture of methylphenidate, a HVLCM, a network former, a first viscosity enhancing agent, a hydrophilic solvent and a hydrophobic solvent, a suitable manufacturing or compounding process may include the steps of: preheating the HVLCM; mixing the hydrophilic solvent with the preheated HVLCM to form a uniform solution of the HVLCM in the solvent; adding the hydrophobic solvent; optionally, adding and mixing a viscosity enhancing agent; homogenizing the formulation, adding and mixing the methylphenidate; and then optionally adding and mixing a hydrophilic agent. Furthermore, the process can include the step of filling capsules with the formulation obtained in the process and, optionally, packaging the filled capsules into unit dose blisters or multidose plastic bottles.

A suitable GMP manufacturing method for producing the abuse-resistant dosage forms and formulations of the present invention is described in Example 1 below.

In certain preferred embodiments, the oral dosage form is composed of a liquid formulation containing the methylphenidate and the controlled release carrier system encapsulated within an enclosure or capsule, preferably biodegradable, such as a capsule or a gelatin capsule ("gelcap"), wherein the capsule is made of a substance that degrades or otherwise dissociates when exposed to conditions present in the gastro-intestinal tract of a mammal. Capsules and gelcaps are well known in drug delivery technology and one of ordinary skill could select such a capsule as appropriate for delivery of a particular active agent. Once the capsule has dissolved or dissociated from the formulation, the formulation of the invention generally remains intact, especially for hydrophobic formulations, and passes through the GI tract without emulsification or fragmentation.

In certain more specific embodiments the invention encompasses an oral dosage form comprising a liquid formulation contained within a biodegradable capsule, wherein the formulation comprises methylphenidate and a HVLCM, and wherein the capsule is made of a substance that degrades when exposed to conditions present in the gastro-intestinal tract of a mammal. In certain embodiments the capsule comprises gelatin or synthetic polymers such as hydroxyl ethyl cellulose and hydroxyl propylmethyl cellulose. Gelcaps can be of the hard or soft variety, including, for example, polysaccharide or hypromellose acetate succinate based caps (e.g., Vegicaps brand, available from Catalent). The capsule can also be coated with an enteric coating material such as AQIAT (Shin-Etsu) to delay release. Gelatin capsules are well suited for delivering liquid formulations such as vitamin E and cod-liver oil. Gelatin capsules are stable in storage, but once in the acid environment of the stomach (low pH less than about pH 4-5), the gelcap dissolves over a 1-15 minute period.

In accordance with the present invention, the abuse-resistant oral methylphenidate dosage forms may be formulated so as to produce targeted plasma levels of methylphenidate over a particular period. This is obviously of great importance in maintaining a methylphenidate plasma level within an appropriate therapeutic range to provide: (i) an initial increasing in vivo rate of release of methylphenidate from the controlled release system suitable to provide an initial increasing-rate phase of less than or equal to about 2 hours, and sufficient to provide a therapeutically effective amount of methylphenidate for a rapid onset of action; (ii) a second, zero-order or decreasing (i.e., non-ascending) in vivo rate of release of methylphenidate from the controlled release system that provides a subsequent zero order- or decreasing-rate phase sufficient to provide a therapeutically effective amount of methylphenidate through at least about 11 to 12 hours post administration; and (iii) a single $T_{max}$ of about 5.5 to 7.5 hours post administration. The novel and unique in vivo methylphenidate release kinetics provided by the abuse-resistant oral dosage forms of the present invention are sufficient to provide the methylphenidate in vivo PK profile depicted in FIG. 7. The exact time to maximum plasma concentration may be adjusted by adjusting various components of the controlled release carrier system as taught herein.

Once per day (QD) is typically used to maintain a sufficient clinical effect, e.g., to treat ADD or ADHD. Other dosage regimens may be determined by a physician in accordance with standard practices.

EXAMPLES

Please note that the examples described herein are illustrative only and in no way limit the scope of the invention.

Example 1: Preparation of Formulations (GMP Manufacturing Process)

A GMP manufacturing process for the dosage forms of the present invention was developed and carried out as follows. The following raw materials were used to create the formulations: methylphenidate ("MPH"); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Gelucire 50/13

(Gattefosse) ("GEL"); and Miglyol 812 ("MIG"). The formulations were filled into size #3 gelatin capsule shells. The specific details for the three different formulations produced using the GMP manufacturing processes of this Example 1 are disclosed below in Tables 1 and 2. The batch sizes were up to 500 g.

TABLE 1

Formulation by Weight Percent (wt %)

| Component | MPH1 40 mg | MPH2 48 mg | MPH3 48 mg | MPH11 48 mg | MPH12 48 mg | MPH13 48 mg |
|---|---|---|---|---|---|---|
| MPH | 20.00 | 20.00 | 20.00 | 20.00 | 20.00 | 20.00 |
| SAIB | 33.35 | 34.31 | 34.55 | 34.31 | 29.25 | 34.55 |
| TA | 22.23 | 22.87 | 23.03 | 22.87 | 20.89 | 23.03 |
| CAB | 4.80 | 5.20 | 6.40 | 5.21 | 5.58 | 6.42 |
| IPM | 13.60 | 12.80 | 12.80 | 12.80 | — | 12.80 |
| MIG | — | — | — | — | 16.0 | — |
| HEC | 0.00 | 2.40 | 0.00 | 2.40 | 4.80 | — |
| SiO$_2$ | 2.00 | 1.60 | 1.60 | 1.60 | 1.60 | 1.60 |
| BHT | 0.02 | 0.02 | 0.02 | 0.02 | 0.02 | 0.02 |
| GEL | 4.00 | 0.80 | 1.60 | 0.80 | 1.84 | 1.60 |

TABLE 2

Formulation by Mass (mg)

| Component | MPH1 40 mg | MPH2 48 mg | MPH3 48 mg | MPH11 48 mg | MPH12 48 mg | MPH13 48 mg |
|---|---|---|---|---|---|---|
| MPH | 40.00 | 48.00 | 48.00 | 48.00 | 48.00 | 48.00 |
| SAIB | 66.70 | 82.34 | 82.92 | 82.30 | 70.20 | 82.90 |
| TA | 44.46 | 54.89 | 55.27 | 54.90 | 50.10 | 55.30 |
| CAB | 9.60 | 12.48 | 15.36 | 12.50 | 13.40 | 15.40 |
| IPM | 27.20 | 30.72 | 30.72 | 30.70 | — | 30.70 |
| MIG | — | — | — | — | 38.40 | — |
| HEC | 0.00 | 5.76 | 0.00 | 5.80 | 11.50 | — |
| SiO$_2$ | 4.00 | 3.84 | 3.84 | 3.80 | 3.80 | 3.80 |
| BHT | 0.04 | 0.05 | 0.05 | 0.05 | 0.05 | 0.05 |
| GEL | 8.00 | 1.92 | 3.84 | 1.90 | 4.40 | 3.80 |
| Total | 200.00 | 240.00 | 240.00 | 240.00 | 240.00 | 240.00 |

Figure 14:
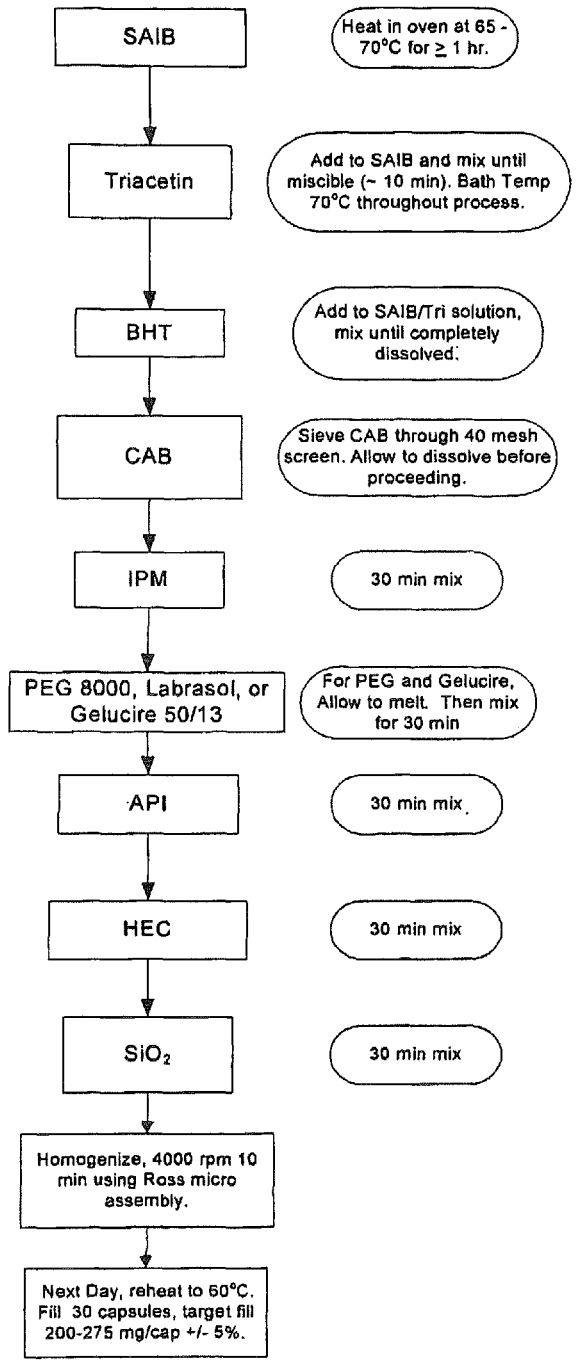
FIG. 14 depicts a flow chart for a GMP manufacturing process described in Example 1.

The primary mixing apparatus used in the GMP manufacturing process was a Ross Model No. HSM 100 LCI, equipped with propeller type impeller (4 blade) with a diameter of 2.25 inches. The mixing container that was used was a 2 liter Glass Jar with an internal Diameter (mixing area) of 4.181 inches. Temperature control was carried out using a VWR immersion circulator and a VWR gravity convection oven model 1320. A micro mixer homogenizing assembly for the Ross mixer was used for the final homogenization step. After the final mixing step, bulk formulations were allowed to cool to room temperature for a minimum of 16 hours (overnight) prior to filling into capsules. The flow chart for the instant GMP manufacturing process is depicted in FIG. 14.

Example 2: Analysis of Formulations (In Vitro Dissolution Testing Procedures)
Two in vitro dissolution test methods were developed in order to assess the controlled release performance of abuse-resistant dosage forms produced according to the present invention such as the methylphenidate dosage forms recited herein. The first dissolution method (Method 1) was based upon USP <711> Method A for delayed-release dosage forms and uses an USP dissolution apparatus Type 2 (without basket) with a two-stage media (an initial volume of 750 mL of 0.1N HCl acid as the dissolution medium, followed by adjustment to pH 6.8 by addition of 250 mL of sodium phosphate buffer after 2 hours). The two-stage media was selected to simulate the pH range over which a dosage form will release active agent during transit through the GI tract. Stainless steel coiled wire type 316 is used as a sinker to ensure that the dosage forms remain at the bottom of the dissolution vessel during release rate testing.

Figure 15:
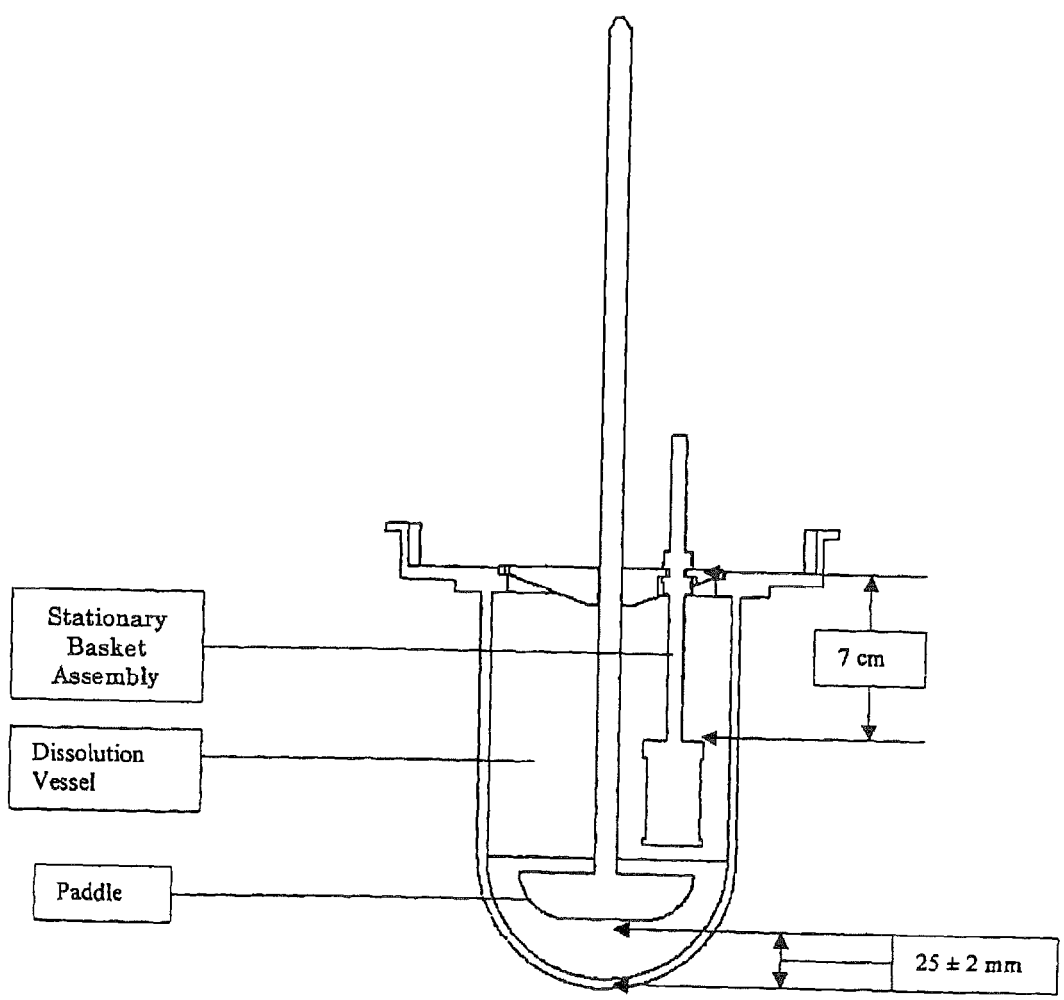
FIG. 15 is a pictorial representation of the modified dissolution vessel and paddle described in Example 2.

The second dissolution method (Method 2) was optimized to assess the controlled release performance of the abuse-resistant dosage forms having 5, 10, 20, 30 and 40 mg of the active agent. In this regard, the unique controlled release characteristics of the abuse-resistant dosage forms used in the practice of the invention are such that standard dissolution methodology and apparatus may not bear a close relationship to the rate or extent of active agent release as observed in in vivo pharmacokinetic studies. This is due in large part to the use of very hydrophobic excipients in the inventive dosage forms (e.g., SAIB and IPM), resulting in compositions that result in a controlled release mass with low water permeability. Accordingly, this second method represents an enhancement of the earlier method (Method 1) to provide a better reflection of in vivo release. The new method uses the paddle configuration of an USP dissolution apparatus Type 2 with a stainless steel stationary basket assembly (type 316, 20-mesh basket with 20-mesh screen ceiling modification) attached to a modified conical low-loss evaporation cover on the dissolution vessel. These changes to the traditional apparatus were carried out in order to place the dosage form in the high shear flow zone of the USP dissolution apparatus, with an increased paddle speed to increase medium flow within the dissolution vessel. This new, fixed high-flow zone is located just above the rotating paddle. During testing, the dissolution media perfuses the stationary basket, facilitating release of the active agent from the full surface area of the dosage form and thus overcoming any surface boundary layer limitations that could result from placement of the dosage form at the bottom of the dissolution vessel. A pictorial representation of the modified dissolution vessel and paddle, with the stationary basket assembly is provided as FIG. 15. In addition to the stationary basket assembly, a screen ceiling inside the mesh basket was developed to prevent the dosage forms from floating within the basket.

Suitable stationary basket assemblies are commercially available and can be purchased from Varian as a kit. The kit contains a mesh basket (10, 20 or 40 mesh), which attaches to a basket shaft. A hole in the evaporation cover of the dissolution vessel allows the basket shaft to be secured to it. However, the evaporation covers provided with the kit are not ideal for use in an extended controlled release test. This is because the covers are flat and also contain a large cut out which allows them to be easily removed from the dissolution apparatus. Over the course of a 24-hour dissolution test, use of the covers provided with the kit would cause significant media loss due to evaporation. Evaporative media loss would ultimately lead to higher than expected release rate profiles. Previous dissolution studies with the dosage forms of the present invention have in fact given controlled release rate profiles well in excess of 100% release. An alternative to the kit evaporation cover was therefore developed.

The dissolution profiles using 20-Mesh Basket/20-Mesh Screen Ceiling and 40-Mesh Basket/without ceiling were determined to be the same. The 20-Mesh Baskets were chosen in order to maximize the hydrodynamic flow of dissolution media through the basket while minimizing leakage of the dosage form from the basket. The screen ceiling is used to confine the dosage form within the basket and improve assay variability.

In addition, Method 2 uses a single-phase dissolution medium (0.1N HCl with 0.5% (w/v) sodium dodecyl sulfate (SDS). The addition of the surfactant (SDS) to the dissolution medium improves the ability of the medium to wet the hydrophobic controlled release mass during testing.

Finally, a reverse phase HPLC method is used for determining the active agent concentration of the dosage form samples obtained from the dissolution testing methods of this Example 2. The mobile phase for the first dissolution method (Method 1) is prepared in two steps while the mobile phase for the second dissolution method (Method 2) is prepared in one step. A summary of the method parameters for Methods 1 and 2 is provided below as Table 3.

TABLE 3

| | Test Method | |
|---|---|---|
| | Method 1 | Method 2 |
| Media | 750 mL 0.1N HCl (2 hours) 250 mL 0.2N Na Phosphate | 0.1N HCl/0.5% SDS (1000 mL) |
| Paddle Speed | 50 RPM | 100 RPM |
| Bath Temperature | 37° C. | 37° C. |
| Sample Containment | Coiled Sinker (Type 316 stainless steel) | Stationary Basket Assembly (20 Mesh with Ceiling) |
| Sample Timepoints | 0.25, 0.5, 1, 2, 3, 6, 10, 12, 18 and 24 hours | 0.25, 0.5, 1, 2, 3, 6, 10, 12, 18 and 24 hours |
| Mobile Phase | 65% SDS Buffer/35% CAN SDS Buffer (0.5% SDS/1% Acetic Acid/20% CAN) | 0.35% SDS/0.7% Acetic Acid/44% ACN/56% Water |
| HPLC Column | Waters XTerra C18, 5 µm, 4.6 × 150 mm | Waters XTerra C18, 5 µm, 4.6 × 150 mm |
| Flow Rate | 1.0 mL/min | 1.0 mL/min |
| Run Time | 8 min | 8 min |
| UV Detection | 240 nm | 240 nm |
| Injection Volume | 20 µL | 20 µL |
| Column Temperature | 40° C. | 40° C. |

Example 2a

The following in vitro dissolution test was carried out to characterize the in vitro release of abuse-resistant methylphenidate oral dosage forms across several different formulations.

The abuse-resistant methylphenidate oral dosage forms used in this Example 2a were prepared using the following raw materials: methylphenidate ("MPH"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Gelucire 50/13 (Gattefosse) ("GEL"); and Miglyol 812 ("MIG"). The formulations were produced using the manufacturing process as described in Example 1 above, and then filled into size #3 gelatin capsule shells to produce the dosage forms that were used as Test Capsules. The details of the formulations and the dosage forms containing the formulations of this Example 2a are disclosed below in Tables 4 and 5.

TABLE 4

| | Formulation by Weight Percent (wt %) | | | | | |
|---|---|---|---|---|---|---|
| Component | MPH1 40 mg | MPH2 48 mg | MPH3 48 mg | MPH11 48 mg | MPH12 48 mg | MPH13 48 mg |
| MPH | 20.00 | 20.00 | 20.00 | 20.00 | 20.00 | 20.00 |
| SAIB | 33.35 | 34.31 | 34.55 | 34.31 | 29.25 | 34.55 |
| TA | 22.23 | 22.87 | 23.03 | 22.87 | 20.89 | 23.03 |
| CAB | 4.80 | 5.20 | 6.40 | 5.21 | 5.58 | 6.42 |
| IPM | 13.60 | 12.80 | 12.80 | 12.80 | — | 12.80 |
| MIG | — | — | — | — | 16.0 | — |
| HEC | 0.00 | 2.40 | — | 2.40 | 4.80 | — |
| SiO$_2$ | 2.00 | 1.60 | 1.60 | 1.60 | 1.60 | 1.60 |
| BHT | 0.02 | 0.02 | 0.02 | 0.02 | 0.02 | 0.02 |
| GEL | 4.00 | 0.80 | 1.60 | 0.80 | 1.84 | 1.60 |

TABLE 5

| | Formulation by Mass (mg) | | | | | |
|---|---|---|---|---|---|---|
| Component | MPH1 40 mg | MPH2 48 mg | MPH3 48 mg | MPH11 48 mg | MPH12 48 mg | MPH13 48 mg |
| MPH | 40.00 | 48.00 | 48.00 | 48.00 | 48.00 | 48.00 |
| SAIB | 66.70 | 82.34 | 82.92 | 82.30 | 70.20 | 82.90 |
| TA | 44.46 | 54.89 | 55.27 | 54.90 | 50.10 | 55.30 |
| CAB | 9.60 | 12.48 | 15.36 | 12.50 | 13.40 | 15.40 |
| IPM | 27.20 | 30.72 | 30.72 | 30.70 | — | 30.70 |
| MIG | — | — | — | — | 38.40 | — |
| HEC | 0.00 | 5.76 | 0.00 | 5.80 | 11.50 | — |
| SiO$_2$ | 4.00 | 3.84 | 3.84 | 3.80 | 3.80 | 3.80 |
| BHT | 0.04 | 0.05 | 0.05 | 0.05 | 0.05 | 0.05 |
| GEL | 8.00 | 1.92 | 3.84 | 1.90 | 4.40 | 3.80 |
| Total | 200.00 | 240.00 | 240.00 | 240.00 | 240.00 | 240.00 |

Figure 16A:
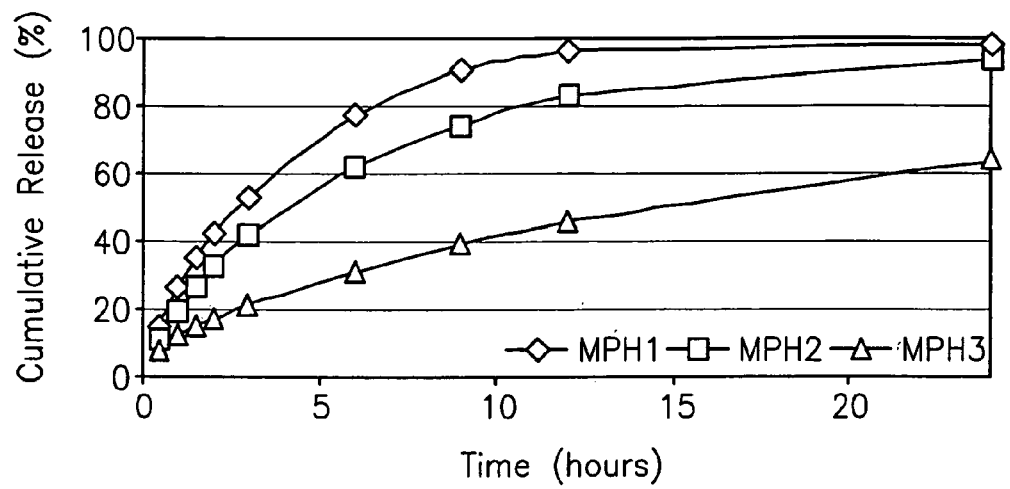
Figure 16B:
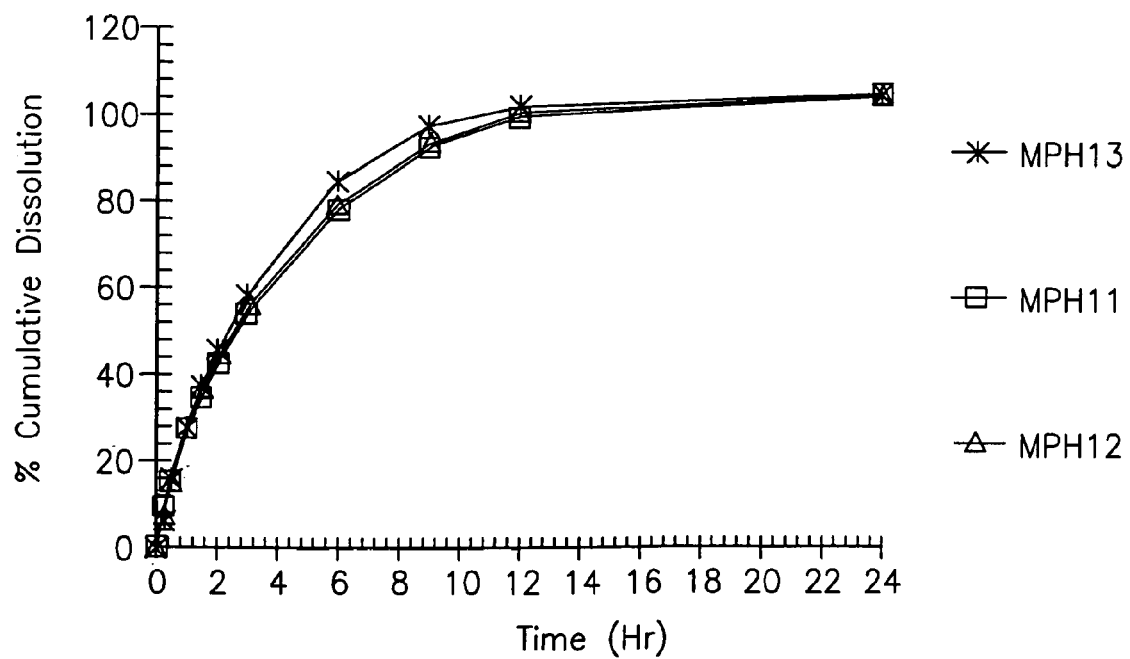

The dissolution study was carried out using the apparatus, reagents and methods of the Method 1 dissolution test described above, with the following exceptions: sample timepoints were at 0.5 hour, 1, 1.5, 2, 3, 6, 9, 12 and 24 hour. Dissolution results were obtained on the following Test Capsules: four (n=4) each of formulations MPH1 and MPH11-MPH12, and eight (n=8) each of formulations MPH2 and MPH3. The mean dissolution data from the six sets of Test Capsules are summarized below in Table 6, and depicted in FIGS. 16A and 16B.

TABLE 6

| Mean Cumulative Drug Released | | | | | | | | | |
|---|---|---|---|---|---|---|---|---|---|
| 0.5 hr | 1 hr | 1.5 hr | 2 hr | 3 hr | 6 hr | 9 hr | 12 hr | 24 hr | |
| Formulation # MPH1 | | | | | | | | | |
| 15.2% | 26.4% | 35.1% | 42.5% | 53.0% | 77.6% | 90.6% | 96.3% | 98.9% | Mean |
| 0.8 | 0.8 | 0.9 | 1.1 | 1.3 | 1.7 | 1.2 | 0.8 | 1.0 | SD |
| Formulation # MPH2 | | | | | | | | | |
| 11.1% | 19.27% | 26.4% | 32.5% | 42.0% | 62.1% | 74.5% | 83.1% | 94.5% | Mean |
| 1.3 | 2.0 | 2.8 | 3.5 | 4.8 | 6.2 | 5.9 | 5.7 | 7.0 | SD |

TABLE 6-continued

Mean Cumulative Drug Released

| 0.5 hr | 1 hr | 1.5 hr | 2 hr | 3 hr | 6 hr | 9 hr | 12 hr | 24 hr | |
|---|---|---|---|---|---|---|---|---|---|
| Formulation # MPH3 | | | | | | | | | |
| 7.9% | 12.0% | 15.1% | 17.6% | 21.6% | 31.3% | 39.1% | 45.7% | 64.7% | Mean |
| 1.3 | 2.0 | 2.5 | 3.0 | 3.6 | 5.2 | 6.5 | 7.9 | 11.4 | SD |
| Formulation # MPH11 | | | | | | | | | |
| 15.3% | 27.5% | 34.8% | 42.3% | 54.0% | 78.0% | 92.5% | 99.5% | 104.3% | Mean |
| 1.7 | 3.1 | 2.2 | 1.9 | 2.2 | 1.4 | 1.9 | 1.3 | 1.3 | SD |
| Formulation # MPH12 | | | | | | | | | |
| 15.8% | 28.0% | 36.9% | 44.3% | 55.8% | 79.3% | 93.2% | 100.7% | 104.4% | Mean |
| 1.0 | 1.3 | 1.3 | 1.2 | 1.2 | 1.4 | 1.8 | 2.3 | 2.8 | SD |
| Formulation # MPH13 | | | | | | | | | |
| 14.9% | 27.6% | 37.5% | 45.7% | 58.5% | 84.9% | 97.6% | 101.7% | 104.3% | Mean |
| 1.0 | 1.4 | 1.9 | 2.3 | 3.2 | 4.0 | 2.0 | 1.0 | 0.4 | SD |

Example 2b

The following in vitro dissolution tests were carried out in order to compare a target in vitro release profile of a methylphenidate oral dosage form produced according to the invention against several candidate abuse-resistant methylphenidate formulations produced according to the present invention.

The abuse-resistant methylphenidate oral dosage forms used in this Example 2b were prepared using the following raw materials: methylphenidate ("MPH"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Miglyol 812 ("MIG"); and Gelucire 50/13 (Gattefosse) ("GEL"). The formulations were produced using the manufacturing process as described in Example 1 above, and then filled into size #3 gelatin capsule shells to produce the dosage forms that were used as Test Capsules. The details of the formulations and the dosage forms containing the formulations of this Example 2b are disclosed below in Tables 7a and 7b.

TABLE 7a

Formulation by Weight Percent (wt %)

| | MPH1 40 mg | MPH4 36 mg | MPH5 40 mg | MPH6 48 mg | MPH7 48 mg | MPH8 48 mg | MPH9 29 mg | MPH10 40 mg | MPH11 48 mg | MPH12 48 mg | MPH13 48 mg |
|---|---|---|---|---|---|---|---|---|---|---|---|
| MPH | 20.00 | 13.04 | 20.00 | 20.00 | 15.00 | 15.00 | 10.25 | 20.00 | 20.00 | 20.00 | 20.00 |
| SAIB | 33.35 | 38.36 | 34.55 | 35.48 | 37.74 | 37.74 | 25.59 | 33.83 | 34.29 | 29.25 | 34.55 |
| TA | 22.23 | 25.57 | 23.03 | 23.66 | 25.16 | 25.16 | 46.43 | 22.55 | 22.87 | 20.89 | 23.03 |
| IPM | 13.60 | 13.92 | 12.80 | 12.54 | 13.33 | 13.35 | 9.68 | 12.80 | 12.80 | | 12.80 |
| CAB | 4.80 | 5.66 | 6.40 | 5.10 | 5.43 | 5.32 | 3.93 | 5.21 | 5.21 | 5.58 | 6.42 |
| SiO2 | 2.00 | 1.74 | 1.60 | 1.60 | 1.67 | 1.63 | 1.21 | 1.60 | 1.60 | 1.60 | 1.60 |
| GEL | 4.00 | 1.74 | 1.60 | 1.60 | 1.67 | 1.63 | 3.03 | 4.00 | 0.80 | 1.84 | 1.60 |
| MIG | | | | | | | | | | 16.0 | |
| HEC | | | | | | | | | 2.42 | 4.80 | |
| BHT | 0.02 | 0.02 | 0.02 | 0.02 | 0.02 | 0.02 | 0.01 | 0.02 | 0.02 | 0.02 | 0.02 |
| Total | 100.00 | 100.04 | 100.00 | 100.00 | 100.01 | 99.85 | 100.13 | 100.00 | 100.01 | 99.98 | 100.02 |

TABLE 7b

Formulation by Weight Mass (mg)

| | MPH1 40 mg | MPH4 36 mg | MPH5 40 mg | MPH6 48 mg | MPH7 48 mg | MPH8 48 mg | MPH9 29 mg | MPH10 40 mg | MPH11 48 mg | MPH12 48 mg | MPH13 48 mg |
|---|---|---|---|---|---|---|---|---|---|---|---|
| MPH | 40.00 | 35.86 | 40.00 | 48.00 | 48.00 | 48.00 | 28.70 | 40.00 | 48.00 | 48.00 | 48.00 |
| SAIB | 66.70 | 105.49 | 69.10 | 85.15 | 120.77 | 120.77 | 71.65 | 67.66 | 82.30 | 70.20 | 82.90 |
| TA | 44.46 | 70.32 | 46.06 | 56.79 | 80.51 | 80.51 | 130.00 | 45.10 | 54.90 | 50.10 | 55.30 |
| IPM | 27.20 | 38.28 | 25.60 | 30.11 | 42.65 | 42.70 | 27.10 | 25.60 | 30.70 | | 30.70 |
| CAB | 9.60 | 15.55 | 12.80 | 12.23 | 17.38 | 17.03 | 11.00 | 10.40 | 12.50 | 13.40 | 15.40 |
| SiO2 | 4.00 | 4.79 | 3.20 | 3.84 | 5.33 | 5.22 | 3.39 | 3.20 | 3.80 | 3.80 | 3.80 |

TABLE 7b-continued

| | Formulation byWeight Mass (mg) | | | | | | | | | | |
|---|---|---|---|---|---|---|---|---|---|---|---|
| | MPH1 40 mg | MPH4 36 mg | MPH5 40 mg | MPH6 48 mg | MPH7 48 mg | MPH8 48 mg | MPH9 29 mg | MPH10 40 mg | MPH11 48 mg | MPH12 48 mg | MPH13 48 mg |
| GEL | 8.00 | 4.79 | 3.20 | 3.84 | 5.33 | 5.22 | 8.48 | 8.00 | 1.90 | 4.40 | 3.80 |
| MIG | | | | | | | | | | 38.40 | |
| HEC | | | | | | | | | 5.80 | 11.50 | |
| BHT | 0.03 | 0.05 | 0.03 | 0.04 | 0.05 | 0.05 | 0.03 | 0.03 | 0.05 | 0.05 | 0.05 |
| Total | 200.00 | 275.11 | 200.00 | 240.00 | 320.03 | 319.52 | 280.36 | 200.00 | 239.95 | 239.85 | 239.95 |

Initially, the dissolution testing methods and apparatus described above in Example 2a were used to determine in vitro dissolution release performance for comparator tablets (Concerta and Metadate CD). The cumulative release results thus obtained were compared against the cumulative release data presented in the U.S. Pat. No. 6,919,373 (the Concerta patent), and then plotted against input in vivo obtained via deconvolution (open symbols) for both Metadate CD and Concerta. FIGS. 10A and 10B depict the results of this initial study, where FIG. 10A depicts the cumulative release profiles of the Concerta and Metadate CD comparators and compares them with cumulative release data presented in the U.S. Pat. No. 6,919,373; and FIG. 10B depicts the cumulative release in vitro results plotted against input in vivo obtained via deconvolution (open symbols) for both Metadate CD and Concerta.

Next, cumulative release data for 11 Test Capsules (MPH1 and MPH4-MPH13) were obtained. These results are reported below in Table 8.

TABLE 8

| Mean Cumulative Drug Released | | | | | | | | | |
|---|---|---|---|---|---|---|---|---|---|
| 0.5 hr | 1 hr | 1.5 hr | 2 hr | 3 hr | 6 hr | 9 hr | 12 hr | 24 hr | |
| Formulation # MPH4 | | | | | | | | | |
| 15.4 | 29.0 | 39.6 | 48.3 | 61.0 | 85.8 | 95.7 | 98.8 | 99.5 | Mean |
| 2.3 | 3.5 | 4.1 | 4.3 | 4.5 | 2.5 | 0.8 | 2.3 | 3.4 | Std Dev |
| Formulation # MPH9 | | | | | | | | | |
| 21.2 | 26.7 | 31.0 | 34.8 | 41.3 | 58.8 | 70.5 | 77.8 | 85.8 | Mean |
| 1.6 | 1.8 | 2.1 | 2.4 | 2.7 | 3.0 | 2.8 | 2.5 | 1.9 | Std Dev |
| Formulation # MPH10 | | | | | | | | | |
| 18.2 | 29.1 | 36.8 | 43.0 | 50.8 | 68.9 | 79.3 | 85.9 | 95.2 | Mean |
| 1.8 | 2.1 | 2.5 | 2.5 | 3.2 | 2.9 | 2.8 | 2.0 | 0.9 | Std Dev |
| Formulation # MPH1 | | | | | | | | | |
| 15.2 | 26.4 | 35.1 | 42.5 | 53.0 | 77.6 | 90.6 | 96.3 | 99.0 | Mean |
| 0.8 | 0.8 | 0.9 | 1.1 | 1.3 | 1.7 | 1.2 | 0.8 | 1.0 | Std Dev |
| Formulation # MPH5 | | | | | | | | | |
| 14.6 | 26.4 | 35.7 | 43.3 | 58.9 | 82.2 | 95.2 | 100.4 | 99.5 | Mean |
| 0.8 | 1.6 | 1.9 | 1.9 | 1.5 | 0.7 | 1.4 | 2.0 | 2.8 | Std Dev |
| Formulation # MPH6 | | | | | | | | | |
| 19.0 | 32.3 | 41.7 | 49.1 | 58.0 | 76.9 | 87.5 | 91.4 | 90.9 | Mean |
| 1.9 | 2.4 | 2.9 | 3.1 | 3.2 | 3.0 | 2.2 | 1.2 | 0.3 | Std Dev |
| Formulation # MPH7 | | | | | | | | | |
| 14.8 | 27.7 | 37.3 | 45.0 | 55.3 | 76.7 | 87.8 | 92.3 | 92.7 | Mean |
| 0.9 | 2.0 | 2.8 | 3.2 | 3.9 | 4.1 | 3.4 | 3.3 | 3.9 | Std Dev |
| Formulation # MPH8 | | | | | | | | | |
| 18.8 | 31.8 | 41.2 | 48.7 | 58.8 | 79.9 | 89.3 | 91.4 | 89.0 | Mean |
| 1.4 | 1.3 | 1.4 | 1.4 | 1.5 | 2.0 | 2.2 | 2.4 | 2.4 | Std Dev |

TABLE 8-continued

| Mean Cumulative Drug Released | | | | | | | | | |
|---|---|---|---|---|---|---|---|---|---|
| 0.5 hr | 1 hr | 1.5 hr | 2 hr | 3 hr | 6 hr | 9 hr | 12 hr | 24 hr | |
| Formulation MPH11 | | | | | | | | | |
| 15.3 | 27.5 | 34.8 | 42.3 | 54.0 | 78.0 | 92.5 | 99.5 | 104.3 | Mean |
| 1.7 | 3.1 | 2.2 | 1.9 | 2.2 | 1.4 | 1.9 | 1.3 | 1.3 | Std Dev |
| Formulation MPH12 | | | | | | | | | |
| 15.8 | 28.0 | 36.9 | 44.3 | 55.8 | 79.3 | 93.2 | 100.7 | 104.4 | Mean |
| 1.0 | 1.3 | 1.3 | 1.2 | 1.2 | 1.4 | 1.8 | 2.3 | 2.8 | Std Dev |
| Formulation MPH13 | | | | | | | | | |
| 14.9 | 27.6 | 37.5 | 45.7 | 58.5 | 84.9 | 97.6 | 101.7 | 104.3 | Mean |
| 1.0 | 1.4 | 1.9 | 2.3 | 3.2 | 4.0 | 2.0 | 1.0 | 0.4 | Std Dev |

Figure 17A:
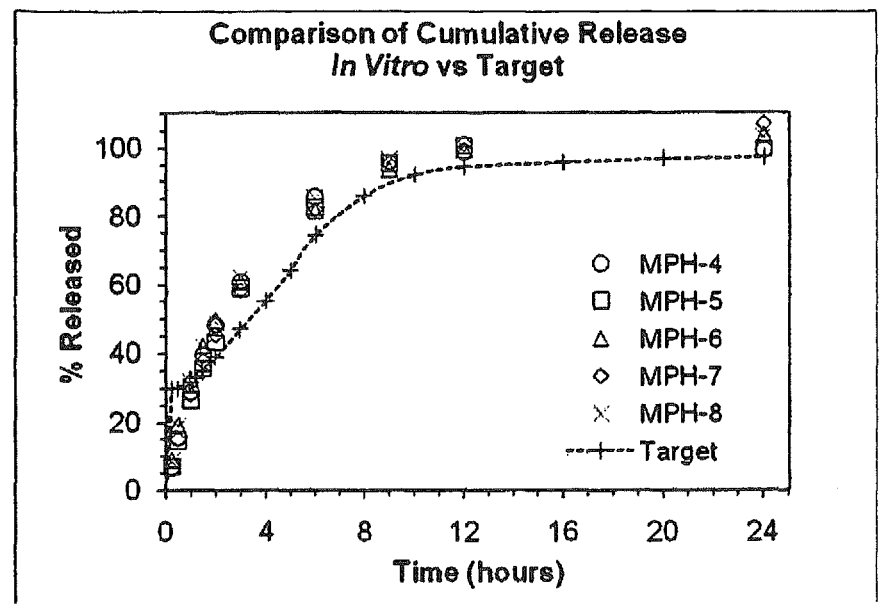
FIGS. 17A, 17B and 17C depict the results of Example 2b, where the in vitro dissolution cumulative release of methylphenidate from a number of candidate abuse-resistant methylphenidate oral dosage forms produced according to the invention are compared to a target in vitro methylphenidate release profile developed in accordance with the invention.
Figure 17B:
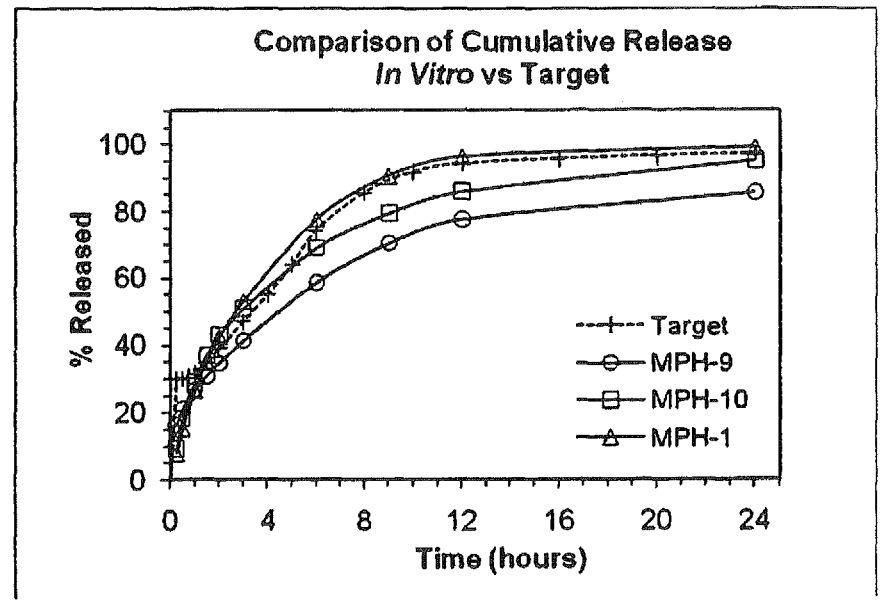
Figure 17C:
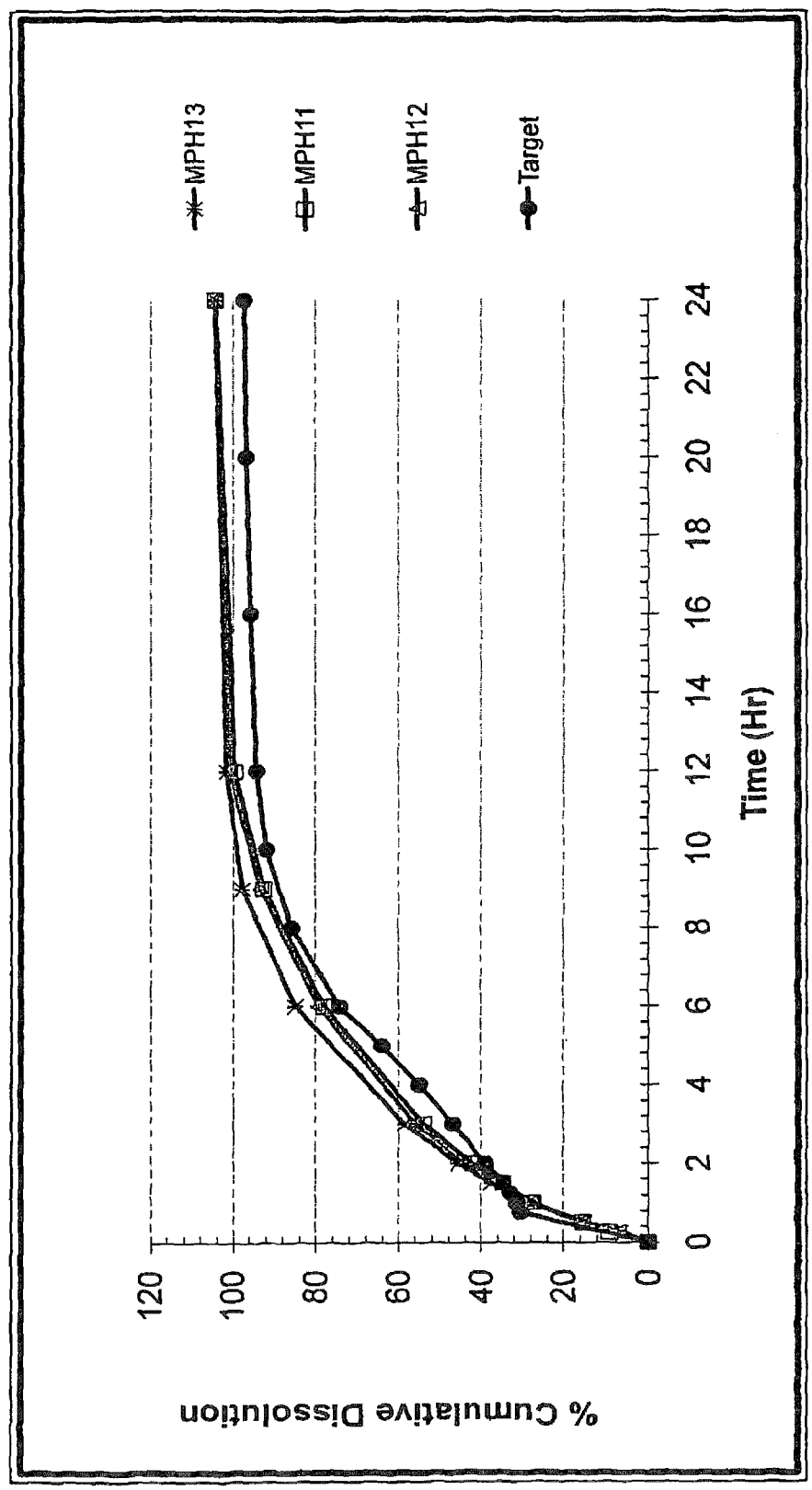

Finally, the cumulative release results were compared against the target in vitro release profile. FIGS. 17A, 17B and 17C depict the results of this comparison, where the in vitro dissolution cumulative release profiles of methylphenidate from the Test Capsules are compared to a target in vitro methylphenidate release profile developed in accordance with the invention. As can be seen, the MPH 1 and MPH11-MPH13 release profiles best match the target profile, except at short times.

Example 3: Analysis of Formulations (In Vitro Extraction and Volatilization Testing Procedures)

In order to assess the abuse-resistance performance of the abuse-resistant dosage forms prepared according to the present invention, the following in vitro extraction tests were developed. In particular, intentional abuse of controlled release pharmaceutical dosage forms will often times be carried out by simple extraction techniques that can separate most or all of the active agent from commercially available controlled release carrier systems using common household solvents. Accordingly, a panel of in vitro extraction tests was developed in order to assess the abuse-resistant performance of the dosage forms produced according to the instant invention.

Example 3a

Extraction in a Panel of Household Liquids

In order to assess the abuse-resistance performance of abuse-resistant dosage forms produced according to the present invention, a panel of tests to evaluate extraction of active agent from a dosage form into the following commonly available household solvents was developed as follows: vinegar (acetic acid), pH 2.5; cola soft drink, pH 2.5; baking soda solution (sodium bicarbonate), pH 8.2; 80 proof ethanol (40% v/v); and vegetable oil. The dosage forms of the present invention can be tested against this panel of common household solvents at both ambient or "room"

temperature (25° C.) and with preheated extraction solvents (heated to 60° C.). In addition, exceptional stressing, such as the use of microwave and freeze-and-crush pretreatment of the dosage forms prior to extraction in the above-noted solvents can also be carried out.

The materials and apparatus used in the solvent extraction panel study of this Example 3a are as follows. Standard laboratory equipment includes a shaker (Jeio Tech Shaking Incubator, Model SI-600), hot water bath, hot plate, centrifuge, microwave oven, glass mortar and pestle, a 250 mL glass bottle with cap, and a filtering unit (0.2 µm nylon membrane). The solvent reagents used in the extraction panel study are prepared as follows: distilled water, 200 proof ethanol (Spectrum) mixed in distilled water to provide 80 proof ethanol solvent; distilled white vinegar 5% acidity (Heinz); cola soft drink (Coke Cola Classic); vegetable oil (Canola); baking soda (Arm & Hammer), saturated solution prepared by adding 527 g of baking soda to 2 L distilled water, mixed vigorously for approximately 1 hour, allowed to settle and then filtered the supernatant using the 0.2 µm nylon membrane. The pH of the Vinegar, cola soft drink and saturated baking soda solution are determined using a pH meter and recorded prior to extraction studies.

The test procedures used for all of the solvents except the vegetable oil solvent are as follows. 240 mL of each extraction solvent is placed into separate extraction bottles. A dosage form is then added (if the dosage form is a solid tablet, the form is crushed and then dropped into the solvent, if the dosage form is a liquid capsule, the capsule is cut to open the shell, and the liquid contents are squeezed from the capsule into the solvent, and then the empty shell is dropped into the solvent). Extraction is initiated on the shaker using a constant speed of 150 rpm. Samples (1 mL) are withdrawn at 5, 20 and 60 minute time points. The samples are centrifuged at 10,000 rpm for 10 minutes, and about 0.5 mL of the supernatant is transferred into HPLC vials for analysis (HP Model 1200 or similar model). This extraction panel is then repeated wherein the extraction solutions are pre-warmed in a 60° C. water bath. The actual initial and final temperatures of the solvent solution are then taken.

Extraction in Oil

The test procedures used for the vegetable oil solvent are as follows. 2 tablespoons of the oil is placed into an extraction bottle. A dosage form is then added (if the dosage form is a solid tablet, the form is crushed and then dropped into the solvent, if the dosage form is a liquid capsule, the capsule is cut to open the shell, and the liquid contents are squeezed from the capsule into the solvent, and then the empty shell is dropped into the solvent). Extraction is initiated on the shaker using a constant speed of 150 rpm. Samples (1 mL) are withdrawn at 5, 15, 30 and 60 minute time points. The samples are centrifuged at 10,000 rpm for 10 minutes, and about 0.5 mL of the supernatant is transferred into HPLC vials for analysis (HP Model 1200 or similar model).

For the exceptional stressing test (microwave, and freeze-and-crush pretreatment of the dosage forms prior to extraction in the above-noted solvents), the test procedures are as follows.

Extraction after Microwaving

For the microwave stress analysis, dosage forms are added to empty extraction bottles (if the dosage form is a solid tablet, it is crushed and then dropped into the bottle, if the dosage form is a liquid capsule, the capsule is cut to open the shell, and the liquid contents are squeezed from the capsule into the bottle). The extraction bottles (4 at a time) are then microwaved for 2 min with power level set at "High" (power=90). Upon removal from the microwave, the appearance of the dosage form is recorded. Next, either 240 mL of distilled water or 240 mL of ethanol solvent is added to the extraction bottle (to assess extraction into water or ethanol). Extraction is initiated on the shaker using a constant speed of 150 rpm. Samples (1 mL) are withdrawn at 5-, 20- and 60-minute time points. The samples are centrifuged at 10,000 rpm for 10 minutes, and about 0.5 mL of the supernatant is transferred into HPLC vials for analysis (HP Model 1200 or similar model). This extraction procedure is then repeated on untested dosage forms after they have been allowed to equilibrate to room temperature (~1.5 hr) after microwave treatment.

Extraction after Physical and Mechanical Stress

For the freeze-and-crush (physical and mechanical stress) analysis, dosage forms are stored intact in a −80° C. freezer overnight (18 hrs). The test samples are then removed from the freezer and kept on dry ice until they are ready to be ground up. The frozen dosage forms are then placed into a freezer bag (about 9×12 cm) and crushed by pressing immediately in a glass mortar and pestle. Any excess (non-formulation containing) portion of the freezer bag is then removed to provide about a 9×9 cm test article that is quantitatively transferred (with the remaining freezer bag) into an extraction bottle. Next, either 240 mL of distilled water or 240 mL of the 100-proof ethanol solvent is added to the extraction bottle (to assess extraction into water or ethanol). Extraction is initiated on the shaker using a constant speed of 150 rpm. Samples (1 mL) are withdrawn at 5-, 20- and 60-minute time points. The samples are centrifuged at 10,000 rpm for 10 minutes, and about 0.5 mL of the supernatant is transferred into HPLC vials for analysis (HP Model 1200 or similar model).

Volatilization Test

In order to further assess the abuse-resistance performance of abuse-resistant dosage forms produced according to the present invention, the following in vitro volatilization test was developed. In particular, intentional abuse of controlled release pharmaceutical dosage forms may alternatively be carried out by volatilization (smoking, or free-basing) techniques that can liberate active agent (in immediately active form) from commercially available controlled release carrier systems. Accordingly, a preliminary in vitro volatilization test was developed in order to assess: (1) whether a free base form of an active agent (in this case, oxycodone) was more volatile than the salt (HCl) form; and (2) whether abuse-resistant dosage forms produced according to the instant invention can prevent inhalation abuse through volatilization.

For the study, 40 mg of neat active agent (oxycodone in free base form, oxycodone in HCl salt form), 40 mg Test Capsules were weighed into individual petri dishes. Each petri dish was fitted with a watch glass as a cover, and the covered test dishes were placed on a hot plate (setting 10). After 30 seconds each watch glass was replaced with a fresh watch glass, and this step was repeated three times (to obtain 4 time points). Any residue deposited on the bottom side of the test watch glasses was carefully transferred with an Alpha Swab (TX 761) into 40/60 ethanol/0.005M HCl solution, and the concentration of oxycodone solution was determined by HPLC. The observations taken during the test were as follows. The neat base form active agent (oxycodone free base form) vaporizes/sublimes upon heating, whereas there was extensive degradation and charring of the salt form active agent (oxycodone HCl). It was noted that vaporized drug (and solvents where present) escaped during each change of the watch glass, which may be at least partially responsible for the low recovery noted in the HPLC results below. In addition, the presence of solvents and other excipients in the Test Capsules made it difficult to volatilize the active agent, and there was a particularly noxious smell noted when the Test Capsules were volatilized.

Extraction in Aqueous Buffers Over a Range of pH 1-pH 12

In order to further assess the abuse-resistance performance of abuse-resistant dosage forms produced according to the present invention, an additional solvent extraction test was developed as follows. The extraction properties of six aqueous buffers over a range of pH 1-pH 12 was assessed. Specific buffer strengths were pH 1, pH 4, pH 6, pH 8, pH 10 and pH 12. The pH 1 buffer consisted of 0.1N HCl, the pH 4 buffer consisted of S mM acetate, and buffers of Ph 6, 10 and 12 consisted of 5 mM phosphate. Test Capsules were cut open and squeezed to exude the liquid contents and assure intimate contact of test solvents with the controlled release matrix. The Test Capsules were placed into test jars containing 240 mL of each buffer. The closed jars were vigorously shaken at 100 rpm for 60 minutes, with shaking interrupted to withdraw samples at 5, 20 and 60 minutes. The solvent samples taken at each testing interval were centrifuged and assayed for extracted active agent content by HPLC.

In Vitro Injection Abuse Resistance Evaluation

In order to further assess the abuse-resistance performance of abuse-resistant dosage forms produced according to the present invention, an in vitro Injection Abuse Resistance Evaluation was carried out to characterize the ability of abuse-resistant formulations such as those prepared according to the present invention to resist injection-based forms of abuse. In this regard, the characteristics of an injectable suspension are defined as syringeability and injectability. Syringeability pertains to the ability of a suspension to be drawn into an empty syringe through a hypodermic needle, while injectability address the ability of a suspension to be pushed from a pre-filled syringe through a hypodermic needle. Both characteristics depend upon the viscosity and physical characteristics of a test formulation.

For the test, placebo (no active agent) formulations were evaluated for syringeability and injectability to assess resistance to abuse by injection. The placebo formulations used in this study were prepared using the following raw materials: Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); and Cellulose Acetate Butyrate, grade 381-20 BP, ethanol washed (Eastman Chemicals) ("CAB"). The details of the placebo formulation used in this study are disclosed below in Table 9.

TABLE 9

| SAIB | TA | CAB | IPM | HEC | SiO$_2$ | BHT | (total) | |
|---|---|---|---|---|---|---|---|---|
| 43.19 | 28.80 | 5.0 | 15.0 | 6.0 | 2.0 | 0.02 | | (wt %) |
| 319.6 | 213.1 | 37.0 | 111.0 | 44.4 | 14.8 | 0.16 | 740.0 | (mg) |

The test equipment and apparatus used in this study included syringe barrel (Becton Dickinson (B-D) 3 mL Disposable Syringe with Leur-Lok Tip; hypodermic needles (B-D (305136) PrecisionGlide Needle 27G1.25; B-D (305125) PrecisionGlide Needle 25Ol; B-D (305190) PrecisionGlide Needle. IV 1.5, 21G; B-D (305185) Precision-Glide Needle Fill 1.5, 18G); and an Instron 5542 Load Frame, controlled by BLUEHILL software.

Initially, syringeability was assessed in two ways: first by attempting to draw the placebo formulation from a Test Capsule by piercing the capsule shell with the hypodermic needle and attempting to draw the formulation into the syringe; and second, by attempting to squeeze the formulation from a cut capsule into the posterior end of a syringe barrel (i.e., with the plunger removed). The syringeability analysis was conducted using placebo formulations equilibrated at room temperature (25° C.). Both of these techniques represent practices that may be employed by a drug abuser. Any placebo formulation mass successfully drawn or filled into the syringe was quantified and recorded.

Injectability was evaluated using the Instron Load Frame instrument to push the plunger of a pre-loaded syringe in an attempt to deliver the placebo formulation. The force required for successful injection of the placebo formulation or the force at which failure occurred was recorded by the instrument. The single-use syringe barrels were filled with approximately 1 g of the placebo formulation (range 0.64 to 1.14 g). Entrapped air was removed by application of vacuum while depressing the plunger to minimize variability in the injectability analysis. Testing was performed on two sets of placebo formulations that were equilibrated to either 25° C. or 37° C. Needles with gauge sizes of 18, 21, 25 and 27 were joined by a Luer-Lok fitting to the pre-loaded syringe barrel. Three different crosshead speeds (i.e., plunger depression rates) were evaluated for each needle gauge. Crosshead speeds of 150 mm/min, 550 mm/min, and 950 mm/min were selected based upon documented typical injection rates for parenteral administration. Three samples were tested at each set of conditions.

The results of this abuse-resistance test were as follows. Syringeability: it was not possible to draw the placebo formulation into the syringe using the largest bore needle (18 gauge) due to the high viscosity and thixotropy of the formulation. As a result, evaluation using smaller bore needles (21, 25 and 27 gauge) were not performed. Placebo formulation at room temperature was squeezed from an opened capsule into the posterior end of a tared syringe barrel. The weights successfully transferred into each of five syringes was recorded. A mean weight of 0.42 g (range 0.22-0.50 g, mean of 54%, range 28-64%) was transferred from the Test Capsules. Accordingly, syringeability was not achieved for any gauge needle in the study. In this regard, the high viscosity and sticky character of the placebo formulation prevented quantitative transfer of capsule contents into the syringe barrel.

Injectability of the placebo formulations at room temperature was only achieved using an 18 gauge needle at the slowest crosshead speed of 150 mm/min. At 37° C., the formulation is less viscous and injectability was achieved with all three samples using the 18 gauge needle at a speed of 150 mm/min, and with two of the three samples using an 18 gauge needle at a speed of 550 mm/min. Either load failures of mechanical failures occurred at both test temperatures, and at all three crosshead speeds with the 21, 25 and 27 gauge needles.

The following information was considered in interpreting the outcome of each test. Single use disposable syringes are rated to withstand an internal barrel pressure of 45 lb/in$^2$ for 30 seconds (corresponding to a pressure exerted on the plunger rod of 18.2 N). For 3 mL (ID=0.34 in.) disposable syringe barrels, 1 lb$_f$ applied to the plunger rod generates 11.0 lb/in$^2$ within the syringe barrel. The mean pinch force (Palmer Pinch) exerted by healthy males is 23 to 23.4 lb$_f$, The following failure modes were used to assess injectability in this study. Overall failure of the test was concluded upon failure of at least one sample with a triplicate test set. A Plunger Barrel failure occurs when excessive internal pressure causes the syringe barrel to flex, resulting in fluid bypassing the plunger stopper. This event is determined by observing the sample, or is evidenced by a declining load force profile in the Instron tracing. A Leur-Lok Coupling Failure occurs when excessive internal pressure causes the needle to separate from the syringe barrel. This failure event is determined by observing incomplete sample delivery from the syringe, or is evidenced by a precipitous drop in the load force profile in the Instron tracing. An Excessive Force failure occurs when the force required to successfully deliver fluid from the syringe exceeds 23.4 lb$_f$ (104 N), the average (Palmer) pinch force of a healthy male. This event is evident from the Instron tracing.

Successful injection of placebo formulation required comparable performance of all three test samples. The criterion for success was at least 80% delivery of the initial pre-filled mass. In addition, the Instron tracing should display a consistent profile of force applied during plunger travel. Even in cases where the force profile remained consistent during the test and resulted in delivery of placebo mass from the syringe, a force greater than 62 N was required to achieve delivery. This magnitude of force generates a barrel pressure of 153 lb$_f$/in$^2$, which is 340% of the pressure rated by the manufacturer.

These results of both the syringeability and injectability evaluations demonstrate the improbability of delivering an abuse-resistant controlled release formulation prepared according to the invention using common hypodermic needles such as those available to drug abusers. This is thought to be due to a combination of limitations of suitable syringe pressures, limitations of human strength and the highly viscous nature of the instant formulations.

Example 3b

The following in vitro Abuse Resistance Evaluation was carried out to characterize the in vitro abuse resistance performance of abuse resistant methylphenidate oral dosage forms prepared according to the present invention. More particularly, abuse-resistant methylphenidate oral dosage forms across a range of formulations were assessed for resistance to extraction in an ethanol solution. The abuse-resistant methylphenidate oral dosage forms used in this Example 3b were prepared using the following raw materials: methylphenidate ("MPH"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Gelucire 50/13 (Gattefosse) ("GEL"); and Miglyol 812 ("MIG"). The formulations were produced using the manufacturing process described in Example 1 above, and then filled into size #3 gelatin capsule shells to produce the dosage forms that were used as Test Capsules. The details of the formulations and the dosage forms containing the formulations of this Example 3b are disclosed below in Tables 10 and 11.

TABLE 10

| | Formulation by Weight Percent (wt %) | | | | | |
|---|---|---|---|---|---|---|
| Component | MPH1 40 mg | MPH2 48 mg | MPH3 48 mg | MPH11 48 mg | MPH12 48 mg | MPH13 48 mg |
| MPH | 20.00 | 20.00 | 20.00 | 20.00 | 20.00 | 20.00 |
| SAIB | 33.35 | 34.31 | 34.55 | 34.31 | 29.25 | 34.55 |
| TA | 22.23 | 22.87 | 23.03 | 22.87 | 20.89 | 23.03 |
| CAB | 4.80 | 5.20 | 6.40 | 5.21 | 5.58 | 6.42 |
| IPM | 13.60 | 12.80 | 12.80 | 12.80 | — | 12.80 |
| MIG | — | — | — | — | 16.0 | — |
| HEC | 0.00 | 2.40 | 0.00 | 2.40 | 4.80 | — |
| SiO$_2$ | 2.00 | 1.60 | 1.60 | 1.60 | 1.60 | 1.60 |
| BHT | 0.02 | 0.02 | 0.02 | 0.02 | 0.02 | 0.02 |
| GEL | 4.00 | 0.80 | 1.60 | 0.80 | 1.84 | 1.60 |

TABLE 11

| | Formulation by Mass (mg) | | | | | |
|---|---|---|---|---|---|---|
| Component | MPH1 40 mg | MPH2 48 mg | MPH3 48 mg | MPH11 48 mg | MPH12 48 mg | MPH13 48 mg |
| MPH | 40.00 | 48.00 | 48.00 | 48.00 | 48.00 | 48.00 |
| SAIB | 66.70 | 82.34 | 82.92 | 82.30 | 70.20 | 82.90 |
| TA | 44.46 | 54.89 | 55.27 | 54.90 | 50.10 | 55.30 |
| CAB | 9.60 | 12.48 | 15.36 | 12.50 | 13.40 | 15.40 |
| IPM | 27.20 | 30.72 | 30.72 | 30.70 | — | 30.70 |
| MIG | — | — | — | — | 38.40 | — |
| HEC | 0.00 | 5.76 | 0.00 | 5.80 | 11.50 | — |
| SiO$_2$ | 4.00 | 3.84 | 3.84 | 3.80 | 3.80 | 3.80 |
| BHT | 0.04 | 0.05 | 0.05 | 0.05 | 0.05 | 0.05 |
| GEL | 8.00 | 1.92 | 3.84 | 1.90 | 4.40 | 3.80 |
| Total | 200.00 | 240.00 | 240.00 | 240.00 | 240.00 | 240.00 |

The in vitro Abuse Resistance Evaluation used the following Test Capsules: three (n=3) each of formulations MPH1-MPH3 and MPH11-MPH13.

The ethanol solution extraction study was carried out substantially as described herein above, using the same apparatus, reagents and methods described above, with the following exceptions: the extraction solution was 60 mL of 80 proof ethanol (40%); and sampling was conducted at time=0.5 hr and 3 hours. The results of the extraction study are provided below in Table 12.

TABLE 12

| | Amount of Methylphenidate Extracted in 80 Proof Ethanol (% of dose) Time (hr.) | |
|---|---|---|
| | 0.5 | 3 |
| | MPH1 | |
| Mean | 18.4 | 63.0 |
| Std Dev. | 0.9 | 0.9 |
| | MPH2 | |
| Mean | 7.2 | 25.7 |
| Std Dev. | 0.5 | 1.7 |
| | MPH3 | |
| Mean | 6.1 | 22.9 |
| Std Dev. | 0.6 | 1.3 |
| | MPH11 | |
| Mean | 10 | 32 |
| Std Dev. | 1 | 3 |

TABLE 12-continued

| | Amount of Methylphenidate Extracted in 80 Proof Ethanol (% of dose) Time (hr.) | |
|---|---|---|
| | 0.5 | 3 |
| | MPH12 | |
| Mean | 10 | 40 |
| Std Dev. | 1 | 2 |
| | MPH13 | |
| Mean | 11 | 43 |
| Std Dev. | 2 | 4 |

Example 3c

The following in vitro Abuse Resistance Evaluation was carried out to compare the in vitro abuse resistance performance of abuse resistant methylphenidate oral dosage forms prepared according to the present invention over a greater number of sampling points. More particularly, abuse-resistant methylphenidate oral dosage forms across a range of formulations were assessed for resistance to extraction in an ethanol solution. The abuse-resistant methylphenidate oral dosage forms used in this Example 3c were prepared using the following raw materials: methylphenidate ("MPH"); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Gelucire 50/13 (Gattefosse) ("GEL"); and Miglyol 812 ("MIG"). The formulations were produced using the manufacturing process described in Example 1 above, and then filled into size #3 gelatin capsule shells to produce the dosage forms that were used as Test Capsules. The details of the formulations used in this Example 3c are disclosed below in Table 13.

The in vitro Abuse Resistance Evaluation used the following Test Capsules: three (n=3) each of formulations MPH1, MPH5-MPH7, MPH10-MPH12, MPH14 and MPH15.

The ethanol solution extraction study was carried out substantially as described herein above, using the same apparatus, reagents and methods described above, with the following exceptions: the extraction solution was 60 mL of 80 proof ethanol (40%); and sampling was conducted at time=20 minutes, 45 minutes, 1 hour and then at 3 hours. The results of the extraction study are provided below in Table 14.

TABLE 14

| | Amount of Methylphenidate Extracted in 80 Proof Ethanol (% of dose) Time | | | |
|---|---|---|---|---|
| | 20 min | 45 min | 1 hr | 3 hrs |
| | MPH1 | | | |
| Mean | 15 | 29 | 35 | 63 |
| Std Dev. | 3 | 2 | 2 | 4 |
| | MPH5 | | | |
| Mean | 5 | 10 | 13 | 27 |
| Std Dev. | 1 | 2 | 1 | 2 |
| | MPH6 | | | |
| Mean | 4 | 7 | 9 | 19 |
| Std Dev. | 0 | 2 | 2 | 2 |
| | MPH7 | | | |
| Mean | 3 | 6 | 8 | 18 |
| Std Dev. | 1 | 1 | 2 | 2 |
| | MPH10 | | | |
| Mean | 12 | 24 | 30 | 57 |
| Std Dev. | 1 | 1 | 0 | 2 |
| | MPH11 | | | |
| Mean | 4 | 8 | 10 | 22 |
| Std Dev. | 0 | 1 | 0 | 1 |

TABLE 13

| | Formulation byWeight Percent (wt %) | | | | | | | | |
|---|---|---|---|---|---|---|---|---|---|
| | MPH1 40 mg | MPH5 40 mg | MPH6 48 mg | MPH7 48 mg | MPH10 40 mg | MPH11 48 mg | MPH12 48 mg | MPH14 40 mg | MPH15 36 mg |
| MPH | 20.00 | 20.00 | 20.00 | 15.00 | 20.00 | 20.00 | 20.00 | 13.09 | 20.00 |
| SAIB | 33.35 | 34.55 | 35.48 | 37.74 | 33.83 | 34.29 | 29.25 | 38.32 | 35.99 |
| TA | 22.23 | 23.03 | 23.66 | 25.16 | 22.55 | 22.87 | 20.89 | 25.54 | 23.99 |
| IPM | 13.60 | 12.80 | 12.54 | 13.33 | 12.80 | 12.80 | — | 13.91 | 12.80 |
| CAB | 4.80 | 6.40 | 5.10 | 5.43 | 5.21 | 5.21 | 5.58 | 5.65 | 4.00 |
| $SiO_2$ | 2.00 | 1.60 | 1.60 | 1.67 | 1.60 | 1.60 | 1.60 | 1.74 | 1.60 |
| GEL | 4.00 | 1.60 | 1.60 | 1.67 | 4.00 | 0.80 | 1.84 | 1.74 | 1.60 |
| MIG | — | — | — | — | — | — | 16.0 | — | — |
| HEC | — | — | — | — | — | 2.42 | 4.80 | — | — |
| BHT | 0.02 | 0.02 | 0.02 | 0.02 | 0.02 | 0.02 | 0.02 | 0.02 | 0.02 |
| Total | 100.00 | 100.00 | 100.00 | 100.01 | 100.00 | 100.01 | 99.98 | 100.01 | 100.00 |

TABLE 14-continued

Amount of Methylphenidate
Extracted in 80 Proof Ethanol (% of dose)
Time

|  | 20 min | 45 min | 1 hr | 3 hrs |
|---|---|---|---|---|
| | | MPH12 | | |
| Mean | 9 | 18 | 22 | 43 |
| Std Dev. | 0 | 1 | 1 | 3 |
| | | MPH14 | | |
| Mean | 9 | 23 | 29 | 55 |
| Std Dev. | 1 | 2 | 2 | 2 |
| | | MPH15 | | |
| Mean | 20 | 35 | 43 | 72 |
| Std Dev. | 2 | 2 | 0 | 2 |

Example 3d

The following in vitro dissolution tests and Abuse Resistance Evaluations were carried out to compare both the in vitro controlled release and abuse resistance performance of methylphenidate oral dosage forms prepared in two different manners. More particularly, abuse-resistant methylphenidate oral dosage forms were prepared using two distinct manufacturing processes. The sample dosage forms were then tested for cumulative release performance and also for resistance to extraction in an ethanol solution. Finally, the cumulative release results for one of the sample dosage forms were compared against the target in vito release profile developed in Example 2b above. The abuse-resistant methylphenidate oral dosage forms used in this Example 3d were prepared using the following raw materials: methylphenidate ("MPH"); Isopropyl Myristath, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Triethyl Citrate ("TEC"); Precirol ATO5 ("PREC"); Ethyl Cellulose ("EC"); Miglyol 812 ("MIG"); Tween 80 ("TW80"); Gelucire 50/13 (Gattefosse) ("GEL"); and Poloxamer 124 ("PLX").

Five different formulations were produced using the manufacturing process described in Example 1 above, and then filled into size #3 gelatin capsule shells to produce dosage forms that were used as the first series of Test Capsules. Details of the formulations produced using the first manufacturing process are disclosed below in Table 15.

TABLE 15

Formulation by Weight Percent (wt %)

|  | MPH16 48 mg | MPH17 48 mg | MPH18 48 mg | MPH19 36 mg | MPH20 48 mg |
|---|---|---|---|---|---|
| MPH | 20.00 | 20.00 | 20.00 | 20.00 | 20.00 |
| SAIB | 30.00 | 31.42 | 33.16 | 33.16 | 32.46 |
| SiO$_2$ | — | 1.60 | 1.60 | 1.60 | 1.60 |
| PREC | 15.00 | 11.20 | 11.20 | 11.20 | — |
| TEC | 35.00 | 24.17 | — | — | — |
| MIG | — | 9.60 | 25.51 | 25.51 | 11.20 |
| TW80 | — | — | 6.52 | — | — |
| PLX | — | — | — | 6.52 | — |
| EC | — | 2.00 | 2.00 | 2.00 | — |
| CAB | — | — | — | — | 6.40 |

TABLE 15-continued

Formulation by Weight Percent (wt %)

|  | MPH16 48 mg | MPH17 48 mg | MPH18 48 mg | MPH19 36 mg | MPH20 48 mg |
|---|---|---|---|---|---|
| TA | — | — | — | — | 24.97 |
| GEL | — | — | — | — | 0.96 |
| HEC | — | — | — | — | 2.40 |
| BHT | 0.02 | 0.02 | 0.02 | 0.02 | 0.02 |
| Total | 100.02 | 100.01 | 100.01 | 100.01 | 100.01 |

Next, five different formulations were produced using a three-stage manufacturing processes to provide an initial (early) increasing release component, a second (non-ascending) controlled release component, and a barrier layer that were then combined into single size #3 gelatin capsule shells to produce dosage forms that were used as the second series of Test Capsules.

The initial increasing release components were prepared using the following raw materials: methylphenidate HCl ("MPH"); Colloidal silicon dioxide (Cabosil®, Cabot Corp) ("SiO$_2$"); Butylated hydroxyl toluene, NF ("BHT"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Miglyol 812 ("MIG"); Tween 80 ("TW80"); Gelucire 50/13 (Gattefosse) ("GEL"); Precirol ATO5 ("PREC"); and Ac-Di-Sol (Croscarmellose Sodium), ("ADS"). Details of each of the initial increasing release components of the formulations produced using the three stage manufacturing process are disclosed below in Table 16.

TABLE 16

Formulation of Increasing Release
Components by Weight Percent (wt %)

|  | MPH21 8 mg | MPH22 8 mg | MPH23 8 mg | MPH24 8 mg | MPH25 8 mg |
|---|---|---|---|---|---|
| MPH | 20.00 | 6.67 | 6.67 | 20.00 | 20.00 |
| SAIB | 37.00 | 43.0 | 33.00 | 35.99 | 35.99 |
| SiO$_2$ | 1.00 | 1.00 | 1.00 | 1.60 | 1.60 |
| ADS | — | 4.00 | — | 4.00 | 4.00 |
| MIG | — | 43.0 | 44.00 | 35.99 | 35.99 |
| CAB | 1.00 | — | — | — | — |
| TA | 37.00 | — | — | — | — |
| GEL | 4.00 | 2.00 | — | 2.40 | 2.40 |
| PREC | — | — | 7.5 | — | — |
| TW80 | — | — | 7.5 | — | — |
| BHT | — | — | — | 0.02 | 0.02 |
| Total | 100.00 | 99.67 | 101.00 | 100.00 | 100.00 |

The second (non-ascending) controlled release components were prepared using the following raw materials: methylphenidate HCl ("MPH"); Colloidal silicon dioxide (Cabosil®, Cabot Corp) ("SiO$_2$"); Butylated hydroxyl toluene, NF ("BHT"); Sucrose Acetate Isobutyrate (Eastman. Chemicals), ("SAIB"); Triacetin USP ("TA"); Cellulose Acetate Butyrate, grade 381-20 BP, ethanol washed (Eastman Chemicals) ("CAB"); Miglyol 812 ("MIG"); Tween 80 ("TW80"); Gelucire 50/13 (Gattefosse) ("GEL"); Precirol ATO5 ("PREC"); Ethyl Cellulose ("EC"); and Hydroxyethyl cellulose, NF ("HEC"). Details of each of the second (non-ascending) controlled release components of the formulations produced using the three stage manufacturing process are disclosed below in Table 17.

TABLE 17

Formulation of Second (Non-Ascending) CR Components by Weight Percent (wt %)

|  | MPH21 40 mg | MPH22 40 mg | MPH23 40 mg | MPH24 40 mg | MPH25 40 mg |
|---|---|---|---|---|---|
| MPH | 20.00 | 33.33 | 33.33 | 20.00 | 20.00 |
| SAIB | 33.00 | 30.67 | 30.67 | 33.16 | 33.16 |
| SiO$_2$ | 1.00 | 1.00 | 1.00 | 1.60 | 1.60 |
| PREC | — | — | — | 11.20 | 11.20 |
| MIG | 11.00 | 25.00 | 25.00 | 25.51 | 25.51 |
| CAB | 6.00 | — | — | — | — |
| TA | 26.00 | — | — | — | — |
| GEL | 1.00 | 10.00 | 10.00 | — | — |
| HEC | 2.00 | — | — | — | — |
| TW80 | — | — | — | 6.52 | 6.52 |
| EC | — | 1.00 | 1.00 | 2.00 | 2.00 |
| BHT | — | — | — | 0.02 | 0.02 |
| Total | 100.00 | 101.00 | 101.00 | 100.01 | 100.01 |

The barrier layer was made from the combination of Paraffin 140/145 (25 wt %) and Mineral Oil, White, Light (75 wt %).

The initial increasing release component for the MPH23 formula was compounded as follows. The SAIB was pre-heated to 65° C.±5° C. over night. The compound mixture was then maintained at 60° C.±5° C. for the remainder of the compounding process. Next, the MIG was added to the SAIB and mixed at 600 rpm for 15 minutes, after which the GEL was added to the mixture and mixed at 600 rpm for 15 minutes. A pre-made MIG/BHT solution was added to the compounding mixture and mixed at 600 rpm for 15 minutes, after which the SiO$_2$ was added and then mixed at 1,000 rpm for 20 minutes followed by a homogenization step at 9,600 rpm for 10 minutes. Next, the ADS was added to the compounding mixture and mixed at 1,500 rpm for 20 minutes, followed by addition of the MPH with mixing at 1,500 rpm for 30 minutes, and finished with a homogenization step at 9,600 rpm for 10 minutes to provide the initial increasing release component.

The second (non-ascending) controlled release component for the MPH23 formulation was compounded as follows. The SAIB was pre-heated to 65° C.±5° C. over night. The compound mixture was then maintained at 60° C.±5° C. for the remainder of the compounding process. Next, the MIG was added to the SAIB and mixed at 600 rpm for 15 minutes, after which the TW80 was added to the mixture and mixed at 600 rpm for 20 minutes. A pre-made MIG/BHT solution was added to the compounding mixture and mixed at 600 rpm for 15 minutes, after which the PREC was added to the compounding mixture and mixed at 800 rpm for 20 minutes. Next, the SiO$_2$ was added and then mixed at 1,000 rpm for 20 minutes followed by a homogenization step at 9,600 rpm for 10 minutes. The EC was then added to the compounding mixture and mixed at 1,500 rpm for 20 minutes, followed by addition of the MPH with mixing at 1,500 rpm for 30 minutes, and finished with a homogenization step at 9,600 rpm for 10 minutes to provide the second (non-ascending) controlled release component.

The barrier layer was compounded at 65° C.±5° C. by mixing the mineral oil at 600 rpm for 15 minutes, adding the paraffin and then mixing at 600 rpm for 30 minutes.

The three components for the other formulations were made in substantially the same manner as the MPH23 components.

The capsules were filled into size #3 gelatin capsule shells to produce dosage forms that were used as the first series of Test Capsules as follows: the second (non-ascending) controlled release component was filled into the bottom of the bottom of the capsule and allowed to cool; next the barrier layer was filled over the cooled layer, followed by filling of the initial increasing release component; and then the capsule cap was placed over the top. The Test Capsules were then ready for dissolution testing and the Abuse Resistance Evaluation.

The dissolution study was carried out using the apparatus, reagents and methods of the Method 1 dissolution test described above, with the following exceptions: sample timepoints were either at 0.25 hour, 0.5 hour, 1, 1.5, 2, 3, 6, 12 and 24 hour; or at 0.25 hour, 1, 3, 12 and 24 hour. Dissolution results were obtained on the following Test Capsules: four (n=4) each of formulations MPH16-MPH25. The mean dissolution data from the Test Capsules are summarized below in Table 18.

TABLE 18

| Mean Cumulative Drug Released | | | | | | | | | |
|---|---|---|---|---|---|---|---|---|---|
| 0.25 hr | 0.5 hr | 1 hr | 1.5 hr | 2 hr | 3 hr | 6 hr | 12 hr | 24 hr | |
| Formulation # MPH16 | | | | | | | | | |
| 6% | 12% | 20% | 26% | 32% | 40% | 61% | 82% | 96% | Mean |
| 0 | 0 | 1 | 1 | 1 | 2 | 3 | 5 | 6 | SD |
| Formulation # MPH17 | | | | | | | | | |
| 4% | 8% | 13% | 17% | 20% | 26% | 41% | 61% | 86% | Mean |
| 1 | 1 | 1 | 1 | 2 | 3 | 4 | 5 | 4 | SD |
| Formulation # MPH18 | | | | | | | | | |
| 8% | 17% | 30% | 40% | 47% | 59% | 80% | 95% | 96% | Mean |
| 1 | 1 | 1 | 1 | 1 | 1 | 1 | 2 | 2 | SD |
| Formulation # MPH19 | | | | | | | | | |
| 5% | 10% | 17% | 24% | 29% | 37% | 55% | 76% | 95% | Mean |
| 0 | 1 | 1 | 1 | 1 | 1 | 1 | 2 | 2 | SD |
| Formulation # MPH20 | | | | | | | | | |
| 7% | | 29% | | | 60% | | 103% | 104% | Mean |
| | | | | | | | | | SD |

TABLE 18-continued

| Mean Cumulative Drug Released | | | | | | | | | |
|---|---|---|---|---|---|---|---|---|---|
| 0.25 hr | 0.5 hr | 1 hr | 1.5 hr | 2 hr | 3 hr | 6 hr | 12 hr | 24 hr | |
| Formulation # MPH21 | | | | | | | | | |
| 12% | 20% | 34% | 44% | 51% | 64% | 86% | 100% | 103% | Mean<br>SD |
| Formulation # MPH22 | | | | | | | | | |
| 13% | 22% | 36% | 45% | 53% | 65% | 84% | 92% | 94% | Mean<br>SD |
| Formulation # MPH23 | | | | | | | | | |
| 11% | 19% | 31% | 40% | 46% | 58% | 80% | 94% | 97% | Mean<br>SD |
| Formulation # MPH24 | | | | | | | | | |
| 23%<br>2 | 29%<br>1 | 36%<br>2 | 42%<br>2 | 48%<br>2 | 55%<br>2 | 73%<br>2 | 93%<br>2 | 100%<br>2 | Mean<br>SD |
| Formulation # MPH25 | | | | | | | | | |
| 23%<br>1 | 31%<br>2 | 40%<br>33 | 47%<br>3 | 53%<br>4 | 64%<br>5 | 87%<br>5 | 100%<br>2 | 101%<br>1 | Mean<br>SD |

The in vitro Abuse Resistance Evaluation used the following Test Capsules: three (n=3) each of formulations MPH16-MPH20, MPH22 and MPH23.

The ethanol solution extraction study was carried out substantially as described herein above, using the same apparatus, reagents and methods described above, with the following exceptions: the extraction solution was 60 mL of 80 proof ethanol (40%); and sampling was conducted either: (i) at time=30 minutes and then at 3 hours; or (ii) at time=20 minutes, 45 minutes, 1 hour and then at 3 hours. The results of the extraction study are provided below in Table 19.

TABLE 19

| Amount of Methylphenidate Extracted in 80 Proof Ethanol (% of dose) | | | | |
|---|---|---|---|---|
| Time | | | | |
| 20 min | 30 min | 45 min | 1 hr | 3 hrs |
| MPH16 | | | | |
| 5 | — | 12 | 16 | 37 |
| 1 | — | 2 | 1 | 3 |
| MPH17 | | | | |
| 9 | — | 15 | 18 | 33 |
| 1 | — | 0 | 1 | 2 |
| MPH18 | | | | |
| 10 | — | 17 | 20 | 32 |
| 0 | — | 2 | 1 | 2 |
| MPH19 | | | | |
| 5 | — | 9 | 11 | 18 |
| 1 | — | 2 | 2 | 3 |
| MPH20 | | | | |
| — | 8 | — | — | 43 |
| — | — | — | — | — |
| MPH22 | | | | |
| — | 28 | — | — | 53 |
| — | — | — | — | — |
| MPH23 | | | | |
| — | 14 | — | — | 49 |
| — | — | — | — | — |

Note: First row of each formulation is Mean, second row is Std Dev.

Figure 18:
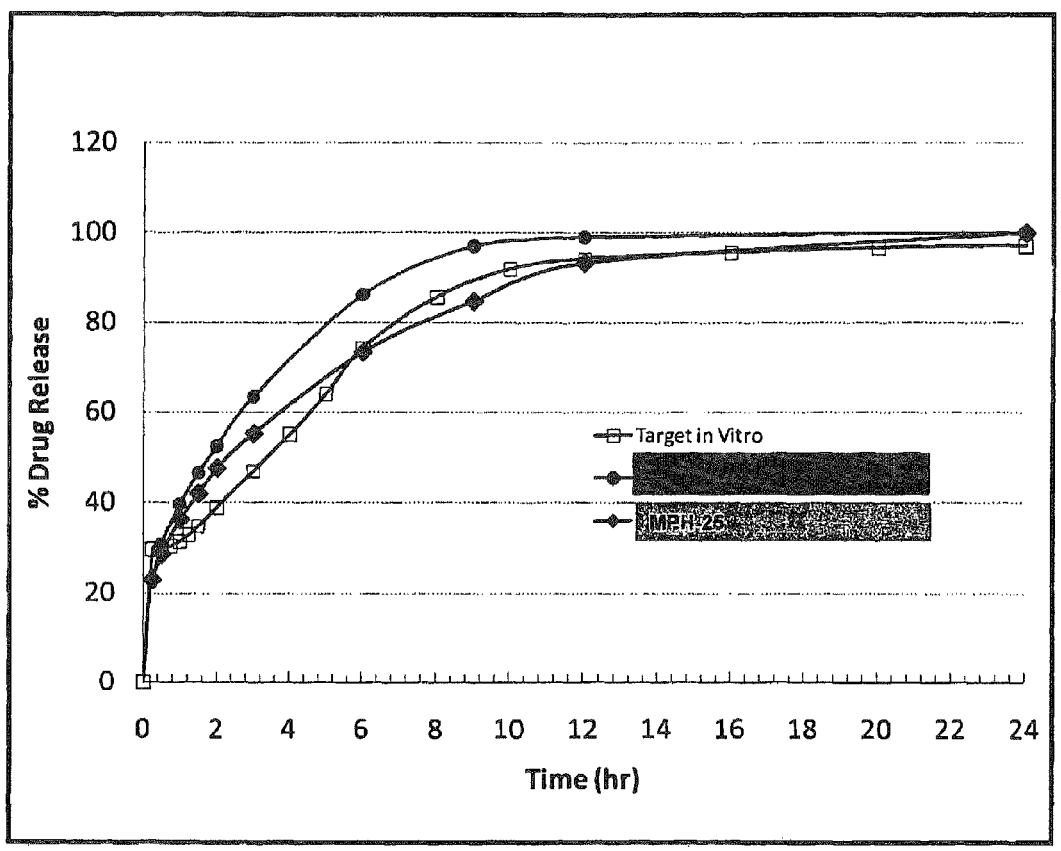
FIG. 18 depicts results from Example 3d, where the in vitro dissolution cumulative release of methylphenidate from a number of candidate abuse-resistant methylphenidate oral dosage forms produced according to the invention are compared to a target in vitro methylphenidate release profile developed in accordance with the invention.

Finally, the cumulative release results from the MPH24 and MPH25 Test Capsules were compared against the target in vitro release profile developed in Example 2b above. FIG. 18 depicts the results of this comparison, where the in vitro dissolution cumulative release profiles of methylphenidate from the Test Capsules are compared to a target in vitro methylphenidate release profile developed in accordance with the invention. As can be seen, the MPH24 and MPH25 release profiles match the target profile.

Example 4: Analysis of Formulations (Formulation Viscosity Testing Procedures)

In order to assess the viscosity of abuse resistant oral dosage forms produced according to the present invention, the following viscosity tests were developed. Both standard and dynamic viscosity measurements may be obtained using these tests. The viscosity testing apparatus used in the methods described in this Example 4 are Brookfield Digital Rheometers. The two specific models used are the following: JPII, Model HBDV-III+CP with a programmable/digital Controller Model 9112; and JPI, Model LVDV-III+CP, with an Immersion Circulator Model 11228. For both rheometer models the CPE Spindle 52 was used. For Dynamic Rheology, the dynamic rheology of the formulations can be measured using an Anton Paar Physica MCR301 rheometer (Anton Paar USA, Ashland, Va.) that is equipped with temperature and oscillatory strain control modules.

Sample formulations can be presented in two different formats for the viscosity testing methods, either as bulk formulation or as single dosage forms (e.g., gelatin capsules). For bulk formulation testing, 0.5 mL of the formulation is injected directly into the rheometer cup. When testing dosage forms, two gelatin capsules are needed for each measurement. The gelatin capsules are opened using a razor blade and a clean cutting surface. The contents are then squeezed out and placed in the rheometer cup.

Typical temperature conditions for the viscosity testing methods are 37° C. for most single point measurements, and 30° C., 40° C., 50° C., and 60° C. for temperature profiles. For each sample two different shear rates measured: $1^{st}$—low shear, an rpm setting is selected to provide a torque value between 10-15%; and 2$^{nd}$—high shear, an rpm setting is selected to give a torque value between 20-90%

Data collection of the viscosity measurements is carried out using standard techniques. For example, the Brookfield Digital Rheometer data report screen automatically displays the rotational speed, spindle number, torque value (%), and the viscosity for manual recording.

Finally, complex viscosity of formulation samples can be measured using varying oscillatory strain in the linear viscoelastic regime. Here, the intrinsic complex viscosity of a sample formulation at rest can be obtained based on a mathematical curve fit of empirical data points. The advantage of the dynamic oscillatory experiment is that it probes the sample formulation material without destroying the material's microstructure.

Example 5: In Vivo Analysis of Formulations (Human Clinical Trials, Pharmacokinetic Studies)

In order to assess the in vivo abuse resistance performance of abuse-resistant methylphenidate oral dosage forms prepared in accordance with the present invention, the following human clinical trails are carried out.

Example 5a

The following in vivo Abuse Resistance Evaluation study is designed as a single-center, four-way crossover PK study to assess the effect of physical disruption of the controlled release carrier system on the release of the methylphenidate active agent from abuse-resistant oral dosage forms produced according to the present invention. The study dosage forms (capsules containing methylphenidate) are administered either intact or crushed with alcohol. For comparison, methylpheniate controlled release tablets such as Concerta or Metadate CD of equal dosage strength are administered intact or crushed with alcohol, as well as an equal dose of an oral solution of methylphenidate as a comparator of an immediate release in order to represent a "worst-case scenario".

All administrations are in the fasted state unless a Test Capsule or comparison tablet is subject to a food effect, in which case administrations are in the fed state (30 minutes after a standardized breakfast).

During each study period, 3 mL blood samples are obtained prior to each dosing and following each dose at selected times through 96 hours post-dose. Blood samples are collected in vacutainer tubes containing EDTA as a preservative.

Plasma samples are analyzed for methylphenidate and its major metabolites using a validated LC-MS-MS procedure. Concentration-time data are transferred into WinNonlin, and analyzed using noncompartmental methods. These PK analyses are suitable to determine pharmacokinetic parameters such as mean $C_{max}$, $T_{max}$, AUC, etc. Effects of crushing Test Capsules are then assessed for evidence of dose dumping, and compared to PK performance of intact Test Capsules, intact and crushed controlled release control tablets, and the IR control.

Example 5b

The following in vivo Abuse Resistance Evaluation study is designed as a single-center, three-way crossover PK study to determine the release rate of methylphenidate after dissolving the study abuse-resistant oral dosage forms in the buccal cavity of healthy volunteers. The study dosage forms (Test Capsules) are administered and allowed to dissolve in the buccal cavity for 10 minutes to compare with same strength study dosage forms administered intact and swallowed immediately as intended, and an oral solution of immediate release (IR) methylphenidate in order to represent a "worst-case scenario".

All administrations are in the fasted state unless a Test Capsule or IR comparator is subject to a food effect, in which case administrations are in the fed state (30 minutes after a standardized breakfast).

During each study period, 3 mL blood samples are obtained prior to each dosing and following each dose at selected times through 96 hours post-dose. Blood samples are collected in vacutainer tubes containing EDTA as a preservative.

Plasma samples are analyzed for methylphenidate and its major metabolites using a validated LC-MS-MS procedure. Concentration-time data are transferred into WinNonlin, and analyzed using noncompartmental methods. These PK analyses are suitable to determine pharmacokinetic parameters such as mean $C_{max}$, $T_{max}$, AUC, etc. Effects of holding Test Capsules in the buccal cavity are then assessed for evidence of dose dumping, and compared to PK performance of intact Test Capsules and the IR control.

Example 5c

The following in vivo Abuse Resistance Evaluation study is designed as a single-center, randomized crossover study to assess the effect of rigorous mastication on the rate and extent of absorption of methylphenidate in abuse-resistant oral dosage forms in comparison with the same dosage forms swallowed whole (both under fed conditions) and methylphenidate IR solution. The study dosage forms (Test Capsules) are administered and chewed vigorously before swallowing to compare with same strength study dosage forms administered intact and swallowed immediately as intended, and an oral solution of immediate release (IR) methylphenidate in order to represent a "worst-case scenario".

All administrations are in the fasted state unless a Test Capsule or IR comparison tablet is subject to a food effect, in which case administrations are in the fed state (30 minutes after a standardized breakfast).

During each study period, 3 mL blood samples are obtained prior to each dosing and following each dose at selected times through 96 hours post-dose. Blood samples are collected in vacutainer tubes containing EDTA as a preservative.

Plasma samples are analyzed for methylphenidate and its major metabolites using a validated LC-MS-MS procedure. Concentration-time data are transferred into WinNonlin, and analyzed using noncompartmental methods. These PK analyses are suitable to determine pharmacokinetic parameters such as mean $C_{max}$, $T_{max}$, AUC, etc. Effects of chewing the Test Capsules prior to swallowing are then assessed for evidence of dose dumping, and compared to PK performance of intact Test Capsules and the IR control.

Example 5d

The following in Vivo Abuse Resistance Evaluation study is designed as a single-center, four-way crossover PK study to determine the rate and extent of absorption of methylphenidate in abuse-resistant oral dosage forms (Test Capsules) when co-administered with 240 mL of 4% ethanol, 20% ethanol and 40% ethanol in comparison to 240 mL of water.

All administrations are in the fasted state unless the Test Capsule is subject to a food effect, in which case administrations are in the fed state (30 minutes after a standardized breakfast).

During each study period, 3 mL blood samples are obtained prior to each dosing and following each dose at selected times through 96 hours post-dose. Blood samples are collected in vacutainer tubes containing EDTA as a preservative.

Plasma samples are analyzed for methylphenidate and its major metabolites using a validated LC-MS-MS procedure. Concentration-time data are transferred into WinNonlin, and analyzed using noncompartmental methods. These PK analyses are suitable to determine pharmacokinetic parameters such as mean $C_{max}$, $T_{max}$, AUC, etc. Effects of co-administration of the Test Capsules with alcohol are compared to PK performance of co-administration with water, and assessed for evidence of dose dumping.

Example 5e

In order to assess the in vivo controlled release performance of abuse-resistant methylphenidate oral dosage forms prepared in accordance with the present invention, the following human clinical trail is carried out. The study is designed as a single-center, three-way crossover, food effect, PK study to determine the rate and extent of absorption of methylphenidate in abuse-resistant oral dosage forms (Test Capsules) when administered in a fasted state, after consumption of a low fat meal, and after consumption of a high fat meal.

All study groups fast overnight for at least 10 hours. Study groups receiving the "high-fat" standardized meal are provided 2 slices of toasted white bread spread with butter, two eggs fried in butter, two slices of bacon, 2 oz hash-browned potatoes, and 8 oz whole milk (approximately 33 g protein, 58 to 75 g fat, 58 g carbohydrate, 870 to 1020 calories) at least 30 minutes prior to dosing. Study groups receiving the "low-fat" standardized meal are provided one slice of toasted white bread spread with butter or jelly, 1 oz dry cereal (corn flakes), 8 oz skim milk, 6 oz orange juice, and one banana (approximately 17 g protein, 8 g fat, 103 g carbohydrate, 583 calories) at least 30 minutes prior to dosing.

During each study period, 3 mL blood samples are obtained prior to each dosing and following each dose at selected times through 96 hours post-dose. Blood samples are collected in vacutainer tubes containing EDTA as a preservative.

Plasma samples are analyzed for methylphenidate and its major metabolites using a validated LC-MS-MS procedure. Concentration-time data are transferred into WinNonlin, and analyzed using noncompartmental methods. These PK analyses are suitable to determine pharmacokinetic parameters such as mean $C_{max}$, $T_{max}$, AUC, etc. Effects of co-administration of the Test Capsules with high-fat or low-fat meals are compared against study groups administered Test Capsules in the fasted state.

Example 5f

In order to assess the in vivo controlled release performance of abuse-resistant methylphenidate oral dosage forms prepared in accordance with the present invention, the following human clinical trail is carried out. The study is designed as a single-center, randomized, open-label, Phase 1 study to assess the safety and pharmacokinetics of three prototype Test Capsules (methylphenidate formulations, 48 mg) relative to Metadate CD® (40 mg) and Concerta® (36 mg) formulations in healthy male and female volunteers under fed condition. The prototype formulation evaluation is carried out in a five-way open-label, crossover study in 20 healthy subjects. A standard 5×5 Latin square design is used to assign subjects to treatments. In each sequence, subjects are given a single dose of Test Capsules (MPH1, MPH2 or MPH3) or Metadate CD® (40 mg) and Concerta® (36 mg) as reference drugs. Subjects receive the other dosing treatments in subsequent study periods according to the randomization scheme. A minimum 7-Day washout period separates each study treatment. A 48 mg dose is selected to match the $C_{max}$ of the reference products and to allow quantification of blood levels of Methylphenidate over a 48-hour time interval.

Subjects are admitted to the clinic in the evening, approximately 13 hours before each scheduled dose. At each treatment period check-in, site staff reconfirm that subjects meet inclusion and exclusion criteria and restrictions have not been violated since screening or previous confinement period. In addition, a urine sample is collected for urinalysis and to test for and drugs of abuse and pregnancy for women, a physical examination is performed and a blood sample is collected for haematology/biochemistry. A test for alcohol is also performed using a breath test Subjects remain at the clinic until completion of the 36-hour post dose blood collection and are instructed to return to the clinic for the 48-hour post dose blood samples. After check-in, each subject receives dinner. On the next day, following an overnight fast in the morning of Study Day 1 of each treatment period, subjects are provided with a standardized high fat breakfast approximately 20 minutes prior to dosing and after the pre-dose (0-hour) blood sample is drawn. The breakfast consists of one English muffin with butter, one fried egg, one slice of cheese, one slice of bacon, one 2-oz serving of hash brown potatoes, and 8 fluid oz (230 mL) whole milk. The breakfast contains an estimated Carbohydrates 41.8 g, estimated Protein 25.7 g, and estimated Fat 31.0 g.

Within 5 minutes of completion of the breakfast, each subject receives a single oral dose of the assigned study treatment to be administered with 240 mL of room temperature, non-carbonated drinking water. A mouth check will be performed after dosing to ensure that the study medication was swallowed.

A standard meal schedule with lunch, dinner and an evening snack will begin on Day 1 of each study treatment. Meals are served 5 minutes after the pre-treatment blood collection. The same menu and meal schedule is administered uniformly for all subjects and for all treatment periods. Subjects are restricted from food or beverages containing alcohol, caffeine, any xanthine-containing products, and fruit juices (including grapefruit juice) containing ascorbic acid for 48 hours before and during each treatment period of confinement. Additionally, subjects are restricted from strenuous exercise during confinement and may not lie down for the first two hours after drug administration to ensure proper stomach emptying, subjects are allowed to sit or stand during this time.

Plasma Sample Collection:

Plasma samples are collected in a 5 mL Li+ heparin vacutainer tube at prescribed time points during each study periods. The samples are processed and frozen and retained at the site until they are forwarded to a laboratory for testing.

Beginning on dosing day, 17 blood samples (5 mL/sample) are collected through the 48-hour post dose interval during each study period to determine the plasma concentration of methylphenidate. Blood samples are collected at 30 minutes before dose (pro-dose) and at 0.5, 1, 1.5, 2, 3, 4, 5, 6, 8, 10, 12, 16, 20, 24, 36 and 48 hours after administration of the study treatment.

In addition, blood is collected for screening clinical laboratory evaluation and for women subjects, blood is collected for serum pregnancy test. For women, urine pregnancy testing is conducted on the evening prior to treatment. Clinical laboratory measures (biochemistry and haematology) are performed at screening, on the evening prior to each treatment and 24 hours post-treatment (non-fasted).

Plasma samples are analyzed for methylphenidate and its major metabolites using a validated LC-MS-MS procedure. Concentration-time data are transferred into WinNonlin, and analyzed using noncompartmental methods. These PK analyses are suitable to determine pharmacokinetic parameters such as mean $C_{max}$, $T_{max}$, AUC, etc.

Example 5g

In order to compare a target pharmacokinetic profile (developed in accordance with the present invention) with a QD comparator and placebo, the following human clinical trail is carried out. The methods of the study are based on a report by Swanson et al. (2002) *J Am Acad Child Adolesc Psychiatry* 41:1306-1314. The study is carried out in a Laboratory School setting.

Patient Selection:

Children aged 7-12 years, meeting the DSM-IV criteria for a diagnosis of ADHD and taking 5 to 15 mg of methylphenidate BID or TID, or taking an equivalent dose of a long acting methylphenidate formulation selected from Concerta, Metadate CD, Focalin XR are selected for the study. Children are excluded from the study if they have abnormal blood pressure, are physically ill or if they have a primary diagnosis of defiant disorder or conduct disorder or if their diagnosis includes comorbid mood or anxiety disorder, as defined by DSM-IV criteria. Children are also excluded if they are unable to understand that they may withdraw from the study at any time.

Dosing:

The trial is designed to compare the target pharmacokinetic profile of the present invention against placebo and a QD comparator. The study is carried out using the "dose-sipping" methodology described by Swanson at al. (Swanson et al. (2002) *J Am Acad Child Adolesc Psychiatry* 41:1306-1314; Swanson et al. (2003) *Arch Gen Psychiatry* 60:204-211). For each arm of the three-arm study, capsules are given every 30 minutes over a 12-hour time period as shown in Table 13 below. In the experimental pharmacokinetic profile group, the capsules contain differing quantities of methylphenidate designed to result in the pharmacokinetic profile being investigated as determined by simulation that is based on published methylphenidate properties. Swanson et al. (1999) *Clin Pharmacol Ther* 66:295-305. In the placebo group, the capsules do not contain methylphenidate. In the comparator group, the first capsule incorporates the comparator formulation in an over-encapsulated form. Subsequent capsules are identical to placebo. The study uses a crossover design so that each subject is scheduled to experience one study day on the experimental medication, one on the comparator and one on placebo.

Study Protocol:

The study follows the laboratory school protocol that has been established at the University of California, Irvine Child Development Center and is carried out after an initial practice day to acquaint the children with the protocol, the laboratory school and the Center staff. The subjects, divided into two cohorts of 16 subjects, are further subdivided by age into two classes of eight that are evaluated over 3 consecutive days in the laboratory school.

The laboratory school schedule includes Seatwork sessions, five classroom observations during Groupwork sessions, and five playground observations during Recess sessions as outlined in Table 20. The laboratory school activity schedule is standardized to maintain comparability over multiple repetitions across the day (Swanson et al. (1999) *Ritalin*, $2^{nd}$ ed.; Greenhill et al. Eds, Mary Ann Liebert, Larchmont, N.Y.; pp 405-430) establishing a 1.5 hour cycle of activities with 20 minute period activities buffered by 5 minute transition time intervals at the beginning and end.

Seatwork sessions are standardized by requiring the students to remain seated and quiet while performing written schoolwork. Groupwork sessions are standardized by choosing activities characteristic of schoolwork (i.e., participation in a class presentation and discussion) that require cooperation but do not require students to remain seated or silent. The Recess sessions are standardized by having playground counselors lead group games. Simple rules that define appropriate and inappropriate behavior are clearly communicated to the students by teachers (in the classroom settings) and by counselors (during recess). Formal behavior modification procedures are not used.

Measures and Assessments:

Measures of behavior defined as Attention and Deportment are obtained from the Swanson, Kotkin, Agler, M-Flynn, and Pelham (SKAMP) rating scale. SKAMP scores are assigned by teachers for the classroom situations and by counselors for the Recess sessions. Using the standard classroom version of this scale (Wigal et al. (1998) *Psychopharmacol Bull* 34:47-53) 10 items (Table 21, below) are rated on a 7-point impairment scale (none, slight, mild, moderate, severe, very severe, or maximal). Averages are calculated to reflect rating-per-item for subsets of items in two subscales: a five-item "nonschoolwork" Attention Index (without ratings of written work) (items 1 to 5) and a five-item Deportment Index (items 6 to 10). A 10-item recess version of the SKAMP rating scale adapted from Swanson et al. is also used in this study, with five parallel items for Attention (items 1, 2, 3, 4, and 9) and five parallel items for Deportment (items 5, 6, 7, 8, and 10) to measure the playground behavior of children in the Recess setting.

The subjective measures of behavior (ratings of Attention and Deportment) are analyzed with mixed-effects analysis of variance (ANOVA) models. These ANOVA models include the fixed effects of treatment arms (experimental profile, placebo and comparator), situation (Seatwork, Groupwork, and Recess), session (at 2-hour intervals across the day), sequence (the six orders of treatments used), and day (test days 1, 2, and 3). Pairwise comparisons are made with the least significant difference (LSD) method.

TABLE 20

Dosing and Activity Schedule.
(S = seatwork, G = groupwork, R = recess)

| Class 1 | Class 2 | lab school activities |
|---|---|---|
| 7:00 | 7:30 | First dose |
| 7:30 | 8:00 | S1 |
| 8:00 | 8:30 | G1 |
| 8:30 | 9:00 | S1 |
| 9:00 | 9:30 | R1 |
| 9:30 | 10:00 | S2 |
| 10:00 | 10:30 | G2 |
| 10:30 | 11:00 | S2 |
| 11:00 | 11:30 | R2 |
| 11:30 | 12:00 | S3 |
| 12:00 | 12:30 | G3 |
| 12:30 | 13:00 | S3 |
| 13:00 | 13:30 | R3 |
| 13:30 | 14:00 | S4 |
| 14:00 | 14:30 | G4 |
| 14:30 | 15:00 | S4 |
| 15:00 | 15:30 | R4 |
| 15:30 | 16:00 | S5 |
| 16:00 | 16:30 | G5 |
| 16:30 | 17:00 | S5 |
| 17:00 | 17:30 | R5 |
| 17:30 | 18:00 | S6 |
| 18:00 | 18:30 | G6 |
| 18:30 | 19:00 | S6 |
| 19:00 | 19:30 | R6 |
| 19:30 | 20:00 | Finish |

TABLE 21

The SKAMP Rating Scales

| The 10 SKAMP Items | The Recess SKAMP Scale |
|---|---|
| 1. Getting started (on assignments) | 1. Getting started (on play activities) |
| 2. Sticking with task (for entire period) | 2. Staying on task (over entire recess) |
| 3. Completing assigned work | 9. Completing games |
| 4. Performing work accurately | 4. Interacting with peers (at recess) |
| 5. Being careful and neat when writing | 7. Interacting with playground staff |
| 6. a. Interacting with other students  b. Interacting with the teacher | 5. Verbal interactions |
| 7. Remaining quiet | 6. Staying in assigned area |
| 8. Remaining seated | 3. Carelessness or recklessness |
| 9. Complying with teacher's requests | 8. Participation in group activities |
| 10. Following school rules | 10. Stopping and making transitions |

The invention claimed is:

1. An oral controlled release dosage form comprising a formulation comprising:
   methylphenidate;
   sucrose acetate isobutyrate (SAIB);
   a rheology modifier;
   a network former;
   a solvent;
   a viscosity enhancing agent; and
   a saturated polyglycolized glyceride.

2. The controlled release oral dosage form of claim 1, wherein said dosage form is characterized by providing:
   (i) an initial increasing in vivo rate of release of methylphenidate from the controlled release dosage form suitable to provide an initial increasing-rate phase of less than or equal to about 2 hours, and sufficient to provide a therapeutically effective amount of methylphenidate for a rapid onset of action; and
   (ii) a second, non-ascending in vivo rate of release of methylphenidate from the controlled release dosage form that provides a subsequent non-ascending phase sufficient to provide a therapeutically effective amount of methylphenidate through at least 11 hours post administration.

3. The controlled release oral dosage form of claim 2, wherein the initial increasing-rate phase is sufficient to provide an onset of action within about 1 hour post administration.

4. The controlled release oral dosage form of claim 2, wherein the subsequent non-ascending phase is sufficient to provide a therapeutically effective amount of methylphenidate through at least 12 hours post administration.

5. The controlled release oral dosage form of claim 1, wherein the dosage form is abuse-resistant.

6. The abuse-resistant controlled release oral dosage form of claim 5, wherein the formulation provides a decreased risk of misuse or abuse.

7. The abuse-resistant controlled release oral dosage form of claim 6, wherein said decreased risk of misuse or abuse is characterized by a low in vitro solvent extractability value of the methylphenidate from the dosage form, wherein less than 45% of the methylphenidate is extracted after 60 min of extraction in 40% ethanol at 25° C.

8. The abuse-resistant controlled release oral dosage form of claim 6, wherein said decreased risk of misuse or abuse is characterized by a $C_{max}$ ratio for methylphenidate when the dosage form is ingested by a subject with water relative to when the dosage form is ingested by the subject with 40% ethanol of about 0.8 to 1.2, and an AUC ratio for methylphenidate when the dosage form is ingested by the subject with water relative to when the dosage for is ingested by the subject with 40% ethanol of about 0.8 to 1.2.

9. The abuse-resistant controlled release oral dosage form of claim 6, wherein said decreased risk of misuse or abuse is characterized by a low injectability potential, wherein the force required to inject 1 gram of the formulation from a 3 ml syringe through an 18 G needle exceeds 62 N at a crosshead speed of 150 mm/min at 25° C.

10. The abuse-resistant controlled release oral dosage form of claim 5, wherein said dosage form is not susceptible to common forms of abuse comprising injection, inhalation and volatilization.

11. A method of treating Attention Deficit Disorder (ADD) or Attention Deficit Hyperactivity Disorder (ADHD) in a subject, said method comprising administering the controlled release oral dosage form of claim 1 to the subject on a once-day (QD) basis.

12. The controlled release oral dosage form of claim 1, wherein the viscosity enhancing agent comprises a stiffening agent.

13. The controlled release oral dosage form of claim 12, wherein the viscosity enhancing agent comprises $SiO_2$.

14. The controlled release oral dosage form of claim 1, wherein the solvent comprises triacetin.

15. The controlled release oral dosage form of claim 1, wherein the rheology modifier comprises isopropyl myristate (IPM).

16. The controlled release oral dosage form of claim 1, wherein the network former comprises cellulose acetate butyrate (CAB).

* * * * *